(12) United States Patent
Khan et al.

(10) Patent No.: US 6,921,751 B1
(45) Date of Patent: Jul. 26, 2005

(54) IMMUNOREGULATOR

(75) Inventors: Nisar Ahmed Khan, Rotterdam (NL); Hubertus Franciscus Josef Savelkoul, Bennekom (NL); Robbert Benner, Barendrecht (NL)

(73) Assignee: Erasmus Universiteit Rotterdam, Rotterdam (NL)

( * ) Notice: Subject to any disclaimer, the term of this patent is extended or adjusted under 35 U.S.C. 154(b) by 8 days.

(21) Appl. No.: 09/716,777

(22) Filed: Nov. 20, 2000

Related U.S. Application Data

(63) Continuation of application No. PCT/NL99/00313, filed on May 20, 1999.

(30) Foreign Application Priority Data

May 20, 1998 (EP) .............................. 98201695
Aug. 12, 1998 (EP) .............................. 98202706

(51) Int. Cl.$^7$ ............................................. A61K 38/24
(52) U.S. Cl. ............................. 514/21; 514/2; 424/545; 424/546
(58) Field of Search ................................ 424/545, 546; 514/2, 21

(56) References Cited

U.S. PATENT DOCUMENTS

| | | | |
|---|---|---|---|
| 4,977,244 | A | 12/1990 | Muchmore et al. |
| 5,380,668 | A | 1/1995 | Herron |
| 5,677,275 | A | 10/1997 | Lunardi-Iskandar et al. |
| 5,851,997 | A | 12/1998 | Harris |
| 5,854,004 | A | 12/1998 | Czernilofsky et al. |
| 5,877,148 | A | 3/1999 | Lunardi-Iskandar et al. |
| 5,958,413 | A | 9/1999 | Anagnostopulos et al. |
| 5,968,513 | A | 10/1999 | Gallo et al. |
| 5,997,871 | A | 12/1999 | Gallo et al. |
| 6,319,504 | B1 | 11/2001 | Gallo et al. |
| 6,361,992 | B1 | 3/2002 | Szkudlinski et al. |
| 6,489,296 | B1 | 12/2002 | Grinnell et al. |
| 6,583,109 | B1 | 6/2003 | Gallo et al. |
| 6,596,688 | B1 | 7/2003 | Gallo et al. |
| 6,620,416 | B1 | 9/2003 | Gallo et al. |
| 2002/0041871 | A1 | 4/2002 | Brudnak |
| 2002/0064501 | A1 | 5/2002 | Khan et al. |
| 2003/0049273 | A1 | 3/2003 | Gallo et al. |
| 2003/0113733 | A1 | 6/2003 | Khan et al. |
| 2003/0119720 | A1 | 6/2003 | Khan et al. |
| 2003/0166556 | A1 | 9/2003 | Khan et al. |
| 2003/0186244 | A1 | 10/2003 | Margus et al. |
| 2003/0215434 | A1 | 11/2003 | Khan et al. |
| 2003/0219425 | A1 | 11/2003 | Khan et al. |
| 2003/0220257 | A1 | 11/2003 | Benner et al. |
| 2003/0220258 | A1 | 11/2003 | Benner et al. |
| 2003/0220259 | A1 | 11/2003 | Benner et al. |
| 2003/0220260 | A1 | 11/2003 | Khan et al. |
| 2003/0220261 | A1 | 11/2003 | Khan et al. |
| 2003/0224995 | A1 | 12/2003 | Khan et al. |
| 2004/0013661 | A1 | 1/2004 | Wensvoort et al. |

FOREIGN PATENT DOCUMENTS

| | | |
|---|---|---|
| DE | 3715662 | 11/1987 |
| DE | 19953339 | 5/2001 |
| EP | 1 138 692 A1 | 10/2001 |
| EP | 1 300 418 | 4/2003 |
| FR | 2 706 772 | 12/1994 |
| WO | 96/04008 | 2/1996 |
| WO | 97/49373 | 12/1997 |
| WO | 97/49418 | 12/1997 |
| WO | 97/49432 | 12/1997 |
| WO | WO 97/49721 | 12/1997 |
| WO | WO 98/35691 | 8/1998 |
| WO | WO 99/59617 | 11/1999 |
| WO | WO 01/10907 | 2/2001 |
| WO | WO 01/10907 A2 | 2/2001 |
| WO | WO 01/11048 A | 2/2001 |
| WO | WO 01/11048 A2 | 2/2001 |
| WO | WO 01/010907 A3 | 2/2001 |
| WO | WO 01/72831 | 10/2001 |
| WO | WO 02/085117 | 10/2002 |
| WO | WO 03/029292 A2 | 4/2003 |

OTHER PUBLICATIONS

Christman et al., Nuclear factor kappaB: a pivotal role in the systemic inflammatory response syndrome and new target for therapy, Intens Care Med, 1998, pp. 1131–1138, vol. 24.

Jyonouchi et al., Proinflammatory and regulatory cytokine production accociated with innate and adaptive immune respones in children with autism spectrum disorders and developmental regression, J Neuroim., 2001, pp. 170–179, vol. 120.

Kanungo et al., Advanced Maturation of Heteropneustes Fossilis (Bloch) by Oral Administration of Human Chorionic Gonadotropin, J. Adv. Zool., 1999, pp. 1–5, vol. 20.

Rohrig et al., Growth–stimulating Influence of Human Chorionic Gonadotropin (hCG) on *Plasmodium falciparum* in vitro, Zentralblatt Bakt, 1999, pp. 89–99, vol. 289.

Tak et al., NF–kappaB: a key role in inflammatory diseases, J Clin Invest., 2001, pp. 7–11, vol. 107.

Tan et al., The role of activation of nuclear factor–kappa B of rat brain in the pathogenesis of experimental allergic encephalomyelitis, Acta Physiol Sinica, 2003, pp. 58–64, vol. 55.

Tovey et al., Mucosal Cytokine Therapy: Marked Antiviral and Antitumor Activity, J. Interferon Cytokine Res., 1999, pp. 911–921, vol. 19.

(Continued)

Primary Examiner—Jean C. Witz
(74) Attorney, Agent, or Firm—TraskBritt

(57) ABSTRACT

The invention relates to the field of immunology. Specifically, the invention relates to the field of immune-mediated disorders such as allergies, auto-immune disease, transplantation-related disease or inflammatory disease. The invention provides for an immunoregulator (IR), use of an IR in preparing a pharmaceutical composition for treating an immune-mediated disorder and a method for treating an immune-mediated disorder.

34 Claims, 69 Drawing Sheets

OTHER PUBLICATIONS

Figure 1:
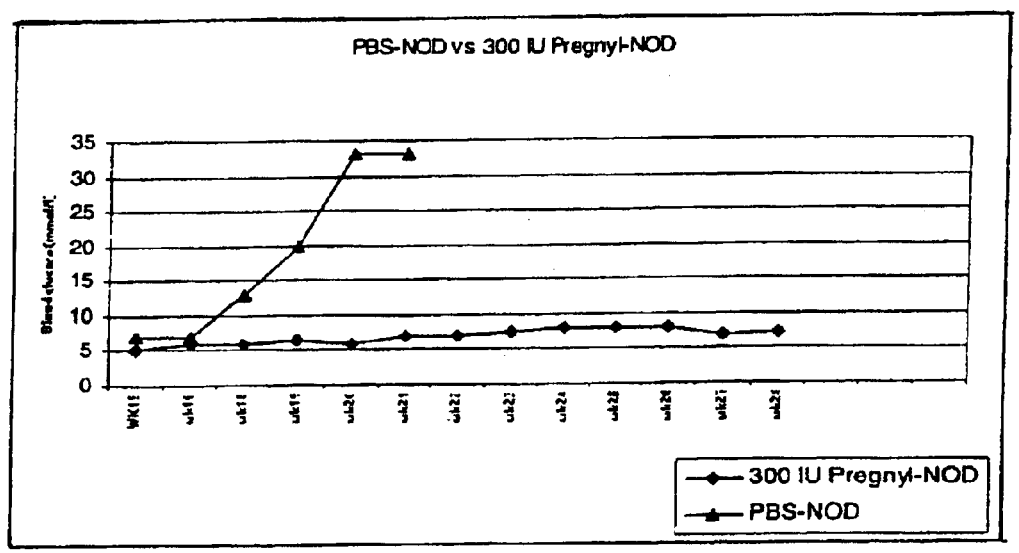

Albini, A., et al., "Old drugs as novel angiogenesis inhibitors: Preclinical studies with NAC, hCG, EGCG and somatostatin," 17 Clinical & Experimental Metastasis 739 (1999).

Blackwell, Timothy, S., et al., "The Role of Nuclear Factor–kB in Cytokine Gene Regulation," 17 Am. J. Respir. Cell Mol. Biol. 3–9 (1997).

Keller, S., et al., "Human Chorionic Gonadotropih (hCG) Is a Potent Angiogenic Factor for Uterine Endothelial Cells in Vitro," 20(5–6) PLACENTA, p. A37 (Jul. 1999).

Khan, Nisar A., et al., "Inhibition of Diabetes in NOD Mice by Human Pregnancy Factor," 62(12) Human Immunology 1315–1323 (Dec. 2001).

Khan, Nisar A., et al., "Inhibition of Septic Shock in Mice by an Oligopeptide From the β–Chain of Human Chorionic Gonadotrophin Hormone," 63(1) Human Immunology 1–7 (Jan. 2002).

Muchmore et al., Immunoregulatory Properties of Fractions from Human Pregnancy Urine: Evidence that Human Chorionic Gonadotropin is not Responsible, The Journal of Immunology, Mar. 1997, pp. 881–886, vol. 118, No. 3.

Muchmore et al., Purification and Characterization of a Mannose–Containing Disaccharide Obtained from Human Pregnancy Urine, Journal of Experimental Medicine, Dec. 1984, pp. 1672–1685, vol. 160.

Patil, A., et al., "The Study of the Effect of Human Chorionic Gonadotrophic (HCG) Hormone on the Survival of Adrenal Medulla Transplant in Brain. Preliminary Study," 87 Acta Neurochir (WIEN) 76–78 (1987).

Slater, Lewis M., et al., "Decreased Mortality of Murine Graft–Versus–Host Disease by Human Chorionic gonadotropin,"23(1) Transplantations 103–104 (Jan. 1977).

Wulczyn, F. Gregory, et al., "The NF–kB/Rel and IkB gene families: mediators of immune response and inflammation," 74(12) J. Mol. Med. 749–769 (1996).

Yamamoto, Y., et al., "Role of the NF–kB Pathway in the Pathogenesis of Human Disease States," 1(3) Current Molecular Medicine 287–296 (Jul. 2001).

Connelly et al., Biphasic Regulation of NF–kB Activity Underlies the Pro– and Anti–inflammatory Actions of Nitric Oxide, The Journal of Immunology, 2001, pp. 3873–3881, 166, The American Association of Immunologists, USA.

Friedlander, Tackling anthrax, Nature, Nov. 8, 2001, pp. 160–161, vol. 414.

Medzhitov, Toll–like Receptors and Innate Immunity, Nature Reviews/Immunology, Nov. 2001, pp. 135–145, vol. 1.

PCT International Preliminary Examination Report, PCT/NI99/00313, dated Jul. 21, 2000, 6 pages.

PCT International Search Report, PCT/NL99/00313, dated Nov. 29, 1999, 3 pages.

Notification of Transmittal of the International Preliminary Examination Report.

International Search Report, publication date Jan. 13, 2000.

Lang et al., "Induction of apoptosis in Kaposi's sarcoma spindle cell cultures by the subunits of human chorionic gonadotropin", *AIDS* 1997, vol. 11, No. 11, pp. 1333–1340.

Iskandar et al., "Effects of a urinary factor from women in early pregnancy on HIV–1. SIV and associated disease", Nature Medicine, Apr. 1998, vol. 4, No. 4, pp. 428–434.

Figure 31
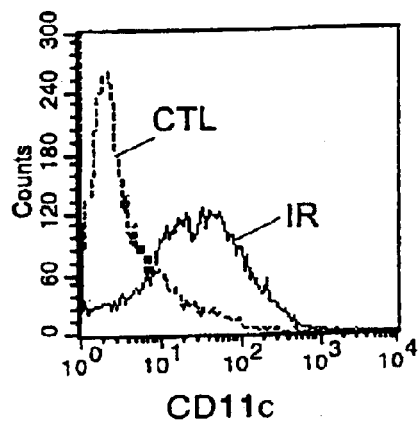
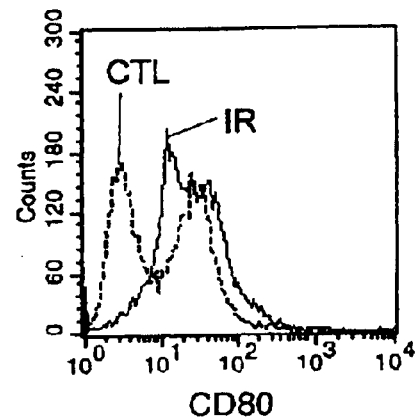
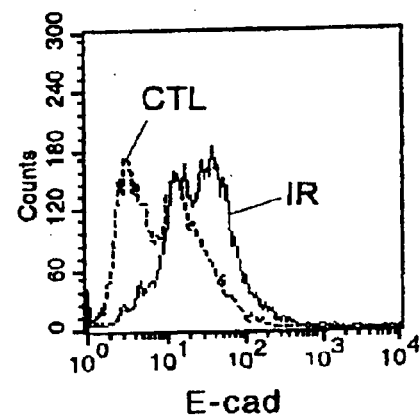
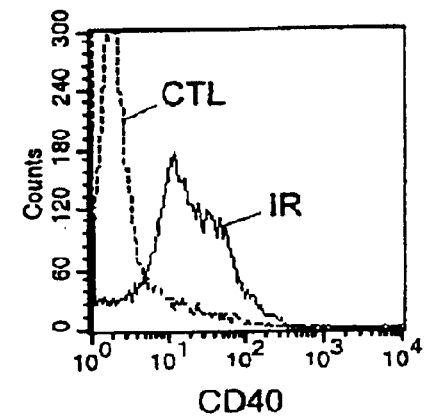
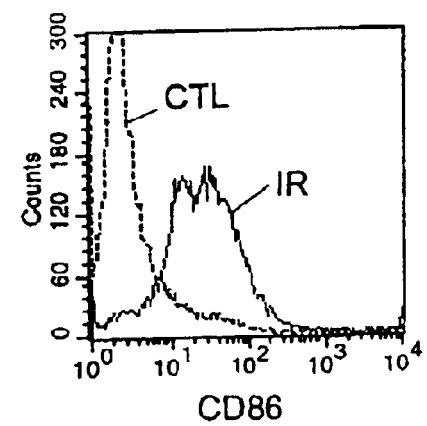
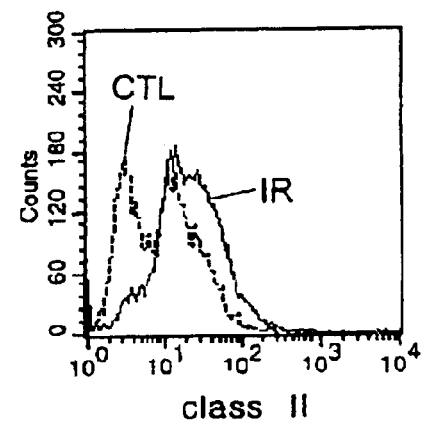

| Mab | Med | IR-P | IR-U | IR-U3-5 | IR-U/LMDF |
|---|---|---|---|---|---|
| CD1d | 4.9 | 3.2 | 2.4 | 2.8 | 2.8 |
| CD14 | 0.0 | 0.6 | 2.7 | 1.0 | 0.8 |
| CD40 | 0.0 | 0.0 | 0.0 | 0.0 | 0.0 |
| CD80 | 0.3 | 0.0 | 0.0 | 0.0 | 0.0 |
| CD86 (all) | 1.9 | 0.8 | 0.1 | 0.5 | 0.6 |
| CD95 (all) | 5.3 | 4.1 | 12.8 | 5.6 | 5.6 |
| CD95L | 0.2 | 0.3 | 0.2 | 0.0 | 0.0 |
| ER-MP58 | 3.9 | 2.6 | 1.7 | 0.0 | 1.1 |
| F4/80 (all) | 39.5 | 20.1 | 1.3 | 2.2 | 0.0 |
| RB6.8C5 |  | 3.6 | 5.8 | 5.0 | 4.1 |
| E-cad (all) | 1.9 | 4.5 | 0.5 | 0.5 | 0.9 |
| MHC II | 13.8 | 7.8 | 9.3 | 6.3 | 0.0 |

Figure 54

| Mab | Med | IR-P | IR-U | IR-U3-5 | IR-U/LMDF |
|---|---|---|---|---|---|
| CD1d | 4.9 | 7.0 | 11.8 | 9.5 | 9.5 |
| CD14 | 0.0 | 1.0 | 0.9 | 1.9 | 1.2 |
| CD40 | 0.0 | 0.6 | 4.4 | 5.5 | 3.8 |
| CD80 | 0.3 | 0.3 | 0.9 | 0.7 | 0.6 |
| CD80 (fractie) |  |  | 8.0 (37%) | 16.0 (20%) | 12.8 (20%) |
| CD86 (all) | 1.9 | 3.3 | 19.7 | 10 | 11.5 |
| CD95 | 5.3 |  | 15.2 | 16 | 16 |
| ER-MP58 | 3.9 | 5.2 | 6.1 | 7.7 | 7.0 |
| F4/80 (all) | 39.5 | 32.2 | 108.8 | 136.9 | 158.7 |
| RB6.8C5 |  | 7.7 | 8.2 | 4.0 | 4.3 |
| E-cad (all) | 1.9 | 2.1 | 3.2 | 3.3 | 1.9 |
| MHC II (all) | 13.8 | 18.1 | 108.8 | 94.5 | 109.6 |

Figure 55

Figure 81
| | Before Tx | during Tx | end Tx | Normal (X 10e9 |
|---|---|---|---|---|
| Lymphocytes | 0.59 | 0.75 | 1.56 | 1.5 - 4.0 |
| T cell | 0.57 | 0.72 | 1.48 | 0.9 - 2.8 |
| CD4 | 0.24 | 0.26 | 0.59 | 0.5 - 1.7 |
| CD8 | 0.31 | 0.41 | 0.23 | 0.3 - 0.8 |
| B-cell | 0.01 | 0.01 | 0.01 | 0.1 - 0.3 |
Figure (82a)
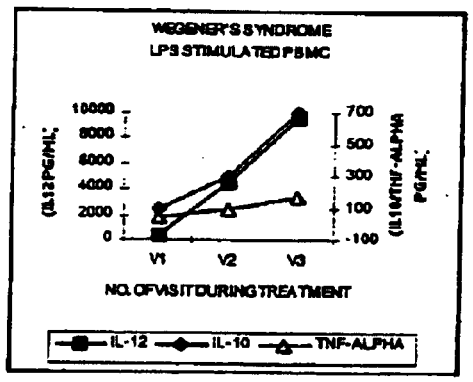
Figure (82b)
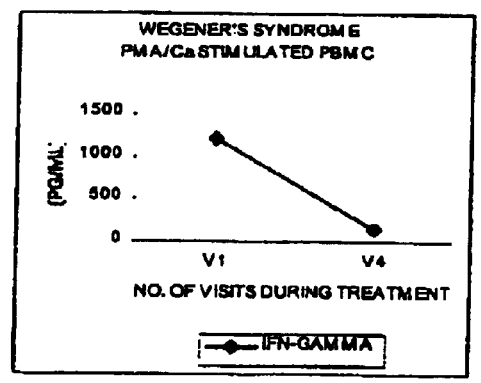

Figure 83
|            | Before Tx | during Tx | end Tx | Normal (X 10e9 |
|------------|-----------|-----------|--------|----------------|
| Lymphocytes | 2.87     | 2.06      | 1.22   | 1.5 - 4.0      |
| T cell     | 2.35      | 1.59      | 1.02   | 0.9 - 2.8      |
| CD4        | 1.95      | 1.26      | 0.82   | 0.5 - 1.7      |
| CD8        | 0.49      | 0.37      | 0.18   | 0.3 - 0.8      |
| B-cell     | 0.33      | 0.19      | 0.14   | 0.1 - 0.3      |
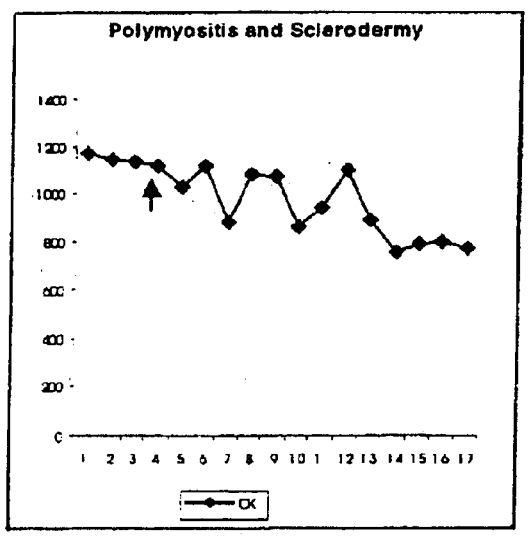
Figure 84
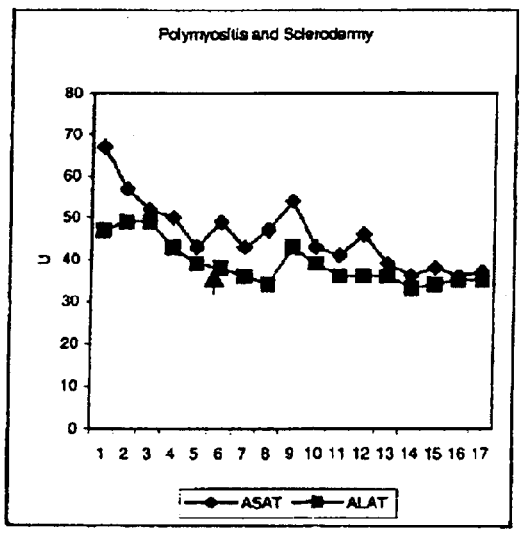
Figure 85

GPC 60 Å

IMMUNOREGULATOR

RELATED APPLICATIONS

This application is a continuation of co-pending International Application No. PCT/NL99/00313, filed May 20, 1999, designating the United States of America.

TECHNICAL FIELD

The invention relates to the field of immunology, more specifically to the field of immune-mediated disorders such as allergies, auto-immune disease, transplantation-related disease or inflammatory disease.

The immune system produces cytokines and other humoral factors to protect the host when threatened by inflammatory agents, microbial invasion, or injury. In most cases this complex defense network successfully restores normal homeostasis, but at other times the immunological mediators may actually prove deleterious to the host. Some examples of immune disease and immune system-mediated injury have been extensively investigated including anaphylactic shock, autoimmune disease, and immune complex disorders.

Recent advances in humoral and cellular immunology, molecular biology and pathology have influenced current thinking about auto-immunity being a component of immune-mediated disease. These advances have increased our understanding of the basic aspects of antibody, B-cell, and T-cell diversity, the generation of innate (effected by monocytes, macrophages, granulocytes, natural killer cells, mast cells, γδ T cells, complement, acute phase proteins, and such) and adaptive (T and B cells and antibodies) or cellular and humoral immune responses and their interdependence, the mechanisms of (self)-tolerance induction and the means by which immunological reactivity develops against auto-antigenic constituents.

Since 1900, the central dogma of immunology has been that the immune system does not normally react to self. However, it as recently become apparent that auto-immune-responses are not as rare as once thought and that not all auto-immune responses are harmful; some responses play a distinct role in mediating the immune response in general. For example, certain forms of auto-immune response such as recognition of cell surface antigens encoded by the major histocompatibility complex (MHC) and of anti-idiotypic responses against self idiotypes are important, indeed essential, for the diversification and normal functioning of the intact immune system.

Apparently, an intricate system of checks and balances is maintained between various subsets of cells (i.e. T-cells) of the immune system, thereby providing the individual with an immune system capable of coping with foreign invaders. In that sense, auto-immunity plays a regulating role in the immune system.

However, it is now also recognised that an abnormal auto-immune response is sometimes a primary cause and at other times a secondary contributor to many human and animal diseases. Types of auto-immune disease frequently overlap, and more than one auto-immune disorder tends to occur in the same individual, especially in those with auto-immune endocrinopathies. Auto-immune syndromes may be mediated with lymphoid hyperplasia, malignant lymphocytic or plasma cell proliferation and immunodeficiency disorders such as hypogammaglobulinaemie, selective Ig deficiencies and complement component deficiencies.

Auto-immune diseases, such as systemic lupus erythematosus, diabetes, rheumatoid arthritis, post-partum thyroid dysfunction, auto-immune thromocytopenia, to name a few, are characterised by auto-immune responses, for example directed against widely distributed self-antigenic determinants, or directed against organ- or tissue specific antigens. Such disease may follow abnormal immune responses against only one antigenic target, ore against many self antigens. In many instances, it is not clear whether auto-immune responses are directed against unmodified self-antigens or self-antigens that have been modified (or resemble) any of numerous agents such as viruses, bacterial antigens and haptenic groups.

There is as yet no established unifying concept to explain the origin and pathogenesis of the various auto-immune disorders. Studies in experimental animals support the notion that auto-immune diseases may result from a wide spectrum of genetic and immunological abnormalities which differ from one individual to another and may express themselves early or late in life depending on the presence or absence of many superimposed exogenous (viruses, bacteria) or endogenous (hormones, cytokines, abnormal genes) accelerating factors.

It is evident that similar checks and balances that keep primary auto-immune disease at bay are also compromised in immune mediated disorders, such as allergy (asthma), acute inflammatory disease such as sepsis or septic shock, chronic inflammatory disease (i.e rheumatic disease, Sjögrens syndrome, multiple sclerosis), transplantation-related immune responses (graft-versus-host-disease, post-transfusion thrombocytopenia), and many others wherein the responsible antigens (at least initially) may not be self-antigens but wherein the immune response to said antigen is in principle not wanted and detrimental to the individual. Sepsis is a syndrome in which immune mediators, induced by for example microbial invasion, injury or through other factors, induce an acute state of inflammation which leads to abnormal homeostasis, organ damage and eventually to lethal shock. Sepsis refers to a systemic response to serious infection. Patients with sepsis usually manifest fever, tachycardia, tachypnea, leukocytosis, and a localised site of infection. Microbiologic cultures from blood or the infection site are frequently, though not invariably, positive. When this syndrome results in hypotension or multiple organ system failure (MOSF), the condition is called sepsis or septic shock. Initially, micro-organisms proliferate at a nidus of infection. The organisms may invade the bloodstream, resulting in positive blood cultures, or might grow locally and release a variety of substances into the bloodstream. Such substances, when of pathogenic nature are grouped into two basic categories: endotoxins and exotoxins. Endotoxins typically consist of structural components of the micro-organisms, such as teichoic acid antigens from staphylococci or endotoxins from gram-negative organisms μlike LPS). Exotoxins (e.g. toxic shock syndrome toxin-1, or staphlococcal enterotoxin A, B or C) are synthesized and directly released by the micro-organisms.

As suggested by their name, both of these types of bacterial toxins have pathogenic effects, stimulating the release of a large number of endogenous host-derived immunological mediators from plasma protein precursors or cells (monocytes/macrophages, endothelial cells, neutrophils, T cells, and others).

It is in fact generally these immunological mediators which cause the tissue and organ damage associated with sepsis or septic shock. Some of these effects stem from direct mediator-induced injury to organs. However, a portion of shock-associated-organ dysfunction is probably due to mediator-induced abnormalities in vasculature, resulting in abnormalities of systemic and regional blood flow, causing refractory hypotension or MOSF (Bennett et al.).

The non-obese diabetic (NOD) mouse is a model for auto-immune disease, in this case insulin-dependent diabetes mellitus (IDDM) which main clinical feature is elevated blood glucose levels (hyperglycemia). Said elevated blood glucose level is caused by auto-immune destruction of insulin-producing β cells in the islets of Langerhans of the pancreas (Bach et al. 1991, Atkinson et al. 1994). This is accompanied by a massive cellular infiltration surrounding and penetrating the islets (insulitis) composed of a heterogeneous mixture of CD4+ and CD8+ T lymphocytes, B lymphocytes, macrophages and dendritic cells (O'Reilly et al. 1991).

The NOD mouse represents a model in which auto-immunity against beta-cells is the primary event in the development of IDDM. Diabetogenesis is mediated through a multifactorial interaction between a unique MHC class II gene and multiple, unlinked, genetic loci, as in the human disease. Moreover, the NOD mouse demonstrates beautifully the critical interaction between heredity and environment, and between primary and secondary auto-immunity, its clinical manifestation is for example depending on various external conditions, most importantly of the micro-organism load of the environment in which the NOD mouse is housed.

As for auto-immunity demonstrable in NOD mice, most antigen-specific antibodies and T-cell responses are measured after these antigens were detected as self-antigens in diabetic patients. Understanding the role these auto-antigens play in NOD diabetes may further allow to distinguish between pathogenic auto-antigens and auto-immunity that is an epiphenomenon.

In general, T lymphocytes play a pivotal role in initiating the immune mediated disease process (Sempe et al. 1991, Miyazaki et al. 1985, Harada et al. 1986, Makino et al. 1986). CD4+ T-cells can be separated into at least two major subsets Th1 and Th2. Activated Th1 cells secrete IFN-γ and TNF-α, while Th2 cells produce IL-4, IL-5 and IL-10. Th1 cells are critically involved in the generation of effective cellular immunity, whereas Th2 cells are instrumental in the generation of humoral and mucosal immunity and allergy, including the activation of eosinophils and mast cells and the production of IgE (Abbas et al. 1996). A number of studies have now correlated diabetes in mice and human with Th1 phenotype development (Liblau et al. 1995, Katz et al. 1995). On the other hand, Th2 T cells are shown to be relatively innocuous. Some have even speculated that Th2 T cells in fact, may be protective. Katz et al. have shown that the ability of CD4+ T cells to transfer diabetes to naïve recipients resided not with the antigen specificity recognised by the TCR per se, but with the phenotypic nature of the T cell response. Strongly polarised Th1 T cells transferred disease into NOD neonatal mice, while Th2 T cells did not, despite being activated and bearing the same TCR as the diabetogenic Th1 T cell population. Moreover, upon co-transfer, Th2 T cells could not ameliorate the Th1-induced diabetes, ever when Th2 cells were co-transferred in 10-fold excess (Pakale et al. 1997).

The incidence of sepsis or septic shock has been increasing since the 1930's, and all recent evidence suggests that this rise will continue. The reasons for this increasing incidence are many: increased use of invasive devices such as intravascular catheters, widespread use of cytotoxic and immunosuppressive drug therapies for cancer and transplantation, increased longevity of patients with cancer and diabetes who are prone to develop sepsis, and an increase in infections due to antibiotic-resistant organisms. Sepsis or septic shock is the most common cause of death in intensive care units, and it is the thirteenth most common cause of death in the United States. The precise incidence of the disease is not known because it is not reportable; however, a reasonable annual estimate for the United States is 400,000 bouts of sepsis, 200,000 cases of septic shock, and 100,000 deaths from this disease.

Various micro-organisms, such as Gram-negative and Gram-positive bacteria, as well as fungi, can cause sepsis and septic shock. Certain viruses and rickettsiae probably can produce a similar syndrome. Compared with Gram-positive organisms, Gram-negative bacteria are somewhat more likely to produce sepsis or septic shock. Any site of infection can result in sepsis or septic shock. Frequent causes of sepsis are pyelonephritis, pneumonia, peritonitis, cholangitis, cellulitis, or meningitis. Many of these infections are nosocomial, occurring in patients hospitalised for other medical problems. In patients with normal host defences, a site of infection is identified in most patients. However, in neutropenic patients, a clinical infection site is found in less than half of septic patients, probably because small, clinically inapparent infectious in skin or bowel can lead to bloodstream invasion in the absence of adequate circulating neutrophils. Clearly there is a need to protect against sepsis or septic shock in patients running such risks.

Recently, considerable effort has been directed toward identifying septic patients early in their clinical course, when therapies are most likely to be effective. Definitions have incorporated manifestations of the systemic response to infection (fever, tachycardia, tachypnea, and leukocytosis) along with evidence of organ system dysfunction (cardiovascular, respiratory, renal, hepatic, central nervous system, hematologic, or metabolic abnormalities). The moat recent definitions use the term systemic inflammatory response syndrome (SIRS) emphasizing that sepsis is one example of the body's immunologically-mediated inflammatory responses that can be triggered not only by infections but also by noninfectious disorders, such as trauma and pancreatitis (for interrelationships among systemic inflammatory response (SIRS), sepsis, and infection, see Crit. Care Med. 20:864, 1992: For a review of pathogenic sequences of the events in sepsis or septic shock see N Engl J Med 328:1471, 1993).

Toxic shock syndrome toxin (TSST-1) represents the most clinically relevant exotoxin, identified as being the causative agent in over 90% of toxic shock syndrome cases (where toxic shock is defined as sepsis or septic shock caused by super-antigenic exotoxins). Super antigens differ from "regular" antigens in that they require no cellular processing before being displayed on a MHC molecule. Instead they bind to a semi-conserved region on the exterior of the TCR and cause false "recognition" of self antigens displayed on MHC class II (Perkins et al.; Huber et al. 1993). This results in "false" activation of both the T cell and APC leading to proliferation, activation of effector functions and cytokine secretion. Due to the superantigen's polyclonal activation of T cells, a systemic wide shock results due to excessive inflammatory cytokine release. (Huber et al. 1993, Miethke et al. 1992).

The inflammatory cytokines involved in sepsis are similar. These immunological mediators are tumor necrosis factor (TNF), interferon gamma (IFN-gamma), nitric oxide (Nox) and interleukin 1(IL-1), which are massively related by monocytes, macrophages and other leukocytes in response to bacterial toxins (Bennett et al., Gutierrez-Ramos et al 1997). The release of TNF and other endogenous mediators may lead to several patho-physiological reactions in sepsis, such as fever, leukopenia, thrombocytopenia, hemodynamic changes, disseminated intravascular coagulation, as well as leukocyte infiltration and inflammation in various organs, all of which may ultimately lead to death. TNF also causes endothelial cells to express adhesion receptors (selectins) and can activate neutrophils to express ligands for these receptors which help neutrophils to adhere with endothelial cell surface for adherence, margination, and migration into tissue inflammatory foci (Bennett et al.). Blocking the adhesion process with monoclonal antibodies prevents tissue injury and improves survival in certain animal models of sepsis or septic shock (Bennett et al.).

These findings, both with auto-immune disease, as well as with acute and chronic inflammatory disease, underwrite the postulated existence of cells regulating the balance between activated Th-sub-populations. Possible disturbances in this balance that are induced by altered reactivity of such regulatory T cell populations can cause immune-mediated diseases, which results in absence or over-production of certain critically important cytokines (O'Garra et al. 1997). These Th-sub-populations are potential targets for pharmacological regulation of immune responses.

In general, immune mediated disorders are difficult to treat. Often, broad-acting medication is applied, such as treatment with corticosteroids or any other broad acting anti-inflammatory agent that in many aspects may be detrimental to a treated individual.

In general there is a need for better and more specific possibilities to regulate the checks and balances of the immune system and treat immune mediated disorders.

The invention provides among others an immunoregulator (IR), use of an IR in preparing a pharmaceutical composition for treating an immune-mediated disorder, a pharmaceutical composition and a method for treating an immune-mediated disorder. Immune-mediated disorders as described herein include chronic inflammatory disease, such as diabetes type I or II, rheumatic disease, Sjögrens syndrome, multiple sclerosis), transplantation-related immune responses such as graft-versus-host-disease, post-transfusion thrombocytopenia, chronic transplant rejection, pre-eclampsia, atherosclerosis, asthma, allergy and chronic auto-immune disease, and acute inflammatory disease, such as (hyper) acute transplant rejection, septic shock and acute autoimmune disease. Autoimmune diseases are a group of disorders of in general unknown etiology. In most of these diseases production of autoreactive antibodies and/or autoreactive T lymphocytes can be found. An autoimmune response may also occur as manifestation of viral or bacterial infection and may result in severe tissue damage, for example destructive hepatitis because of Hepatitis B virus infection.

Autoimmune diseases can be classified as organ specific or non-organ specific depending on whether the response is primarily against antigens localised in particular organs, or against wide-spread antigens. The current mainstay of treatment of autoimmune diseases is immune suppression and/or. (because of tissue impairment), substitution of vital components like hormone substitution. However, immunosuppressive agents such as steroids or cytostatic drugs have significant side effects, which limits their application. Now, the use of more specific immunoregulatory drugs is provided by the invention in the treatment of autoimmune disease and other inflammation. Based on the immunoregulatory properties as described below, e.g. by regulating the Th1/Th2 ratio, modulating dendritic cell differentiation the low side-effect profile, the initial clinical observations, etc., it shows these preparations to be very helpful in the treatment of patients with immune-mediated inflammation, such autoimmune disease.

A non-limiting list of an immune diseases includes; Hashimoto's thyroditis, primary mysxoedema thyrotoxicosis, pernicious anaemia, autoimmune atrophic gastritis, Addison's disease, premature menopause, insulin-dependent diabetes mellitus, stiff-man syndrome, Goodpasture's syndrome, myasthenia gravis, male infertility, pemphigus vulgaris, pemphigoid, sympathetic ophthalmia, phacogenic uveitis, multiple sclerosis, autoimmune haemolytic anaemia, idiopathic thrombocytopenic purpura, idiopathic leucopenia, primary biliary cirrhosis, active chronic hepatitis, cryptogenic cirrhosis, ulcerative colitis, Sjögren's syndrome, rheumatoid arthritis, dermatomyositis, polymyositis, scleroderma, mixed connective tissue disease, discoid lupus erythematosus, and systemic lupus erythematosus.

In one embodiment, the invention provides an immunoregulator capable of down-regulating Th1 cell levels and/or upregulating Th2 cell levels, or influencing their relative ratio in an animal, said immunoregulator obtainable from urine or other sources of bodily products, such as serum, whey, placental extracts, cells or tissues. Obtainable herein refers to directly or indirectly obtaining said IR from said source, IR is for example obtained via chemical synthesis or from animal or plant sources in nature.

In a preferred embodiment, the invention allows regulating relative ratios and/or cytokine activity of lymphocyte subset-populations in a diseased animal (e.g. human), preferably where these lymphocyte subset-2 populations comprise Th1 or Th2 populations. In general, naive $CD4^+$ helper T lymphocytes (Th) develop into functionally mature effector cells upon stimulation with relevant antigenic peptides presented on the major histocompatibility complex (MHC) class II molecules by antigen-presenting cells (APC). Based on the characteristic set of cytokines produced. Th cells are commonly segregated into at least two different subpopulations: Th1 cells producing exclusively interleukin-2 (IL-2), interferon-gamma (IFN-γ) and lymphotoxin, while Th2 cells produce IL-5, IL-5, IL6, IL10 and IL-13. These Th1 and Th2 subsets appear to be extremes in cytokine production profiles and within these polarized subsets, individual Th cells exhibit differential rather than co-ordinated cytokine gene expression. These subsets develop from common Th precursor cells (Thp) after triggering with relevant peptides into Th0 cells producing an array of cytokines, including IL-2, IL-4, IL-5 and IFN-γ. These activated Th0 cells subsequently polarize into the Th1 or Th2 direction based on the cellular and cytokine composition of their microenvironment. Antigen-presenting cells like the various subsets of dendritic cells besides subsets of macrophages largely determine this polarization into Th1 or Th2 subset development. The Th1–TH2 subsets appear to cross-regulate each other's cytokine production profiles, mainly through IFN-γ and IL-10, and from this concept it was rationalized that disturbances in the balance between these two subsets may result in different clinical manifestations (5). IL-12 is a dominant factor promoting Th1 subset polarization and dendritic cells and macrophages produce IL-12. Moreover, IL-12 induces IFN-γ production by T cells and natural killer (NK) cells.

Recently, it was reported that IL-18 acts synergistically with IL-12 to induce Th1 development. Polarization of Th2 cells is critically dependent on the presence of IL-4 produced by T cells or basophils and mast cells. APC-derived IL-6 has also been shown to induce small amounts of IL-4 in developing Th cells. IL-10 and APC-derived prostaglandin $E_2$ ($PGE_2$) inhibit IL-12 production and Th1 priming.

The Th1–Th2 paradigm has been useful in correlating the function of Th1 cells with cell-mediated immunity (inflammatory responses, delayed type hypersensitivity, and cytotoxicity) and Th2 cells with humoral immunity. In general, among infectious diseases, resistance to intracellular bacteria, fungi, and protozoa is linked to mounting a successful Th1 response. Th1 responses can also be linked to pathology, like arthritis, colitis and other inflammatory states. Effective protection against extracellular pathogens, such as helminths, mostly requires a Th2 response, and enhanced humoral immunity may result in successful neutralisation of pathogens by the production of specific antibodies.

In yet another preferred embodiment, the invention provides an immunoregulator capable of modulating dendritic cell differentiation. The selective outgrowth of Th1 vs. Th2 type cells is dependent on the interaction of precursor Th cells with antigen-presenting cells (APC) carrying the relevant peptide in conjunction with their MHC class II molecules. Cytokines released by the APC and present during the initial interaction between dendritic cells and the pertinent T cell receptor carrying T cells drive the differentiation in to Th1 vs. Th2 subsets. Recently, two different precursors for DC (myeloid vs. lymphoid) have been described in man. Selective development of DC1 from myeloid precursors occurs after stimulation with CD40 Ligand or endotoxin, and results in high production of IL-12, Lymhoid precursors give rise to DC2 cells after CD40 Ligand stimulation, and produced IL-1, IL-6 and IL-10. These cytokines are of prime importance in driving the development of the activated Th cell: IL-4 is required for the outgrowth of Th2 type cells which can be greatly enhanced by the presence of IL-10, while selective differentiation to Th1 type cells is exclusively dependent on the presence of IL-12. Since DC1 are characterized by the production of IL-12, they will primarily induce outgrowth of Th1 type cells, while DC2 produce IL-10 and selectively promote Th2 development in the presence of exogenous IL-4. It is shown herein that an IR as provided by the invention is capable of regulating or modulating DC activity and differentiations thereby allowing selective differentiation and activity of Th1 and/or Th2 cells.

In one embodiment, the invention provides an immunoregulator comprising an active component obtainable from a mammalian chorionic gonadotropin preparation said active component capable of stimulating splenocytes obtained from a non-obese diabetes (NOD) mouse, or comprising an active component functionally related to said active compound, for example allowing regulating or modulating DC activity and differentiation, or allowing selective differentiation and activity of Th1 and/or Th2 cells, in case of chronic inflammation, such as diabetes or chronic transplant rejection for example as shown in the detailed description herein wherein said stimulated splenocytes are capable of delaying the onset of diabetes in a NOD-severe-combined-immunodeficient mouse reconstituted with said splenocytes, or wherein said active component is capable of inhibiting gamma-interferon production of splenocytes obtained from a non-obese diabetes (NOD) mouse, or wherein said active component is capable of stimulating interleukine-4 production of splenocytes obtained from a non-obese diabetes (NOD) mouse.

In another embodiment, the invention provides an immunoregulator comprising an active component obtainable from a mammalian chorionic gonadotropin preparation said active component capable of protecting a mouse against a lipopolysaccharide induced septic shock, for example allowing regulating or modulating DC activity and differentiation, or allowing selective differentiation and activity of Th1 and/or Th2 cells, in case of acute inflammation, such as seen with shock or (hyper) acute transplantation rejection, for example as shown in the detailed description herein wherein said active component is capable of reducing ASAT or other relevant plasma enzyme levels after or during organ failure, as commonly seen with shock.

In one embodiment said immunoregulator according to the invention comprises, as further detailed in the detailed description, an active component residing in a fraction which elutes with an apparent molecular weight of 58 to 15 kilodalton as determined in gel-permeation chromatography, where associating, inhibiting or synergistic components are found as well. In another embodiment, the invention provides an immunoregulator, as further detailed in the detailed description, wherein said active component is present in a fraction which elutes with an apparent molecular weight of smaller than kilodalton as determined in gel-permeation chromatography, fore example wherein said active component is present in a fraction which elutes with an apparent molecular weight of <1 kilodalton as determined in gel-permeation chromatography. Although said immunoregulator according to the invention is easily obtained from urine, for example wherein said mammalian chorionic gonadotropin preparation is derived from urine, other sources, such as serum, cells or tissues comprising gonadotropin are applicable as well. Also from said sources an immunoregulator according to the invention capable of for example regulating Th1 and/or Th2 cell activity, and/or capable of modulating dendritic cell differentiation, is provided.

Preferably, an immunoregulator as provided by the invention is obtainable from a pregnant mammal, preferably a human, for example obtainable from a pharmacological preparation prepared to contain (placental) gonadotropins such as pregnant mare scrum gonadotropin (PMSG) found in serum of pregnant mares (IR-S, or pregnant mouse uterus extract (PMUE) extracted from uteri (IR-UE) of gravid mice or human chorionic gonadotropin (hCG or HCG) found in blood or urine of pregnant women. An IR as provided by the invention can be associated with or without gonadotropin as for example present in the urine of first trimester of pregnancy (IR-U) and in commercial hCG preparations (IR-P) has immune regulatory effects. In particular, IR can inhibit or regulate auto-immune and acute- and chronic-inflammatory diseases. TNF and IFN-gamma are pathologically involved in acute inflammatory disease such as sepsis or septic shock and also in auto-immune and chronic inflammatory diseases. Since IR has the ability to regulate T-cell sub-populations and inhibit TNF and IFN-gamma, IR can be used to treat, suppress or prevent immune mediator disorders such sepsis or septic shock (acute inflammatory disease) as well as auto-immune disease or chronic inflammatory diseases such as systemic lupus erythematosus, diabetes, rheumatoid arthritis, post-partum thyroid dysfunction, auto-immune thromocytopenia and others, such as allergies and chronic inflammatory disease (i.e. rheumatic disease, Sjögrens syndrome, multiple sclerosis) and transplantation related immune responses. Our results for example show that IR inhibit sepsis or septic shock caused by endotoxin or by exotoxin. IR as provided by the invention inhibits or counters immune mediated autoimmune diseases, chronic inflamatory diseases as well as acute inflammatory diseases.

The invention provides a pharmaceutical composition for treating an immune-mediated disorder such as an allergy, auto-immune disease, transplantation-related disease or acute or chronic inflammatory disease and/or provides an immunoregulator (IR), for example for stimulating or regulating lymphocyte action comprising an active component said active component capable of stimulating splenocytes obtained from a 20-week-old female non-obese diabetes (NOD) mouse, said stimulated splenocytes delaying the onset of diabetes in a NOD-severe-combined-immunodeficient (NOD.scid) mouse reconstituted at 8 weeks old with said splenocytes, or comprising an active component functionally related thereto.

In one embodiment, the invention provides an pharmaceutical composition or immunoregulator wherein said active component is capable of inhibiting gamma-interferon production or stimulating interleukine-4 production of splenocytes obtained from a 20-week-old female non-obese diabetes (NOD) mouse. Clinical grade preparations of gonadotropins such as hCG and PMSG have since long been used to help treat reproductive failure in situations where follicular growth or stimulation of ovulation is desired. Said preparations are generally obtained from serum or urine, and often vary in degree of purification and relative activity, depending on initial concentration in serum or urine and depending on the various methods of preparation used.

In a particular embodiment, the invention provides a immunoregulator comprising an active component obtainable from a mammalian CG preparation said active component capable of stimulating splenocytes obtained from a non-obese diabetes (NOD) mouse, or comprising an active component functionally related to said active compound, for example wherein said stimulated splenocytes are capable of delaying the onset of diabetes in a NOD-severe-combined-immunodeficient mouse reconstituted with said splenocytes.

The invention also provides an immunoregulator wherein said active component is capable of inhibiting gamma-interferon production obtained from a non-obese diabetes (NOD) mouse. The invention also provides an immunoregulator wherein said active component is capable of stimulating interleukine-4 production of splenocytes obtained from a non-obese diabetes (NOD) mouse.

An immunoregulator as provided by the invention (IR) with or without hCG as for example present in the urine of first trimester of pregnancy (IR-U) and in commercial hCG preparations (IR-P) has immune regulatory effects. In particular. IR can inhibit or regulate auto-immune and acute- and chronic-inflammatory diseases. TNF and IFN-gamma are pathologically involved in acute inflammatory disease such as sepsis or septic shock and also in auto-immune and chronic inflammatory diseases. Since IR has the ability to regulate T-cell sub-populations and inhibit TNF and IFN-gamma, IR can be used to treat, suppress or prevent immune mediator disorders such as sepsis or septic shock (acute inflammatory disease) as well as auto-immune disease or chronic inflammatory diseases such as systemic lupus erythematosus, diabetes, rheumatoid arthritis, post-partum thyroid dysfunction, auto-immune thromocytopenia and others, such as allergies and chronic inflammatory disease (i.e. rheumatic disease, Sjögrens syndrome, multiple sclerosis) and transplantation related immune responses. Our results for example show that IR inhibit sepsis or septic shock caused by endotoxin or by exotoxin. IR as provided by the invention inhibits or counters immune mediated auto-immune diseases, chronic inflammatory diseases as well as acute inflammatory diseases.

Anecdotal observations and laboratory studies indicated previously that hCG might have an anti-Kaposi's sarcoma and anti-human-immunodeficiency-virus effect (Treatment Issues, July/August 1995, page 15. It has been observed that hCG preparations have a direct apoptotic (cytotoxic) effect on Kaposi's sarcoma (KS) in vitro and in immunodeficient patients and mice and a prohematopoetic effect on immunodeficient patients (Lunardi-Iskandar et al., Nature 375, 64–68; Gill et al., New. Eng. J. Red. 335, 1261–1269, 1996; U.S. Pat. No. 5,677,275), and a direct inhibitory antiviral effect on human and simian immunodeficiency virus (HIV and SIV) (Lunardi-Iskandar at al., Nature Med. 4, 428–434, 1998, U.S. Pat. No. 5,700,781). Said cytotoxic and anti-viral effects have also been attributed to an unknown hCG mediated factor (HAF), present in clinical grade preparations of hCG. However, commercial hCG preparations (such as CG-10, Steris Profasi, Pregnyl, Choragon, Serono Profasi, APL), have various effects. Analysis of several of these, (AIDS, 11: 1333–1340, 1997) for example shows that only some (such as CG-10, Steris Profasi) are KS-killing whereas others (Pregnyl, Choragon, Serono Profasi) were not. Secondly, recombinant subunits of ($\alpha$ or $\beta$) hCG were killing but intact recombinant hCH not. It was also found that the killing effect was also seen with lymphocytes. Therapy of KS has recently been directed at using beta-hCG for its anti-tumour effect Eur. J. Med Res. 21: 155–158, 1997, and it was reported that the beta-core fragment isolated from urine had che highest apoptotic activity on KS cells (AIDS, 11: ,713–721, 1997). Recently, Gallo et. al. reported anti-Kaposi's Sarcoma, anti-HIV, anti-SIV and distinct hematopoietic effects of clinical grade crude preparations of human chorionic gonadotropin (hCG) (Lunardi-Iskandar et al. 1995, Gill et al. 1996, Lunardi-Iskandar et al. 1998). In contrast to their previous studies, it is also claimed that the anti-tumour and anti-viral activity of hCG preparation is not due to the native hCG heterodimer, including its purified subunits or its major degradation product, the $\beta$-core; instead the active moiety resides in an as yet unidentified hCG mediated factor (HAF). Whatever the true factor may be, these unidentified factors in several hCg preparations have anti-tumour activity through the selective induction of apoptosis, besides direct cytotoxic effects on the tumour cells. Furthermore, they postulated that the anti-tumour activity could not be due to an immune-mediated response, since there was no infiltration of the tumour with mononuclear cells.

Moreover, the reported pro-hematopoietic effect of clinical grade hCG was noted in clinical studies in humans infected with HIV, (Lunardi-Iskandar et al. 1998) indicating that the hematopoietic effect is indirect, and caused by rescuing CD4+ cells otherwise killed by HIV through the anti-HIV activity of hCG.

The invention provides an immunoregulator or a pharmaceutical composition for treating an immune-mediated disorder obtainable from a hCG preparation or a fraction derived thereof. The effects of said immunoregulator include a stimulating effect on lymphocyte populations (such as found in peripheral lymphocytes, thymocytes or splenocytes), instead of cytotoxic or anti-viral effects. The invention provides a method for treating an immune-mediated-disorder comprising subjecting an animal to treatment with at least one immunoregulator obtainable from a pregnant mammal. Said treatment can be direct, for example treatment can comprise providing said individual with a pharmaceutical composition, such as a hCG or PMSG preparation, comprising an immunoregulator as provided by the invention. It is also possible to provide said pharmaceutical composition with a fraction or fractions derived from a pregnant animal by for example sampling urine or serum or placental (be it of maternal or foetal origin) or other tissue or cells and preparing said immunoregulator comprising said active component from said urine or serum or tissue or cells by fractionation techniques known in the art (for example by gel permeation chromatograpy) and testing for its active component by stimulating a NOD mouse or its splenocytes as described. In particular, said preparation or component is preferably derived from a pregnant animal since an embryo has to survive a potentially fatal immunological conflict with its mother: developing as an essentially foreign tissue within the womb without triggering a hostile immune attack. So, to prevent this rejection "allograft" the immunoligical interaction between mother and fetus has to be suppressed, either for instance through lack of fetal-antigen presentation to maternal lymphocytes, or through functional "suppression" of the maternal lymphocytes. If fetal antigens are presented, maternal immune responses would be biased to the less damaging, antibody-mediated T helper 2 (Th2)-type. This would suggest that pregnant women are susceptible to overwhelming infection, which is not the case. Female individuals during pregnancy maintain or even increase their resistance to infection. Moreover, while said individuals normally are more susceptible to immune diseases than male individuals, especially autoimmune diseases, during pregnancy they are more resistant to these diseases.

The invention also provides a method for in vitro stimulation of lymphocytes and transferring said stimulated lymphocytes as a pharmaceutical composition to an animal for treating said animal for an immune mediated disorder. In a particular embodiment of the invention a pharmaceutical composition is provided comprising lymphocytes stimulated in vitro with an immunoregulator provided by the invention.

In a preferred embodiment of the invention, said disorder comprises diabetes, yet other immune mediated disorders, such as acute and chronic inflammation, can also be treated. In yet another preferred embodiment, said disorder comprises sepsis or septic shock. The invention provides a method of treatment for an animal, preferably wherein said animal is human.

In a particular embodiment, a method provided by the invention is further comprising regulating relative ratios and/or cytokine activity or cytokine expression or marker expression of lymphocyte subset-populations in said animal, such as subset-populations that comprise Th1 or Th2 cells, or Th3 or Th8 cells, or other effector or regulatory T-cell populations.

The invention also provides an immunoregulator for use in a method according to the invention, and use of said immunoregulator, preferably obtainable from a pregnant mammal, for the production of a pharmaceutical composition for the treatment of an immune-mediated-disorder, preferably selected from a group consisting of allergies, auto-immune disease (such as systemic lupus erythematosus or rheumatoid arthritis), transplantation-related disease and acute (such as septic or anaphylactic shock or acute or hyper acute transplant rejection) and chronic inflammatory disease (such as atherosclerose, diabetes, multiple sclerosis or chronic transplant rejection). Furthermore, the invention provides a use according to the invention wherein said immune-mediated disorder comprises allergy, such as asthma or parasitic disease, or use according to the invention wherein said immune-mediated disorder comprises an overly strong immune response directed against an infectious agent, such as a virus or bacterium. Often in most of those diseases production of autoreactive antibodies and/or autoreactive T lymphocytes can be found mounting or being part of a too strong immune response. This is for example seen with parasitic disease, where IgE production is overly strong or which disease is Th2 dependent, and detrimental for the organism, but also with (myco)bacterial infections such as TBC or leprosy. An autoimmune response may also occur as manifestation of viral or bacterial infection and may result in severe tissue damage, for example destructive hepatitis because of Hepatitis B virus infection, or as seen with lymphocytic choriomeningitis virus (LCMV) infections. Said overly strong immune response is kept at bay with an immunoregulator as provided by the invention. Yet other use as provided by the invention relates to treatment of vascular disease, whereby radical damage (damage caused by radicals) to cells and tissue is prevented or repaired by treatment with IR according to the invention; whereby IR also acts as anti-oxidant directly or indirectly. For example, a determining event in the pathogenesis of diabetes I is the destruction of insulin-producing pancreatic beta cells. There is strong evidence that the progressive reduction of the beta-cell mass is the result of a chronic autoimmune reaction. During this process, islet-infiltrating immune cells. Islet capillary endothelial cells and the beta cell itself are able to release cytotoxic mediators. Cytokines, and in particular nitric oxide (NO), are potent beta-cell toxic effector molecules. The reactive radical NO mediates its deleterious effect mainly through the induction of widespread DNA strand breaks, other radicals, such as oxygen, through their effects on lymfocyte sub-populations such as Th1 and Th2 cells. This initial damage triggers a chain of events terminating in the death of the beta cell and disarray of the immune response.

Furthermore, an immunoregulator according to the invention is capable of regulating radical induced or directed cell-cell interactions or cell responses, specifically those interactions or responses of an immunological nature, e.g. related to regulating interactions of the innate or adaptive immune system. Not wishing to be bound by theory, there are two arms of the immune system: the innate (non-specific) and adaptive (specific) systems, both of which have cellular and humoral components. Examples of cellular components of the innate immune system are monocytes, macrophages, granulocytes, NK cells, mast cells, gd T cell etc, while, examples of humoral components are lysozyme, complement acute phase proteins and mannose-binding lectin (MBL). The major cellular components of the adaptive immune system are T and B cells, while examples of humoral components are antibodies. The adaptive system has been studied most because of its specificity, effectiveness at eliminating infection and exclusive presence in higher multicellular organisms. The innate system is often considered primitive and thought to be 'unsophisticated'. However, the innate system not only persists but could also play a critical role in one of the most fundamental immune challenges—viviparity. The innate system instigates an immune response by processing and presenting antigen in association with major histocompatibility complex (MHC) class I and II molecules to lymphocytes. Full response often requires adjuvant (such as endotoxin), which, through interaction with the innate immune system, produce costimulatory surface molecules or cytokines. This determines the biological significance of antigens and communicates this information to the adaptive system. So it instructs the adaptive system to either respond or not. So these two great arms of immune system not only influence each other but also regulate each other at least at the cellular level through for example cytokines and co-stimulator % molecules etc.

There are many physiological conditions and immune pathologies where these two systems are involved separately or in combination. For example, it has been shown that in pregnancy the maternal innate immune system is more stimulated, or for it has been proposed that type II diabetes mellitus is a disease of a chronic hyperactive innate immune system. Another example is the involvement of the innate immune system in listeriosis. Dysregulation in the adaptive immune system may also lead to immune diseases like systemic or organ-specific autoimmunity, allergy, asthma etc, but it can also play a role in the maintenance of pregnancy and in the prevention of "allograft" rejection.

As mentioned above, the adaptive system has been studied most because of its specificity, effectiveness at eliminating infection, and exclusive presence in higher multicellular organisms. Its regulation has also been studied most. For example, it well known that the cytokine micro-environment plays a key role in T helper cell differentiation toward the Th1 or Th2 cell type during immune responses. IL-12 induces Th1 differentiation, whereas IL-4 drives Th2 differentiation. Recently it has also been shown that subsets of dendritic cells (DC1, DC2) provide different cytokine microenvironments that determine the differentiation of either Th1 or Th2 cells. In addition, negative feedback loops from mature T helper cell responses also regulate the survival of the appropriate dendritic cell subset and thereby selectively inhibit prolonged Th1 or Th2 responses. Moreover, development of Th1 responses can be antagonized directly by IL-4 and indirectly by IL-10, which inhibits the production of IL-12 and interferon-g-inducing factor (IGIF) by macrophages stimulated by the innate immune response. Th2 cells dependent on IL-4 to proliferate and differentiate have been implicated in allergic and atopic manifestations, and in addition through their production of IL-4 and IL-10, have been suggested to play a role in tolerance. Specifically, it has been suggested that Th1 to Th2 switch may prevent the development of organ-specific autoimmune pathologies and required for the maintance of pregnancy. Recently it has become clear that distinct subsets of regulatory T cells are responsible for regulating both Th1 and Th2 responses and prevent the development of immune pathologies. One of the common features of many of these regulatory T cells is that their function is at least in part due the action of TGF-beta; this would be in keeping with the ability of TGF-beta to inhibit both Th1 and Th2 development while IL-10 could preferentially inhibit Th1 alone.

The selective outgrowth of Th1 vs. Th2 type cells is dependent on the interaction of precursor Th cells with antigen-presenting cells (APC) carrying the relevant peptide in conjunction with their MHC class II molecules. Cytokines released by the APC and present during the initial interaction between dendritic cells and the pertinent T cell receptor carrying T cells drive the differentiation in to Th1 vs. Th2 subsets. Recently, two different precursors for DC (myeloid vs. lymphoid) have been described in man. Selective development of DC1 from myeloid precursors occurs after stimulation with CD40Ligand or endotoxin, and results in high production of IL-12. Lymhoid precursors give rise to DC2 cells after CD40Ligand stimulation, and produced IL-1, IL-6 and IL-10. These cytokines are of prime importance in driving the development of the activated Th cell: IL-4 is required for the outgrowth of Th2 type cells which can be greatly enhanced by the presence of IL-10, while selective differentiation to Th1 type cells is exclusively dependent on the presence of IL-12. Since DC1 are characterized by the production of IL-12, they will primarily induce outgrowth of Th1 type cells, while DC2 produce IL-10 and selectively promote Th2 development in the presence of exogenous IL-4.

In a particular embodiment said immunoregulator comprises a clinical grade hCG or PMSG preparation or a fraction derived thereof. For example, the invention provides use of a hCG preparation, or a preparation functionally equivalent thereto, for the preparation of a pharmaceutical composition for the treatment of diabetes. In yet another example, the invention provides use of a hCG preparation, or a preparation functionally equivalent thereto, for the preparation of a pharmaceutical composition for the treatment or prevention of sepsis or septic shock. For example, the invention provides a use according to the invention wherein said treatment comprises regulating relative ratios and/or cytokine activity of lymphocyte subset-populations, for example Th1 and/or Th2 cells in a treated individual.

The invention furthermore provides a method for selecting an immunoregulator comprising determining therapeutic effect of an candidate immunoregulator fraction. By way of example such a method is given wherein by subjecting an animal prone to show signs of diabetes, such as an NOD mouse, useful as experimental model, to a urine fraction or fraction derived thereof, and subsequently determining the development of diabetes in said animal, one such an immunoregulator fraction or active component therein is selected or identified. In yet another embodiment, the invention provides a method for selecting an immunoregulator comprising determining therapeutic effect of an immunoregulator by subjecting an animal prone to show signs of septic shock, such as a mouse experiencing an effect of LPS or other toxine, to a urine fraction or fraction derived thereof determining the development of septic shock in said animal. Preferable, a method according to the invention is preferred wherein said therapeutic effect is further measured by determining relative ratios and/or cytokine activity of lymphocyte subset-populations in said animal, or wherein said therapeutic effect is further measured by determining enzyme levels in said animal, or by measuring other clinical parameters known in the art, as for example shown in the detailed description herein.

Not wishing to be bound by theory, our results show that IR as provided by the invention is able to regulate the Th1/Th2 balance in vivo (BALD/c, NOD) and in vitro. In dominant Th1 phenotype models like NOD, IR (like IR-P nd its fractions) amongst others down-regulates the IFN-gamma production (in vivo/in vitro) and promote the IL-10 and TGF-beta production, in contrast to IL-4 production, which indicates the induction of regulatory cells like Th3 and Tr1 by IR. These regulatory cells may play role in the therapeutic effects of IR in immune and inflammatory diseases and immune tolerance. We have also shown that IR and its fractions are able to inhibit the production of IFN-gamma in vitro and in vivo execept for the fraction IR-P3 and rhCG that separatly show no to moderate inhibition of the IFN-gamma production. The combination of IR-P3 and rhCG gives a stronger inhibition of the IFN-gamma. This implies the need of IR-P3 for rhCG for its at least its IFN-gamma inhibition in these models. This implies also to the anti-CD3 stimulated spleen cells obtained from in vivo treated NOD mice and also to polarisation of T-helper cell to Th2 phenotype.

Moreover, IR-P, its fractions (IR-P1, IR-P2, IR-P3) and IR-P3 in combination with rhCG are all able to inhibit the class switch of B cells to IgG2a, while IR-P2 and rhCG give no to moderate inhibition. Our results on IFN-gamma production and proliferation showed that IR-P3 alone did not have the maximum effect as compare to IR-P whereas for IgG2a inhibition we see that IR-P3 does not need rhCG to give the maximum results. However the increase in production of IL-10 under the influence of IR-P3 is less than for IR-P1. This suggests that for maximum production of IL-10, hCG, a breakdown product thereof, or a yet unknown sub-fraction in IR-P1 in combination with IR-P3 is needed. Because IR-P3 alone is already able to promote IL-10 production, it does not need any other fraction or component to inhibit the production of IgG2a.

We have also shown that IR as provided by the invention is able to inhibit the IFN-gamma production and the promotion of IL-10, TGF-beta, IL-4 and IL-6 in the BALB/c animal model (in vitro as well as ex vivo). So, it is clear that at least these cytokines are involved in the regulation of immune responses by IR and in the induction of regulatory cells. Remarkably, IR promotes the proliferation of anti-CD3 stimulated spleen cells (ex vivo) in BALB/c mice in contrast to NOD. This might reflect the difference in NOD which is an autoimmune disease model and BALB/c which is a animal model without distinct immunopathology. In both animal model (NOD/BALB/c) IR promote LPS stiumlated proliferation of spleens (in vitro and ex vivo).

Our DC experiments with NOD and BALB/c mice show that IR not just regulates T cell responses, but can also regulate DC maturation and function. DC that function as professional antigen processing cells (APC) an play important role in immune tolerance. Treatment of C57B/6 DC with IR in allo-MLR is able to down-regulate T cell proliferation. This shows that IR can also facilitate the induction of a state of tolerance. On the basis of these data we performed MHC and non-MHC incompatible skin (C57BL/6) transplantation tp recipients (BALB/c) treated with IR. Our data showed that in the control group the allograft (skin) was completely rejected within 15 days, while skin graft of recipient mice treated with IR three times was rejected after 21 days. So, IR is able to delay graft rejection. IR as provided by the invention is able to inhibit the immunopathology in numerous animal models for immune diseases. IR inhibits the immunopathology and clinical symptoms in the NOD model (for diabetes), and the EAE model (for MS), inhibits allograft rejection, and delays SZT-induced diabetes. Our data also shows that IR has effects on different cell populations. IR effects T cells and thereby regulates Th1/Th2 balance and induce regulatory cells that in turn not just only regulate T cells but also have effects on the APC compartment. In addition, IR can regulate the APC compartment directly and can influence the innate and adaptive immune responses. By doing so, IR not just can influence diseases caused by disbalance of the adative immune system, but can also influence the diseases due the disbalance of the innate immune system or of both systems. For example, the role of cytokines and the innate immune system in the aetiology of Type II diabetes is likely important. Recently is has been suggested that unknown factors like age and overnutrition in genetically or otherwise predisposed subjects, cause increased secretion of cytokines from cells such as macrophages and further cytokines scretion from atherosclerotic plaques. The acute-phase response. Induced by cytokines includes a characteristic dyslipdaemia (raised VLDL triglyceride and lowered HDL cholesterol) and other risk factors for atherosclerosis, such as fibrinogen. Cytokines also act on the pancreatic beta cell (contributing to impaired insulin secretion), on adipose tissue (stimulating leptin release) and on the brain, stimulating corticotropin-releasing hormone, ACTH and thus cortisol secretion. The latter may contribute to central obesity, hypertension and insulin resistance. A further cause of insulin resistance is the cytokine TNF-alpha, which inhibits the tyrosine kinase activity of the insulin receptor. Type II diabetic patients without microvascular or macrovascular complications have a high acute-phase response but tissue complications do further increase stress reactants in Type II diabetes. In non-diabetic subjects with atherosclerosis, a 'haematological stress syndrome' has been recognised for many years, consisting of high acute-phase reactants such as fibrinogen, increased blood viscosity and increased platelet number and activity. Cytokines produced by endothelium, smooth muscle cells and macrophages of the atherosclerotic plaque could contribute to this acute-phase response seen in atherosclerosis. Apart from the acute-phase proteins which are established or putative risk factors for cardiovascular disease such as fibrinogen, serum amyloid A, PAI-1, Lp(a) lipoprotein and VLDL triglyceride, proinflammatory cytokines produced at the sites of diabetic complications or by the diabetic process itself may also exacerbate atherosclerosis by acting on the endothelium, smooth muscle cells and macrophages. Thus, likely there is positive feedback involving cytokines and atherosclerosis, perhaps accounting for the acceleration of arterial disease in diabetes. The plaque produces cytokines, which further exacerbate the process of atherosclerosis locally but also cause an increase in circulating acute-phase proteins, many of which are themselves risk factors for atherosclerosis.

Shortly, cytokines and the innate immune system play a central role in the pathophysiology of Type II diabetes and atherosclerosis. Since IR has the ability to regulate such response, it is also benefical to type II diabetes and atherosclerosis and its complications. In addition, IR can delay the induction of disease such as diabetes in the HD-STZ model where reactive oxygen species (ROS) play an important role, so IR can also act as anti-oxidant directly or indirectly, and also for that reason is beneficial in the treatment and prevention of diabetes and related diseases. Furthermore, the invention provides an immunoregulator selected by a method according to the invention, a pharmaceutical composition comprising such a selected immunoregulator, and the use of said for the preparation of a pharmaceutical composition for the treatment of an immune-mediated disorder. Fractions containing bioactive IR are purified to homogeneity by liquid chromatography. The direct analysis by mass spectrometry combined with database screening, using MALDI-TOF (matrix assisted laser mass desorption/ionization-time of flight), permits the characterization of IR or fractions thereof in multi-molecular complexes. Nuclear magnetic resonance spectroscopy provides information on the types of bonding to the hydrogen atoms in the IR and the molecular structure of the IR. Infrared and near-ultraviolet spectroscopy aids in structural determination of the IR. MALDI-TOF and NMR analysis complements separation if needed, and subsequent sequencing and synthesis of the bioactive IR. Chemical mutagenesis is employed to mutate the chemical composition of IR, permitting fine mapping of the interaction site with the receptor/acceptor by jo performing qualitative and quantitative binding analysis in appropriate detection systems like a biosensor system.

Derivatives of IR by chemical en genetic modification are again tested for bioactivity in above methods or assays demonstrating activity of IR or IR containing mixtures. Furthermore, the present invention provides verification of the presence of a receptor of IR. Various fractions of (pregnancy) urine, commercial hCG preparations or fragments thereof, and recombinant hCG or fragments thereof arespiked with known amounts of IR. The mixtures are analyzed by gel permeation chromatography and compared to the mentioned samples without spiked IR and free IR. Shifts in IR peak(s) to higher molecular weight fractions indicates the presence of a receptor/acceptor. Analyzing the fractions for IR activity (after IR has been displaced from the receptor/acceptor) validates this elution profile containing the shifted IR peaks. From the fraction containing the shifted IR activity, the receptor/acceptor is purified by liquid chromatography and validated for IR function by displacement. The IR is, in addition iodinated and spiked to fractions of first trimester pregnancy urine, commercial hCG preparations or fragments thereof, and recombinant hCG or fragments thereof and the mixtures are evaluated in appropriate detection systems like SOS-PAGE (sodium dodecyl sulfate—polyacrylamide gel electrophoresis) under reducing and non-reducing conditions. Blots of such gels are analysed by systems like quantitative phosphorimaging analysis using STORM technology. IR is immobilized to e.g. Affigel by the use of a chemical linker or carrier protein permitting the isolation of binding moieties by means of affinity chromatography. Subsequent elution provides purified receptor/acceptor molecules. The receptor/acceptor isolated from extracellular and intracellular sources in soluble or in membrane-bound form are immobilized to an activated biosensor surface. The IR in various concentrations will then probe this sensor surface and from the resulting binding profiles the association rate and dissociation rate constants are determined and the affinity constant are calculated. By probing with different mixtures of IR and receptors/acceptors epitope mapping is evaluated to obtain information on the nature of binding epitope. IR is labeled (e.g. fluorescent and radioactively) to permit detection of IR receptors in membrane bound form to assess cellular expression and tissue distribution under non-diseased states and during the various immune and related disorders pertinent to the activity of IR. Using labeled IR and having available purified receptor, monoclonal antibodies and other specific reagents are generated allowing the design of a quantitative immuno-assay for the measurement of soluble IR receptors. Recombinant DNA technology is used to generate IR producing prokaryotic and eukaryotic expression systems. Site-directed mutagenesis is used to produce IR variants with altered binding profiles permitting the fine identification of the interaction site with the receptor/acceptor. Upon the cloning of the gene, transgenic mice with constitutive and inducible expression of the IR as well as IR gene deficient mice are generated permitting the entry into the field of biotechnology and gene therapy.

Purified IR is used to produce monoclonal antibodies and/or other specific reagents thereby facilitating the design of an IR-specific quantitative immuno-assay. Also single chain $F_v$ fragments are isolated by using the phage display technology with the use of a phage library containing a repertoire comprising a vast number of different specificities.

The invention is further explained in the detailed description without limiting the invention thereto.

DETAILED DESCRIPTION

Immunoregulator (IR)

Ir-U Purification from First Trimester Pregnancy Urine (Method 1):

First trimester pregnancy urine (2 liters) was collected in a bottle from a healthy volunteer and was refrigerated until delivered at the laboratory within 2 days. Upon delivery, 1 gram per liter of sodium azide was added and the pH was adjusted to 7.2–7.4 with sodium hydroxide and allowed to sediment for 1 hour (h) at room temperature (RT). Approximately, 75% of the supernatant was decanted and the remainder close to the precipitate was centrifuged (10 min at 25000 rpm at 40C) to remove sediment and added to the rest of the supernatants. The supernatants was filtered through 0.45 (m in a Minitan (Millipore) transversal filtration set-up. Subsequently, the filtrate (2 liter) was concentrated in an Amicon ultrafiltration set-up equipped with an YM Diopore membrane with a 10 kDa cut-off. The final volume (250 ml) was dialysed against 2 changes of 10 liters of Milli Q water. Next the sample was further concentrated by 10 kDa cut-off in an Amicon ultrafiltration to a final volume of 3 ml.

Gel permeation: A Pharmacia FPLC system equipped with a Superdex 75 gel permeation column was used to analyze the treated urine sample (IR-U) and commercial hCG preparation (IR-P) (Pregnyl; Organon; Oss, NL). The running conditions are shown elsewhere in this document:

IR-U Purification from first Trimester Pregnancy Urine Method 2:

In order to purify lower molecular weight fractions from first trimester pregnancy urine, 50 ml of urine was directly desalted with a FPLC system equipped with a FDCΘG25 in 50 mM ammonium bicarbonate. The running conditions used are shown below:

| | | |
|---|---|---|
| 0.0 | CONC % B | 0.0 |
| 0.0 | ML/MIN | 0.50 |
| 0.1 | ML/MIN | 1.00 |
| 0.2 | ML/MIN | 2.00 |
| 0.3 | ML/MIN | 3.00 |
| 0.4 | ML/MIN | 4.00 |
| 0.5 | ML/MIN | 5.00 |
| 0.5 | CM/MIN | 1.00 |
| 1.5 | VALVE.POS | 1.2 |
| 1.5 | CLEAR DATA | |
| 1.5 | MONITOR | 1 |
| 1.5 | LEVEL % | 2.0 |
| 1.5 | MIN/MARK | 2.0 |
| 1.5 | INTEGRATE | 1 |
| 1.8 | VALVE.POS | 1.1 |
| 2.3 | PORT.SET | 6.1 |
| 6.6 | FEED TUBE | |
| 10.8 | PORT.SET | 6.0 |
| 10.8 | INTEGRATE | 0 |
| 10.8 | FEED TUBE | |
| 12.8 | CONC % B | 0.0 |

IR-U Purification from first Trimester Pregnancy Urine Method 3;

To analyse the IR-U (first trimester urine) obtained from method 1 and 2, we also used Shimadzu HPLC sytem equipped with Alltech macrosphere size exclusion (GPC) column 60 Å or 300 Å (250×4.6 mm) in 50 mM ammonium bicarbonate. The seperation range for both columns were 28,000–250 and 1,200,000–7,500 Dalton, respectively. Sample load volume was 10–50 ml. The flow rate was 0.3 ml/min for 25 minutes. External molecular weight standards were also employed to calibrate the column elution positions. The markers used were: aprotinin (6,500 Da), cytochrome C (12,4001, carbonic anhydrase (29,000), albumin (66,000) and blue dextran (2,000,000).

To analyse IR further two different hCG preparations, IR-P (Pregnyl; Organon; OSS, The Netherlands) and IR-A (APL; Weyth Ayerst; Philadelphia, USA) were used. IR-P was further separated by two methods. A Pharmacia FPLC system 1 equipped with a Superdex 75 gel permeation column (HR 5/30) (Pharmacia, Sweden) was used to analyse the IR-P. For the running buffer 50 mM ammonium bicarbonate was used. The separation range of this column was 100,000–3,000 Da for globular proteins. Sample load volume was 1 ml and the flow rate was 0.5 ml/min for 45 min. In addition Macrosphere GPC 60 Å (250×4.6 mm) was also used. This column separates proteins, peptides, and other water soluble macromolecules by size exclusion chromatography. The separation range of this column was 28,000–250 Dalton. Three selected areas were fractionated, IR-P1 which elutes apparently with molecular weight of >10 kDa, IR-P2 which elutes apparent with molecular weight between the 10 kDa–1 kDa, and IR-P3 which elutes apparent with molecular weight <1 kDa.

Purification of IR from Lower Molecular Fraction First Trimester Pregnancy Urine (IR-U/LMDF) and Commercial hCG Preparations (Pregnyl, APL): Method 4:

Procedure: The lyophilized low molecular mass fraction (<2 Kda) obtained from first trimester pregnancy urine and from commercial hCG preparations (Pregnyl, APL) by method 3 were further analysed by gel filtration chromatography on a Bio-Gel P-2 column (96×1.5 cm). Fraction (13–17 mg) was suspended in bidistilled water (8–12 ml). The material was not completely dissolved. The sediment (8–11 mg) was separated from the supernatant by centrifugation (sigma 201, 10 min, 3000 rpm). The supernatant (6–8 ml) was fractionated by gel filtration chromatography on a Bio-Gel P-2 column. The column was eluted with water at a flow rate of 15 ml/min. The elution was monitored with an LKB 2142 differential refractometer and an LKB 2238 Uvicord SII (206 nm). Fractions (20 min) were collected by a Pharmacia Frac 100 fraction collecter. Definite fractions were pooled and lyophilized. These fractions were further tested for anti-shock activity.

Gel permeation: A Pharmacia FPLC system equipped with a Superdex 75 gel permeation column was used to analyse the treated urine sample (IR-U) and commercial hCG preparation (IR-P) (Pregnyl, Organon; Oss, NL). The running conditions used are shown below:

| 0.0 | CONC % B | 0.0 |
|---|---|---|
| 0.0 | ML/MIN | 0.20 |
| 0.5 | ML/MIN | 0.50 |
| 0.5 | CM/ML | 0.50 |
| 0.8 | ML/MIN | 1.00 |
| 0.8 | CM/ML | 1.00 |
| 2.0 | CLEAR DATA | |
| | HOLD | |
| 2.0 | VALVE.POS | 1.2 |
| 2.0 | MONITOR | 1 |
| 2.0 | LEVEL % | 5.0 |
| 2.0 | ML/MARK | 2.0 |
| 2.0 | INTEGRATE | 1 |
| 4.0 | VALVE.POS | 1.1 |
| 6.0 | PORT.SET | 6.1 |
| 50.0 | INTEGRATE | 0 |
| 52.0 | CONC % B | 0.0 |

Anion exchange chromatography: In order to further separate the overlapping fractions, 1 ml MONO Q HR 5/5 FPLC anion exchange column was used. The running conditions are shown below and the buffer combination consisted of 10 mM PBS, pH 7.3 as buffer A and PBS containing 1 M NaCl as buffer B:

| 0.0 | CONC % B | 0.0 |
|---|---|---|
| 0.0 | ML/MIN | 1.00 |
| 0.0 | CM/ML | 1.00 |

-continued

| 1.0 | ALARM | 0.1 |
|---|---|---|
| 1.0 | HOLD | |
| 1.0 | CLEAR DATA | |
| 1.0 | MONITOR | 1 |
| 1.0 | LEVEL % | 5.0 |
| 1.0 | ML/MARK | 2.0 |
| 1.0 | INTEGRATE | 1 |
| 1.0 | PORT.SET | 6.0 |
| 1.0 | VALVE.POS | 1.2 |
| 6.0 | CONC % B | 0.0 |
| 6.0 | PORT.SET | 6.0 |
| 11.0 | CONC % B | 50.0 |
| 14.0 | CONC % B | 50.0 |
| 16.0 | CONC % B | 100 |
| 16.0 | PORT.SET | 6.0 |
| 18.0 | CONC % B | 100 |
| 18.0 | CONC % B | 0.0 |
| 18.0 | INTEGRATE | 0 |
| 25.0 | CONC % B | 0.0 |

Further treatment of the IR-U and IR-P: To reduce covalent binding between protein species present in the urine sample, we treated the urine (IR-U) and hCG preparation (IR-P) sample with 60 mm 2-mercaptoethanol for 3 min at 100° C. Subsequently, the treated IR-U and IR-P sample were applied to the Superdex 75 column under identical running conditions.

Activity determination of FPLC fractions of IR-U: The protein concentration of urine fractions was determined by OD280 nm divided by 1.4. From this value, the amount of hCG units was calculated using 5000 IU/ml Pregnyl preparation of hCG corresponded to 100 µg.

Alternative methods for purifying and/or isolating IR comprise gelfiltration on for example a Superdex 75 column in a FPLC system using PBS with or without ethanol to increase resolution and disrupt hydrophobic interactions, optionally followed by cationic exchange. Samples can be submitted in reduced or unreduced form. Another method comprises lectin affinity chromatography to better separate carbohydrate containing components from other components, whereby the effluent is further subjected to gel filtration. It is of course possible to derive at synthetic or recombinant (poly)peptide sequences with methods known in the art, and to select (synthetic) antibodies, i.e. phage-derived, to further select IR.

Auto-immune Disease Experiments

The non-obese diabetic (NOD) mouse is a model for auto-immune disease, in this case insulin-dependent diabetes mellitus (IDDM), which main clinical feature is elevated blood glucose levels (hyperglycemia). The elevated blood glucose levels are caused by the immune-mediated destruction of insulin-producing β cells in the islets of Langerhans of the pancreas (Bach et al. 1991, Atkinson et al. 1994). This destruction is accompanied by a massive cellular infiltration surrounding and penetrating of the islets (insulitis) by a heterogeneous mixture composed of a CD4+ and CD8+ T lymphocytes, B lymphocytes, macrophages and dendritic cells (O'Reilly et al. 1991). The easiest and most reliable way to detect the onset of diabetes in these mice is to test for glucose levels in the blood.

The NOD mouse represents a model in which auto-immunity against beta-cells is the primary event in the development of IDDM. In general, T lymphocytes play a pivotal role in initiating the disease process [Sempe et al. 1991, Miyazaki et al. 1985, Harada et al. 1986, Makino et al, 1986). Diabetogenesis is mediated through a multifactorial interaction between a unique MHC class II gene and multiple, unlinked, genetic loci as in the human disease.

Moreover, the NOD mouse demonstrates beautifully the critical interaction between heredity and environment. Differences between the cleanliness of the housing conditions illustrates how environmental factors can effect the action of diabetes-mediated genes (Elias et al. 1994).

As for the auto-immunity recorded in NOD mice, most antigen-specific antibodies and T-cell responses have been studied after these antigens were detected as self-antigens in diabetic patients. Understanding the role that these auto-antigens play in NOD diabetes may allow to distinguish between primary pathogenic auto-antigens and auto-immunity that is an epiphenomenon. Moreover, one should bear in mind that IDDM patients are genetically and pathogenically heterogeneous.

A typical longitudinal histological examination of the NOD pancreas demonstrates infiltrating cells surrounding the blood vessels at 3–4 weeks of age, but the islets are typically still clear at 6–7 weeks. Infiltrating cells than reach the islets, either surrounding them or accumulating at one pole. Between 10 and 12 weeks, the infiltrating cells penetrate into the islets and the islets become swollen with lymphocytes. As mentioned above, differences between the housing conditions and microbiological and environmental factors can effect the penetrance of diabetes-susceptible genes.

In our hands, typically between 14–17 weeks NOD mice become diabetic. However, this varies from lab to lab (average 14–19 weeks) (Elias et al. 1994). CD4+ T-cells can be separated into at least two major subsets Th1 and Th2. Activated Th1 cells secrete IFN-$\gamma$ and TNF-$\alpha$, while Th2 cells produce IL-4, IL-5 and IL-10. Th1 cells are critically involved in the generation of effective cellular immunity, whereas Th2 cells are instrumental in the generation of humoral and mucosal immunity and allergy, including the activation of eosinophils and mast cells and the production of IgE (Abbas et al. 1996). A number of studies have now correlated diabetes in mice and human with Th1 phenotype development (Liblau et al. 1995, Katz et al. 1995).

Th2 T cells are shown to be relatively innocuous. Some have even speculated that Th2 T cells in fact, may be protective. But Katz et al. have shown the ability of CD4+ T cells to transfer diabetes to naïve recipients resided not with the antigen specificity recognised by the TCR, per se, but with the phenotypic nature of the T cell response. Strongly polarised Th1 T cells transferred disease into NOD neonatal mice, while Th2 T cells did not, despite being activated and bearing the same TCR as the diabetogenic Th1 T cell population. Moreover, upon co-transfer, Th2 T cells could not ameliorate Th1-induced diabetes, even when Th2 cells were co-transferred in 10-fold excess (Pakala et al. 1997).

Th1-polarized T cells can transfer disease in neonatal NOD mice, something Th2-polarized T cells fail to do, both Th1- and Th2-polarized T cells can transfer disease in NOD.scid mice and other immune-compromised recipients. Th2-mediated diabetes in NOD.scid recipients exhibited a longer pre-diabetic phase and a lowered over-all incidence. Moreover, the diabetic lesion created by Th2 cells is unique and quite unlike the lesion found in spontaneously diabetic or Th1 T cell-induced diabetes in either neonates or NOD.scid mice (Pakala et al. 1997).

In addition, IFN-$\gamma$ correlates with diabetes (in NOD as well as in humans) and anti-IFN-$\gamma$ prevents disease; under disease IFN-$\gamma$+ cells are present in islets and antigen-specific Th1 clones accelerate the onset of diabetes (Pakala et al. 1997, O'Garra et al. 19971. Furthermore, Th2 cells only induce insulitis in neonatal NOD, but have the capacity to induce diabetes in immuno-compromised NOD.scid; also, disease is inhibitable by anti-IL-10, but not by anti-IL-4 (Pakala et al. 1997). This suggests that non-Th2 type regulator T cells are present in normal mice, but these are absent in immunodeficient mice. These results stress the existence of cells regulating the balance between activated Th-subpopulations. Possible disturbances in this balance induced by altered reactivity of such regulatory T cell populations can cause immune-mediated diseases, which results in absence or over-production of certain critically important cytokines (O'Garra et al. 1997).

Some auto-immune diseases, in particular Th1 mediated diseases, like rheumatoid arthritis (RA) (Grossman et al. 1997, Russel et al. 1997, Buyon et al. 1998, Hintzen et al. 1997) can remit during pregnancy. Furthermore, successful pregnancy is a Th2 type phenomenon (Raghupath et al. 1997). We tested hCG preparation and its fractions from Pregnyl [Organon, Oss] on the development of diabetes in NOD mice and in a in vitro model.

Surprisingly, we found that intraperitoneal treatment of NOD mice of age 15 weeks, with a hCG preparation for three times a week for a month can delay or inhibit the onset of diabetes. In addition, transfer of total spleen cells from these treated NOD mice into NOD.scid mice can delay or prevent diabetes in NOD.scid whereas transfer of non-treated spleen cells cannot. This anti-diabetic effect resides in a fraction obtainable from pregnant woman but not in hCG.

Mice. NOD mice were bred in our facilities under specific pathogen-free conditions. The spontaneous incidence of diabetes in our colony is 85% in females at weeks of age. NOD.scid mice were also bred in our facilities under specific pathogen-free conditions. Transfer of diabetogenic cells from NOD to NOD.scid at the age of 8 weeks induces diabetes after 22 days.

Diabetes. Diabetes was assessed by measurement of venous blood using an Abbott Medisense Precision Q.I.D. glucometer and also monitored for glucosuria (Gluketur Test; Boehringer Mannheim, Mannheim, Germany). Animals were considered diabetic after two consecutive glucose measurements of higher than 13.75 mmol/l (250 mg/dl). Onset of diabetes was dated from the first consecutive reading. In instances of sustained hyperglycemia of >33 mmol/l animals were killed to avoid prolonged discomfort.

Immunohistochemistry. Mice were killed by $CO_2$ asphyxiation. The entire pancreata were removed and snap frozen in OCT compound (Tissue-tek) for cry-sectioning. 5-$\mu$m cryo-sections were obtained, air dried, and stored at −20° C. until used. Formalin-fixed sections were depaxaffinised in xylene and alcohol, and stained with hematoxylin and eosin for general morphology. Immunohistochemistry for insulin was then performed using a two-step protocol. Endogenous peroxidase activity was blocked, and slides were incubated with a rabbit antiserum to insulin (Dako Corp., Carpenteria, Calif.; 1:500 in 5% normal mouse serum for 30 min). After washing steps, staining was revealed with horseradish peroxidase-conjugated anti-rabbit Ig (Dako; 1:500 in 5% NMS for 30 min) developed with amino-ethyl-carbazole (AEC; Pierce) for 10 min and mounted in crystalmount.

In vivo anti-diabetic effect: NOD mice at the age of 15 weeks were treated with PBS (n-4), 300 IU Pregnyl (n-4), or 600 IU Pregnyl (n=4) i.p., 3 times a week for four weeks and diabetes was assessed as mentioned above. After four weeks the treatment was stopped and the PBS and the 600 IU Pregnyl group were killed after one week. The 300 IU Pregnyl group was left alive till the age of 28 weeks. Spleen cell transfer. The spleen was removed from 600 IU Pregnyl treated NOD and PBS control treated NOD mice, and total spleen cells were recovered. These cells were washed twice with PBS and 20×10⁶ cells were i.p. transferred into a 8-wk-old NOD.scid mouse.

Transfer Experiments:

Total spleen cells were recovered from 9-wk-old NOD mice and stimulated in vitro in RPMI supplemented with 10% FBS with coated anti-CD3 (145-2C11; 25 mg/ml) and IL-2 (50 U/ml) along with 300 IU/ml IR-P, 100 mg/ml IR-U3-5 or IR-U/LMDF. Plates were then incubated at 37° C. in 5% of $CO_2$ in air for 48 hrs. After 48 hrs cells were twice washed with PBS and 20×10⁶ cells were i.p. transferred into an 8-wk-old NOD.scid mouse.

In vitro restimulation. Total spleen cells (1×10⁶ cells/ml) from 20-wk-old NOD were stimulated in RPMI+ suplemented with 10% FBS with LPS (*Ecoli;*10 μg/ml) or coated anti-CD3 (145-2c11;25 μg/ml) with different doses of hCG-Pregnyl (50, 100, 300, 600, 800 IU/ml), Fraction 1–2 (200 μg/ml), Fraction 3–5 (200(g/ml), human recombinant hCG, α-hCG, and β-hCG (each at 200 μg/ml) in flat bottom 96-well plates. Wells with anti-CD3 coating were implemented with IL-2 (40 IU/ml). Plates were incubated at 37° C. in 5% $CO_2$ in air for 48 hrs. After 48 hrs of incubation the supernatants were collected for cytokine analyses.

CD4+ T-cells were isolated from total spleen cells of 20-wk-old NOD and stimulated as mentioned above with anti-CD3 at different conditions. These wells were implemented with IL-2 (40 μg/ml) and anti-CD28 (10 μg/ml). After 48 hrs of incubation the supernatants were also collected for cytokine analyses.

To determine the effect of IR on the potential of CD4⁻ cells to differentiate into Th1 or Th2 cytokine producing effector cells, Th polarization assay was performed in the presence or absence of IR. Total spleen cells from 8-wk-old female NOD were used as a source to purify CD4+ cells. Purified CD4+ T cells from the spleen were obtained by negative selection due to complement depletion with antibodies specific for B cells, NK cells, monocytes/macrophages and granulocytes. Cells were further purified using magnetic activated cell sorting with a cocktail of biotinylated mAbs against CD11b, B220, CD8 and CD40, followed by incubation with streptavidin-conjugated microbeads (Milteny Biotech, Bergisch Gladbach, Germany). CD4+ cells used for experiments were always 90–951 purified as determined by flow cytometry. For primary stimulation, purified CD4+ T cells were cultured at 1×10⁵ cells/well in flat bottom 96-well plates (Nalge Nunc Int., Naperville, Ill., USA), and stimulated with plate-bound anti-CD3 mAb (145-2C11, 25 mg/ml), anti-CD28, and IL-2 (50 U/ml). For differentiation of Th1 cells, anti-IL-4 mAb (11B11; 10 mg/ml) and IL-12 (10 ng/ml) were added to the cultures. Priming for Th2 cells was with IL-4 (35 ng/ml) and anti-IFN-g mAb (XMG 1.2; 5 mg/ml). Furthermore, in Th1 and Th2 priming conditions, also 300 IU/ml IR-P and 100 mg/ml IR-U/LMDF in the presence or absence of blocking anti-IL-10 (10 mg/ml), anti-TGF-b (10 mg/ml), and VitD3 (10 mg/ml). Unprimed cultures contained only anti-CD3, anti-CD28 and IL-2. All doses were optimized in preliminary experiments. After 4 days of culture, the cells were washed 3 times and transferred to new anti-CD3-coated 96-well plates and restimulated in the presence of IL-2 (50 U/ml) and anti-CD29 (10 mg/ml). Forty-eight hours later, supernatants were collected and assayed for IL-4, IFN-g and IL-10 production by ELISA as a readout for Th1 versus Th2 polarization.

Ex Vivo NOD Cytokines Experiment:

In rodents the switch in the production of antibodies from IgM to IgG and other classes appears to be largely under T cell control mediated by cytokines. Dominant Th1 polarisation mediate switching B cells from IgM production to IgG2a under the influence of massive production of IFN-gamma, while Th2 polarisation induces isotype switching in B cells to IgG1 production. We treated NOD mice at the age of B-10 weeks with PBS (n=5) or IR-P and its fractions IR-P1, IR-P2, IR-P3, or recombinant hCG (rhCG) and rhCG in combination with IR-P3, each with 200 mg i.p. for three days. Total spleen cells were isolated from all groups and stimulated with LPS or coated anti-CD3 as mentioned before. At different time points cytokines and proliferation was measured as follows: anti-CD3 stimulated proliferation (t=12, 24, 48 h), anti-CD3 stimulated IFN-gamma (t=24, 30, 4B h), I.PS stimulated IgG2a production (t=7 days). In order to determine the effect of IR treatment on Th1 polarisation, we isolated CD4' cells and performed Th1 polarisation assays as mentioned before.

BALB/c Experiments;

To separate the immune-modulating activity of IR from its beneficial clinical effects, we treated healthy BALB/c mice i.p. with 300 IU IR-P or 100 mg/ml of IR-U/LMDF (n=5). This strain is generally considered to react upon stimulation with a Th2 driven immune response. After four days of treatment with IR, purified CD4+ spleen cells from control and IR-P treated mice were analyzed for Th polarization as mentioned above. In order to determine the effect of IR-P on cytokine levels produced by splenic APCs, spleen cells from control and IR-P treated BALB/c mice were stimulated in vitro with LPS (*E. coli* O26:B6; 10 mg/ml, Difco Laboratories, Detroit Mich., USA). After 48 hours of incubation supernatants were collected for cytokine analysis (IL-12p70, IL-6).

IL-10 Knockout Mice Experiment:

To determine the in vivo effect of IR-P in IL-10 gene targeted (IL-10KO) mice, we treated such mice (n=2) i.p. with 300 IU IR-P/day for 4 consecutive days. After 4 days of treatment spleen and lymph nodes cells were recovered and tested for their ability to proliferate in response to LPS and anti-CD3. In addition, CD4+ cells were purified from control and IR-P treated mice and analyzed for Th polarisation potential as mentioned above.

NOD Bone Marrow Cell Suspensions:

In order to determine IR-induced effects on dentritic cells (DC) derived from bone marrow (BM), BM of 9-wk-old female NOD mice (n=2) were isolated and incubated with 20 ng/ml GM-CSF (2.0×10⁵ cells/ml) for 6 days and at day 7 co-culture with 300 IU/ml IR-P or 100 mg/ml IR-U (IR-U, IR-U-F3-5 [superdex 75-derived], or IR-U/LMDF [FDC-derived]) for additional 24 hrs. Briefly, femora and tibiae were cleaned of muscles and tendons and ground in a mortar using DBSS-FCS. Single cell suspensions were obtained by aspiration through a 22 gauge needle into a 2 ml syringe, followed by sieving the cell suspension twice over nylon filters (mesh size 100 and 30 mm respectively; Polymon PES, Kabel, Amsterdam, The Netherlands). Furthermore, in order to know whether IR has also effect on the maturation of DC, BM from NOD mice were also directly co-cultured with GM-CSF and IR for 7 days. At day 8 all cells were analyzed by a flow cytometer for expression of the following markers: CD1d, CD11c, CD14, CD31, $CO_{40}$, CD43, CD80, CD86, CD95, ER-MP20, ER-MP58, F4/80, E-cad, MHC II, MHC I, RB6 8C5.

A similar experiment was performed with BM cells from a 9-wk-old female BALB/c mice (n-3).

Allo-Mixed Lymphocyte Reaction (MLR):

In order to test the immunosuppressive activity of IR on transplantation rejection, we performed allo-MLR. BM cells from 9-wk-old female BALB/c (n=3) were isolated as mentioned above and treated with (recombinant mouse) rmGM-CSF (20 ng/ml) and IR (IR-P; 300 IU/ml, IR-U; 300 mg/ml, IR-U3-5; 300 mg/ml, IR-U/LMDF; 300 mg/ml) for 7 days. After 7 days the DC generated were irradiated (2,000 rad) and co-cultured with splenic CD3$^+$ cells isolated from 9-wk-old female C57BL6/Ly. These CD3$^+$ and DC cells were cultured at various ratios and T cell proliferation was measured via [$^3$H]TdR incorporation (0.5 mCi/well during the last 16 hrs in culture).

Cytokine ELISA. IL-4 was detected using monoclonal anti-IL-4 antibody (11B11) as the capture antibody and revealed with biotinated-conjugated rat anti-mouse IL-4 monoclonal antibody (BVD6 24G2.3). INF-γ was detected using monoclonal anti-IFN-γ antibody (XMG1.2) as the capture antibody and revealed with biotinylated-conjugated rat anti-mouse IFN-γ monclonal antibody (R46A2). In both cases ABTS substrate was used for detection.

Flat bottom microplates (96-wells, Falcon 3912, Microtest II Flexible Assay Plate, Becton Dickinson, Oxnard, USA) were coated with cytokine specific capture antibodies for IL-6, IL-10, IL-4 and IFN-g diluted in PBS (1 mg/ml 20F3 and SXC-1; 5 mg/ml 11B11 and XMG1.2, respectively) at 4° C. for 18 hrs. After coating, plates were washed (PBS, 0.1% BSA, 0.05% Tween-20) and blocked with PBS supplemented with 1% BSA at room temperature for 1 hr. After washing, samples and standards were added and incubation was continued for at least 4 hrs at room temperature. Thereafter, plates were washed and biotinylated detection antibodies were added (1 mg/ml 32C11 (IL-6) and R46A2 (IFN-g); 0.1 mg/ml 2A5.1 (IL-10) and BVD6.24G2 (IL-4) and incubated overnight at 4° C. After washing, streptavidin-peroxidase (1/1500 diluted, Jackson Immunoresearch, West Grove, Pa., USA) was added. After 1 hr, plates were washed and the reaction was visualized using 2,2'-azino-bis-3-ethylbenz-thiazoline-6-sulfonic acid (ABTS, 1 mg/ml, Sigma, St. Louis, Mo., USA). Optical density was measured at 414 nm, using a Titertek Multiscan (Flow Labs, Redwood City, USA). The amounts of IL-12p70, TNF-a and TGF-b were measured with commercially available ELISA kits (Genzyme Corp, Cambridge, Mass.) according to the protocols provided by the manufacturer.

Sepsis or Septic Shock Experiments.

There are three common mouse models used to investigate sepsis or septic shock: high dose LPS, low dose LPS with D-Galactosamine sensitisation and low dose superantigen with D-Galactosamine.

One of the first models used for investigating sepsis or septic shock involved treatments with rather large doses of LPS in the inter-peritoneal cavity (between 300–1200 μg). Mice are quite resistant to bacterial toxins, yet succumb to this high dose. It has been suggested that a high dose of LPS in mice might correlate with a lower dose in humans (Mietheke et al.) Approximately 70% of sepsis or septic shocks in humans are caused by Gram-negative bacterial endotoxin and up to 30% are created by exotoxins released from Gram-positive bacteria. The traditional endotoxin—the distinctive lipopolysaccharide (LPS) is associated with the cell membrane of the Gram-negative organism represents the most common initiator of the sepsis or septic shock pathogenetic cascade. The endotoxin molecule consists of an outer core with a series of oligosaccharides that are antigenically and structurally diverse, an inner oligosaccharide core that has similarities among common gram-negative bacteria, and a core lipid A that is highly conserved across bacterial species. The lipid A is responsible for many of the toxic properties of endotoxin. The systemic effects of endotoxins, such as LPS seem to be largely mediated by macrophages, since adoptive transfer of endotoxin-sensitive macrophages renders previously endotoxin resistant mice sensitive to the toxin (Freudenberg et al. 1986).

The more commonly used model of endotoxin sepsis or septic shock takes advantage of the increased susceptibility of BALB/c mice to low doses of LPS after being simultaneously treated with Galactosamine (D-Gal sensitized). This D-Gal treatment dramatically sensitizes animals to the toxic effect of LPS, so that nanogram amounts induce a liver toxicity that is lethal for wild-type animals in a period of 6–7 h. This systemic effects of endotoxin seem to be largely mediated by macrophages. (Gutierrez-Ramos et al. 1997). Although certain mediators are undoubtedly more important than other in producing sepsis, probably dozens of organism- and host-derived mediators interacting, accelerating, and inhibiting one another, are responsible for the pathogenesis of sepsis or septic shock.

On response to LPS, TNF, and other mediators, endothelial cells and macrophages can release a potent vasodilator agent, endothelial-derived relaxing factor (EDRF), which has recently been identified as nitric oxide. This molecule causes smooth muscle cell relaxation and potent vasodilatation. Inhibiting nitric oxide production with competitive inhibitors of nitric oxide synthase results in increased blood pressure in animals with endotoxin shock. This suggests that nitric oxide may be partially responsible for the hypotension associated with sepsis. Although inhibition of nitric oxide restores blood pressure, such inhibition may reduce tissue blood flow. (Bennett et al.).

Endotoxin can also activate the complement cascade, usually via the alternative pathway. This results in the release of the anaphylotoxins C3a and C5a, which can induce vasodilatation, increased vascular permeability, platelet aggregation, activation and aggregation of neutrophils. These complement-derived mediators may be responsible in part for the microvascular abnormalities associated with sepsis or septic shock. Further, endotoxin can result in the release of bradykinin via the activation of Factor XII (Hageman factor), kallikrein, and kiniogen. Brandyinin is also a potent vasodilator and hypotensive agent. LPS activation of factor XII also leads to intrinsic and (through macrophage and endothelial cell release of tissue factor) extrinsic coagulation pathway activation. This result in consumption of coagulation factors and DIC. TNF also activates the extrinsic pathway and may contribute to these coagulation abnormalities.

Different metabolism of the arachidonic acid cascade are also known to cause vasodilatation (prostacyclins), vasoconstriction (thromboxanes), platelet aggregation, or neutrophil activation. In experimental animals, inhibiting cyclooxygenase or thromboxane synthase has protected against endotoxin shock. Elevated levels of thromboxane B2 (TBX2) and 6-ketoprostaglandin F1 (the end product of prostacylin metabolism) are present in patients with sepsis. A number of cytokines can cause release of these arachidonic acid metabolites from endothelial cells or leukocytes.

Figure 14:
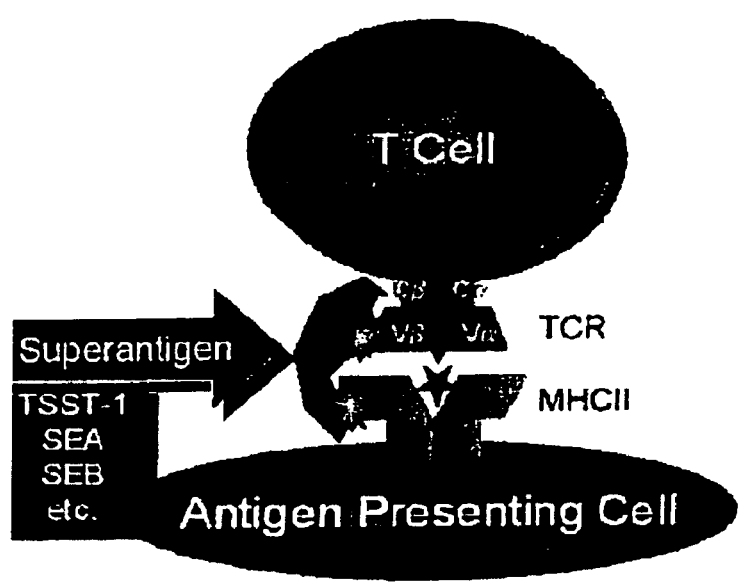

In a similar fashion, exotoxin shock model D-Gal sensitised BALB/c mice are treated with low doses of TSST-1 or SEB. These superantigens stimulate the proliferation and activation of a large proportion of T cells. In fact, the T cell activation induced by these super-antigens can almost be viewed as a polyclonal T-cell activation in that T-cells expressing a specific V-beta family are all activated through non antigen specific binding of the TCR/MHCII/ and superantigen (FIG. 14).

D-Galactosamine has been shown to be a transcription inhibitor which targets the liver, interfering with the synthesis of acute phase proteins. It is believed that these acute phase proteins infact help the liver detoxify/ or deactivate TNFα. In fact D-Galactosamine treatment in the low dose endotoxin or exotoxin models is acompanied by TNFα mediated hepatic apoptosis. D-galactosamine treatment alone does not result in hepatic apoptosis, and these organ damaging effects can be neutralised in both low dose models by neutralising anti-TNFα antibodies (Gutierrez-Ramos et al. 1997).

Mice used in sepsis or septic shock experiments: Female BALB/c and SJL mice between 8–12 weeks of age were used for all experiments. The animals were bred in our facility under specific pathogen-free conditions according to the protocols described in the Report of European Laboratory Animal Science Associations (FELASA) Working group on Animal Health (Laboratory Animals 28: 1–24, 1994).

Infection Protocols: Toxic Shock (TSST-1 & D-Galactosamine) (n=6).

For the exotoxin model, Balb/c mice were injected with 20 mg D-Galactosamine dissolved in 100 μl sterile saline solution (9%) intraperitoneally. They were then given 41 g of TSST-1 dissolved in 10 μl sterile saline solution (9%) injected subcutaneously in two sites approximately 0.5 cm below each shoulder blade. Control groups were injected with either 4 μg TSST-1 subcutaneously without D-Galactosamine, or treated with D-Galactosamine alone. A group of D-Galactosamine sensitised Balb/c mice were also pre-treated i.p. with 700 IU IR-P for 3 days before the treatment of TSST-1.

LPS Model (n=6)

For the endotoxin model, Balb/c and SJL mice were treated i.p. with 600 μg LPS. Control group were treated only with PBS i.p. To test the effect of IR-P, we also pretreated Balb/c and SJL mice with 700 IR-p for 3 days and then injected with 600 μg of LPS. Moreover, a group of Balb/c mice was also pretreated with IR-U fractions (IR-U, IR-U2, IR-U3-5), each with same doses of 200 μg i.p. for 3 days and then injected with 600 μg of LPS. In order to test low molecular weight fraction, we tested IR-U/LMDF (which also contains IR-U5 [[<10 Kda] fraction), IR-P3 (obtained by method 3), IR-A and IR-A3 (obtained by method 3), and their fractions obtained by method 4 for anti-shock activity. In addition we also test three fractions from peptide column (F1–3) for anti-shock activity (methods are shown elsewhere in this document). We also treated Balb/c mice with 700 IU IR-P twice i.p. after 1 and 2 hours of injection with LPS respectively.

Semi-Quantitative Sickness Measurements: Mice were scored for sickness levels using the following measurement scheme:

1 Percolated fur, but no detectable behaviour differences from normal mice.
2 Percolated fur, huddle reflex, responds to stimuli (such as tap on cage), just as active during handing as healthy mouse.
3 Slower response to tap on cage, passive or docile when handled, but still curious when alone in a new setting.
4 Lack of curiosity, little or no response to stimuli, quite immobile.
5 Laboured breathing, inability or slow to self-right after being rolled onto back (moribund, sacrificed).

WBC and Platelets Counts: 100 μl of blood was obtained from 2 randomly selected mice per group utilising a tail bleed method at the 24 hour time-point from TSST-1 model. Whole blood was collected in EDTA tubes and analysed in an automated blood hematology analyser.

Data on Shock

Animals and treatments; 8–10-wk-old female BALB/c mice obtained from Harlan were used in this study. Animals were killed and livers and spleens were excised for further study as indicated below. Mouse handling and experimental procedures were conducted in accordance with the American Association of Accreditation of Laboratory. Animal Care guidelines for animal care and use.

Injection protocols: LPS from *Escherichia coli* (Sigma Chemical Co) was administered intraperitoneally at 150 mg/kg for the high-dose LPS shock model. To test the effect of IR, mice were pretreated with IR-P (Pregnyl; Organon; Oss, The Netherlands) and its fractions, IR-P1, IR-P2, IR-P3 and with IR-A3 (APL; Wyeth Ayerst, Philidalphia, Pa., USA) for 3 days (t=-3, t=-2, t--1) each with the same dose of 200 mg i.p. and then LPS was injected at t=0 h. A group of mice was also treated with IR-P or Dexamethasone twice i.p. after 1 and 2 hours of injection with LPS, respectively.

Blood test: From each group blood was withdrawn by a tail bleed of 3 mice at each time point (t=-72h, -1 h and 48 h) and pooled for routine measurement of leukocytes, platelets, plasma enzymes LDH, ALAT and ASAT. Mice were then sacrificed and liver and spleens were excised and studied as indicated below.

Transplantation Model:

Animals and treatment: In order to determine whether IR-P is able to protect allograft, we treated BALE/c mice (n=5) with 600 I.U. IR-P/day i.p. or PBS for two days. On day 3 tail skin of C57BB/6 donors was grafted to the dorsal thorax of IR-P or PBS treated BALB/c recipients using a modification of the method of Billinghan and Medawar. Grafts were considered rejected when no viable donor skin/hair was detectable. After transplantation, IR-P pretreated BALB/c recipients were treated for additional two days.

EAE Model (MS)

Induction of EAE. 8–12 week-old female SJL mice (n=5) were immunized s.c. with 50 ml (0.5 mg/ml) of PLP-peptide at four different places (t=0). After 24 hours $10^{10}$ *Bordetella pertussis* was injected i.v. in tail. Subsequently, after 72 (t=3) hours mice were again immunized with *Bordetella pertussis*. From day 7 mice were weighted and clinical signs of EAE were graded daily on a scale of 0 to 5 as follows:

| EAE score | symptoms |
| --- | --- |
| 0 | no signs |
| 0.5 | paresis or partial tail paralysis |
| 1 | complete tail paralysis |
| 2 | paraparesis; limb weakness and tail paralysis |
| 2.5 | partial limb paralysis |
| 3 | complete hind or front limb paralysis |
| 3.5 | paraplegia |
| 4 | quadriplegia |
| 5 | death |

IR treatment: A group of mice were also treated from day 8 with 600 I.U. IR-P/day i.p. three times a week for two weeks, while control group was treated with same volume of PBS.

Streptozotocin Model:

Streptozotocin injections. For multiple dose streptozotocin (MD-STZ) model 25 mg/kg of STZ (Sigma) were dissolved in citrate buffer (pH 4.2) and injected intraperitoneally within 5 min of solubilization as described previously. Male mice were injected on 5 consecutive days (experiment day 1 through day 5) at 6–9 weeks of age. After 5 consecutive days of STZ, mice were treated with IR-P (600 I.U. i.p.) (n=5) or citrate buffer (n=5) four times a week for three weeks. For high dose streptozotocin (HD-STZ) model hyperglycemia was induced in mice by a single intraperitoneal injection of streptozotocin (160 mg/kg). Mice in the control group received a corresponding volume of citrate buffer alone. hCG fraction preparation and characterisation. Gel filtration of the solution of 1 or 2 vials of commercial grade hCG-Pregnyl (5,000 IU/vial) was performed on a Pharmacia FPLC sytem equipted with a Superdex 75 column (HR 5/30) (Pharmacia, Sweden) in PBS. Sample load volume was 1 ml. The flow rate was 0.5 ml/min for 45 min to followed. The 1 minute flow rate of 0.2 ml/min was implemented because of the viscosity of the commercial grade hCG solution which has a high lactose content hCG and a very low amount hCG core fragment were present in the relatively purified Pregnyl preparation of hCG and their positions were used as internal size markers hCG eluted as 78 kDa molecule and the hCG β-core eluted as a 19 kDa molecules on gel filtration. There were 1–5 fractions collected whereby fraction 1–2 contained hCG and fraction 5 contained the hCG (-core fragments. Fraction 1–2 and fraction 3-5 were tested for anti-diabetic effect by treating in vitro total spleen cells of 20-wk-old NOD and transferring them into NOD.scid. In this way human recombinant hCG, α-hCG, and β-hCG (Sigma, St. Louis, Mo. USA) were also tested.

Figure 15:
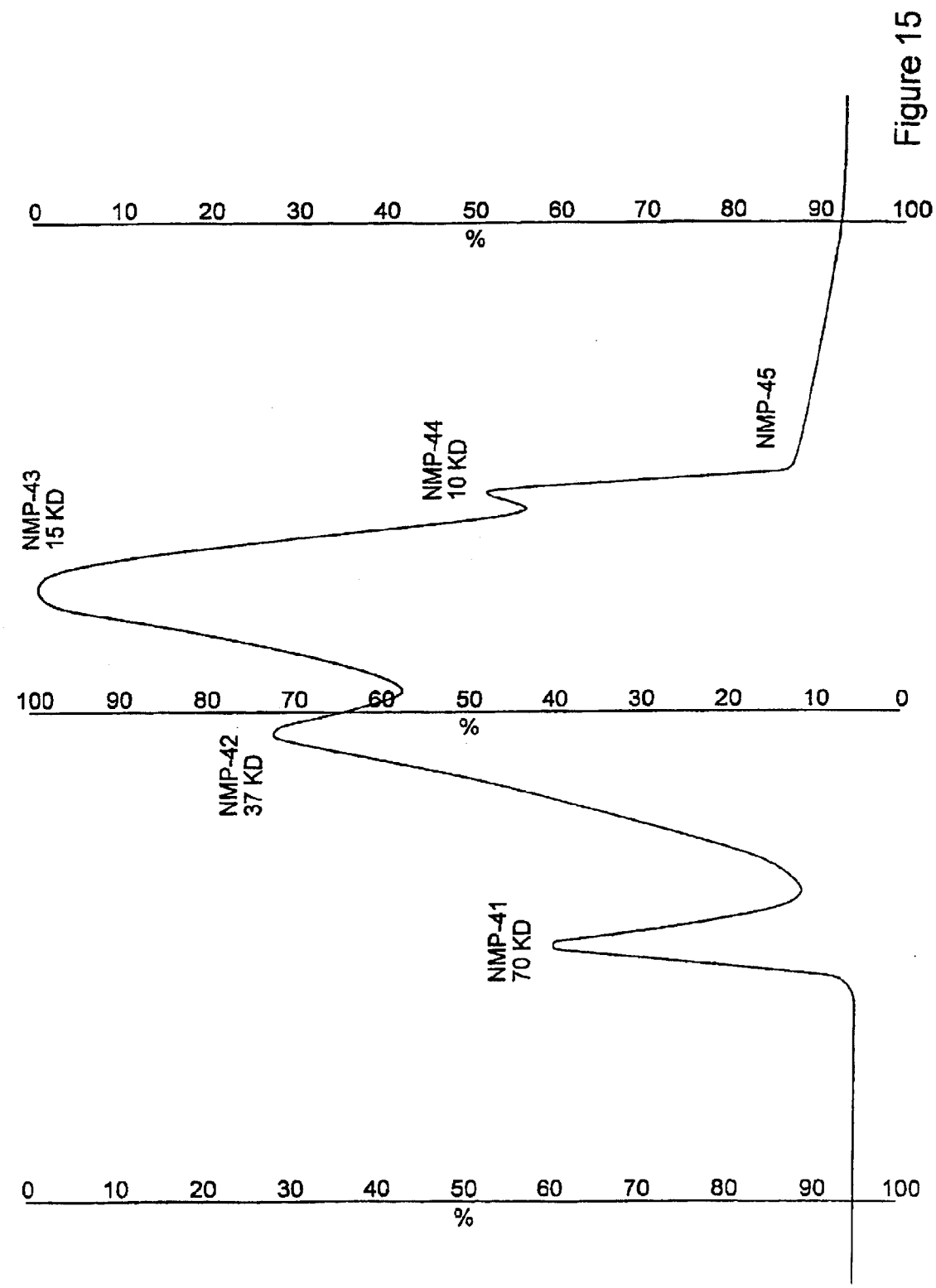

Gel permeation of IR-U and IR-P: FIG. 15 represents a FPLC chroatogram of 50 µl of undiluted IR-U sample. The running buffer was PBS. The chromatogram indicates 4 major peaks at 70, 37, 15 and 10 kDa. To identify these peaks, a sample of 500 µl (containing 5000 IU) of IR-P (Pregynl) was applied on the same column under similar running conditions. The profile obtained (FIG. 16) displayed also these 4 peaks although the ratios were different. Peak fraction 2 represents (alpha/beta) heterodimer hCG (37 kDa) while fraction 3 represents individual chains, homodimers of these chains or beta-core residual chains and other molecules (15–30 kDa). From these results we concluded that first trimester urine contains the same 4 major protein fractions that are also present in commercial hCG preparation, as could be expected. We named them as (IR-P1, IR-P2, IR3-5[pooled]), (IR-U1, IR-U2, IR-U3-5 [pooled]). Fraction 5 contains no protein or protein less than 10 kDa weight. In addition overlapping fractions 2 and 3 were seen in IR-P as well as in IR-U which suggested covalent binding of protein species present in these fractions.

Figure 17:
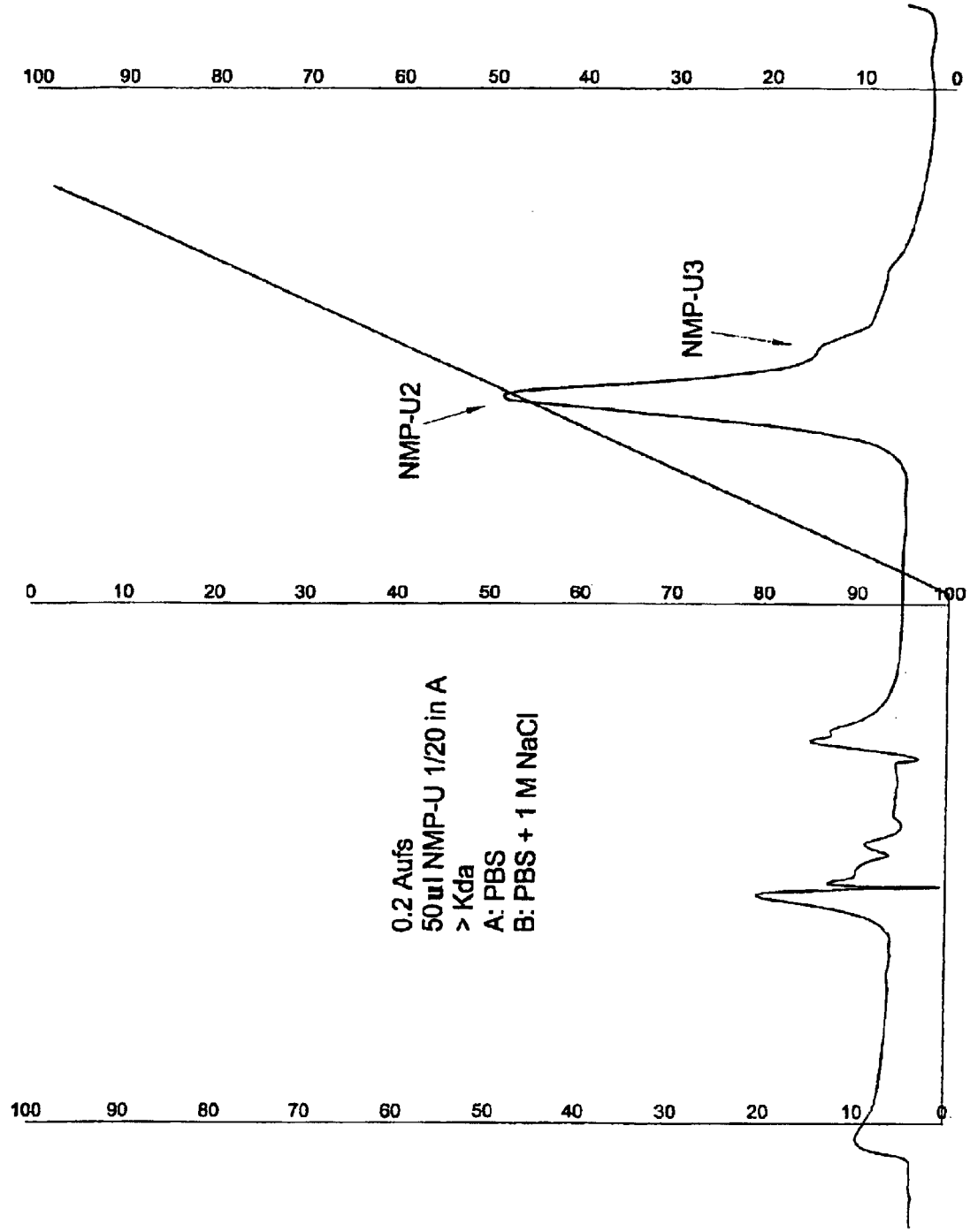

Anion Exchange Chromatography and Further Treatment of IR-U and IR-P:

Further separation of the overlapping fractions 2 and 3, was done on a 1 ml MONO Q HR 5/5 anion exchange column. FIG. 17 represents a chromatogram of 50 µl of IR-U sample diluted 1:20 in PBS. Two major protein peaks eluted at 43% and 55% buffer B but were not separated suggesting covalent binding between these protein species. Even using a discontinuous elution gradient with a 50% buffer B hold did not result in separation of these peaks (data not shown). Therefore, we concluded that ion exchange chromatography could not be used for further purification due to covalent binding of protein species present in the urine sample.

Figure 18:
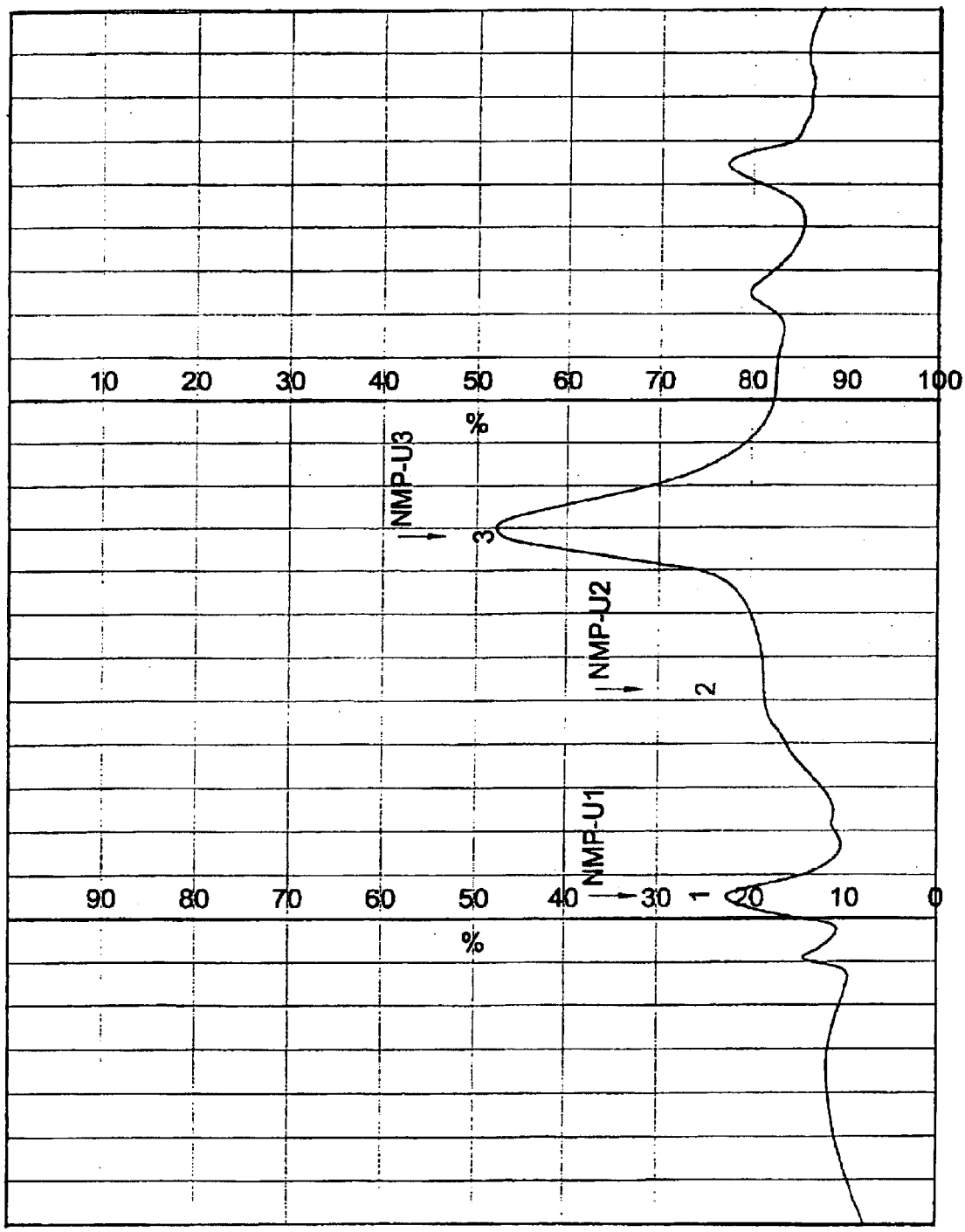

To reduce the presumed covalent binding between the important protein species present in the IR-U sample, we treated the sample with 60 mM 2-mercaptoethanol for 3 min at 100° C. and sample was then applied to the Superdex 75 column under identical conditions. FIG. 18 represents the elution profile showing that peak 1 (70 kDa) remains present (see also FIGS. 15–17), fraction 2 (representing hCG, 37 kDa) did nearly disappear and resulted in two new peaks a low molecular weight (<10 kDa). Peak 3 remained present and therefore is likely to contain isolated beta-core and monomeric proteins is excess. Peak 4 (10 kDa) also disappeared due to the reducing treatment.

A similar reducing treatment was applied to sample of IR-P (Pregnyl). Like the profile of the IR-U sample also treated, hCG (FIG. 19) displayed the decrease in peak 2, increase in peak 3, while a new protein peak appeared between peaks 1 and 2. Moreover, an increase in the breakdown product peak (<10 kDa) was apparent.

Transfer Experiments:

Total spleen cells were recovered from 9-wk-old NOD and stimulated in vitro in RPMI+supplemented with 10% FBS with ccated anti-CD3 (145-2c11; 25 mg/ml) and IL-2 (50 U/ml) along with 300 IU/ml IR-P, 100 mg/ml IR-U3–5 or IR-U/LMDF. Plates were then incubated at 37° C. in 5% of $CO_2$ in air for 48 hrs. After 48 hrs cells were twice washed with PBS and 20×10$^6$ cells were i.p. transferred into an 8-wk-old NOD.scid mouse.

Figure 3:
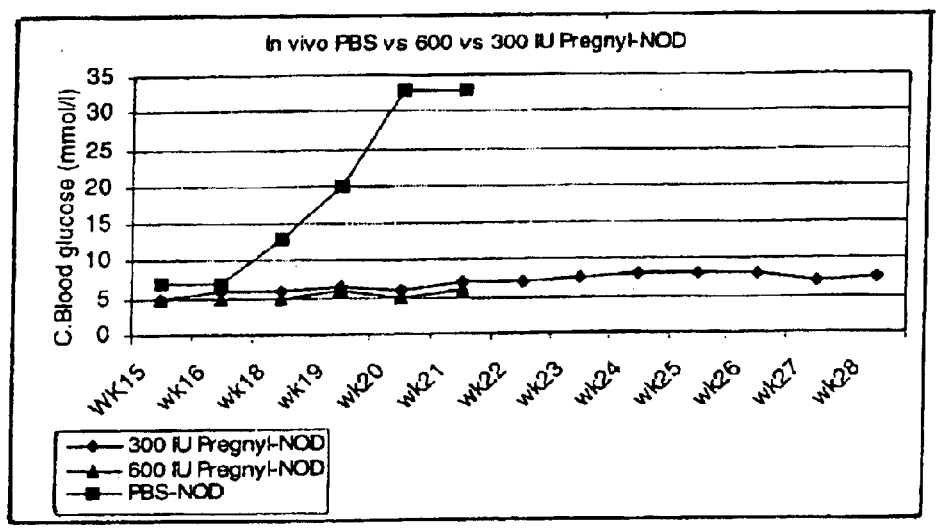

In vivo anti-diabetic effect of IR: Four 15-wk-old NOD female mice (n=4) were treated with PBS, 300 IU Pregnyl, or 600 IU Pregnyl intraperitonealy, 3 times a week for four weeks. After the treatment all mice in the PBS group were diabetic (blood glucose >33 mmol/l), they lost weight and looked uncomfortable, while the 300 IU Pregnyl and 600 IU Pregnyl groups remained free of disease. Their blood glucose levels never exceeded 6 mmol/l and they looked very healthy (FIGS. 1 and 3). In order to assess possible infiltrations and intact insulin producing cells in the pancreas, mice from the PBS and the 600 IU Pregnyl groups were killed after treatment and entire pancreata were removed for immunohistochemistry for insulin. Pancreas sections from the PBS group showed many infiltrating cells in the pancreas and these cells penetrated the islets. There were also large number of B lymphocytes and T lymphocytes present in the pancreata of the PBS-group. This finding was consistent with our other finding of an elevated ratio of splenic CD8/CD4 cells due to a selective reduction in the number of $CO_4$+cells and a decrease in the number of B lymphocytes in the spleen of these mice (data not shown). In the 600 IU Pregnyl group, pancreata were free of infiltration and, surprisingly, a number of new insulin producing islets were seen. There was also a decrease in the number of B lymphocytes and T lymphocytes in pancreas, which was consistent with normal levels of the CD8/CD4 ratio and the number of B lymphocytes in the spleens of these mice. Mice from the 300 IU Pregnyl group were kept alive till the age of 28 weeks. They appeared healthy, did not loose their weight and never had blood glucose levels above 8 mmol/l (FIGS. 1 and 3). Immunohistochemistry for the presence of insulin was also performed. There were still infiltrating cells present and some insulin producing islets in the pancreas. These mice were treated for four weeks with Pregnyl along with the 600 IU Pregnyl group and from wk 20 till 28 they were left untreated.

In order to determine whether the spleen cells of treated and untreated NOD mice still had the potential to induce diabetes in NOD.scid, we transferred spleen cells from the PBS and the 600 IU Pregnyl group into NOD.scid mice. 22 days after transferring, the PBS NOD.scid group were positive for diabetes and within a week they reached a blood glucose level above 33 mmol/l, while NOD.scid mice receiving spleen cells frog the 600 IU Pregnyl group remained normal (blood glucose <7 mmol/l). 7 weeks after transferring, the PBS group looked very uncomfortable (FIG. 2.), while the 600.10 Pregnyl. NOD.scid group still had blood glucose levels less than 9 mmol/l and remained healthy. Mice from both groups were killed at this time.

In vitro restimulation. Since high levels of IFN-γ, IL-1, and TNF-á were reported during the course of disease in NOD and this cytokine profile fits in a selective activation of the Th1 subset, we tested in vitro the effect of Pregnyl on cytokine production by total spleen cells and purified CD4+ cells from 20-wk-old NOD female mice. In order to assess whether the anti-diabetic effect resides in hCG or in one of its subunits or in other factors contained in the preparation used, we also tested the effect of different fractions obtained by gelpermeation chromatography from Pregnyl (FIG. 12) and human recombinant hCG and its subunits on cytokine production. The effect of these fractions were also tested in vivo on blood glucose levels in reconstituted NOD.scid mice.

Figure 4:
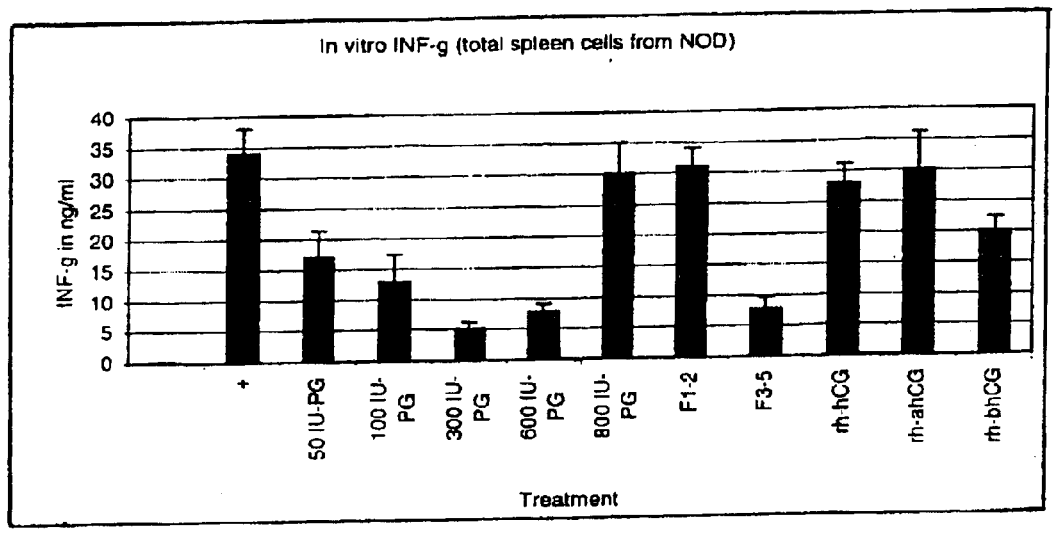
Figure 5:
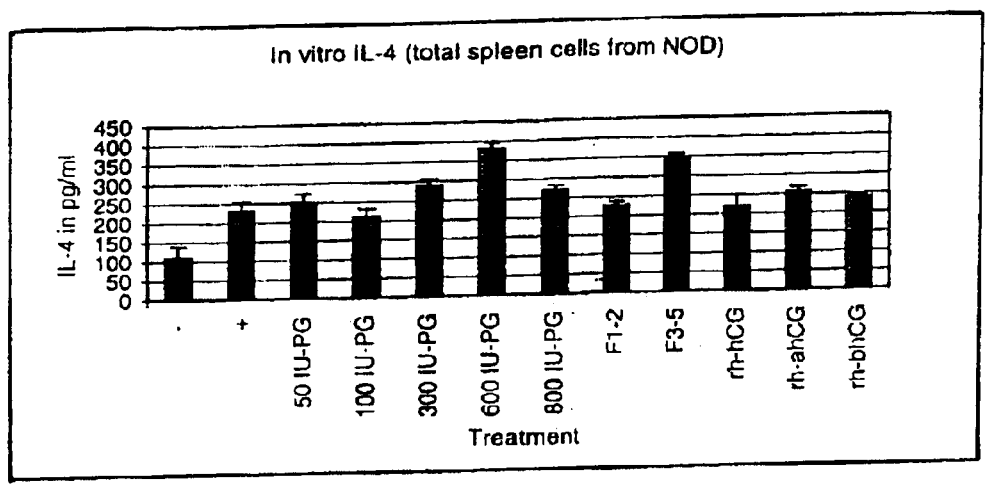
Figure 6:
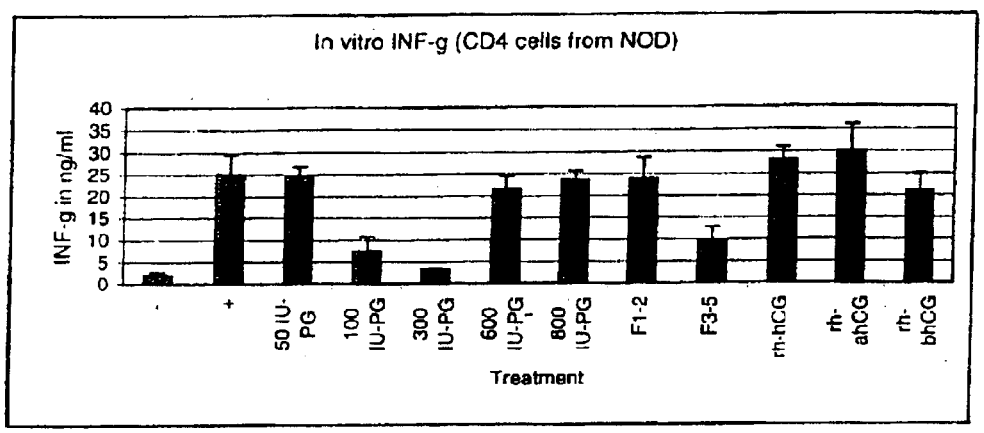

We observed a strong inhibition of IFN-α production by spleen cells obtained from mice treated with 50–600 IU/ml of Pregnyl, F3–5 (58–15 Kda) and to a lesser extent with human recombinant-βCG (FIGS. 4–6). There was only a moderate increase in IFN-γ production splenocytes from mice treated with 800 IU/ml Pregnyl. A similar pattern was observed when analyzing Il-4 production (FIG. 5). In addition a marked inhibition of IL-1 and TNF-á production was observed in stimulated splenocytes from mice treated with 300–600 IU/ml Pregnyl, with a concomitant stimulation of IL-6 and IL-10 production (data not shown).

Figure 7:
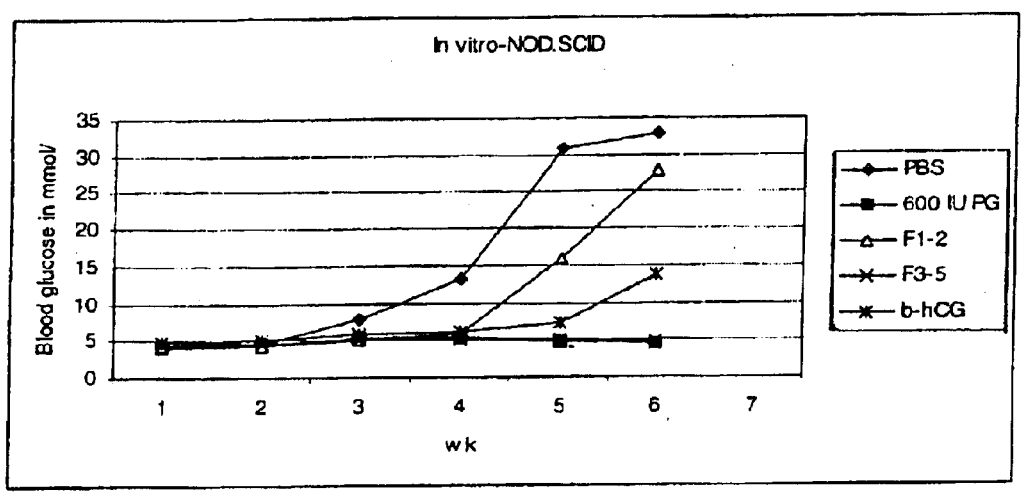

Furthermore, transfer experiments showed that total spleen cells of 20-wk-old NOD mice treated with F3–5 or IU Pregnyl can delay or even prevent the onset of diabetes in NOD.scid as compared to reconstitution with PBS treated NOD cells (FIG. 7). However, no significant effect was observed with F1–2 (80–70 Kda) on the onset of diabetes in NOD.scid mice. In order to test whether Pregnyl has also effect on Th2 type mice, we treated BALB/c mice (n=5) with 300 IU Pregnyl i.p. for four days and with PBS (n=5). After isolating CD4+ cells from spleens we stimulated them with anti-CD3/IL-2 for 48 hours and the supernatants were collected for the determination of IFN-γ and IL-4 cytokines. We also treated CD4+ cells with different doses of Pregnyl. Subsequently the supernatants were collected for cytokine anaylses. There was a marked inhibition of IFN-γ and a concomitant stimulation of IL-4 found in CD4+ cells stimulated with anti-CD3/IL-2 only (Th1->Th2), while the inverse was seen in CD4+ cells treated in vitro with different doses of Pregnyl (Th2->Th1).

Anti-diabetic Activity of IR-U/LMDF

In order test the anti-diabetic activity of IR-U/LMDF (<5 Kda), we treated diabetogenic cells in vitro with this fraction and with PBS (control). Transferring of these cells into NOD.scid mice revealed that reconstituted NOD.scid mice with IR-U/LMDF treated cells had delayed onset of diabetes as compared to the control group (n=3).

Figure 28:
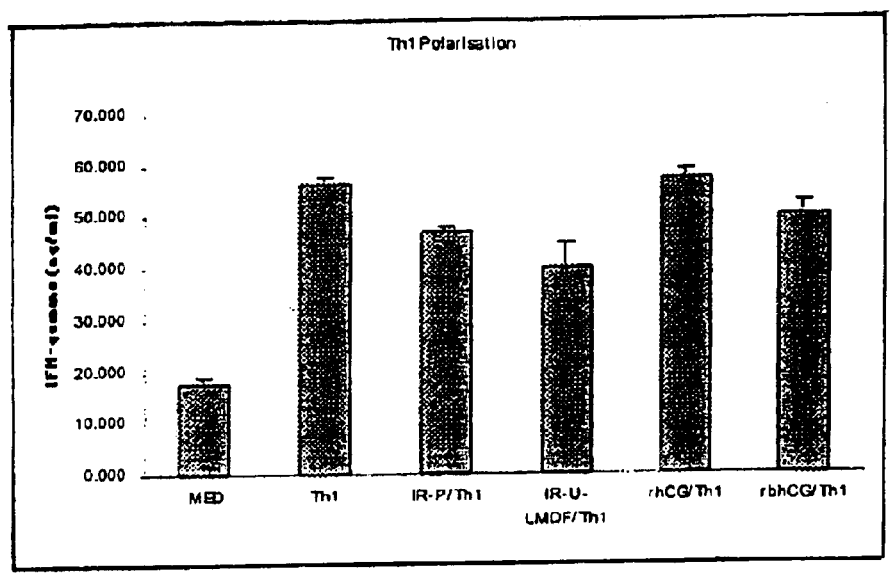

To determine the effect of IR on the potential of CD4-cells to differentiate into Th1 cytokine producing effector cells, the Th polarization assay was performed in the presence or absence of IR. We also tested recombinant hCG (rhCG) and beta-hCG in this Th polarization assay. A strong inhibition of IFN-gamma found with IR-P and IR-U/LMDF on CD4+ cells polarizing towards the Th1 phenotype (FIG. 28). There was only a moderate inhibition of IFN-gamma was production observed with recombinant beta-hCG and no effect was seen with recombinant hCG (FIG. 28).

Figure 64:
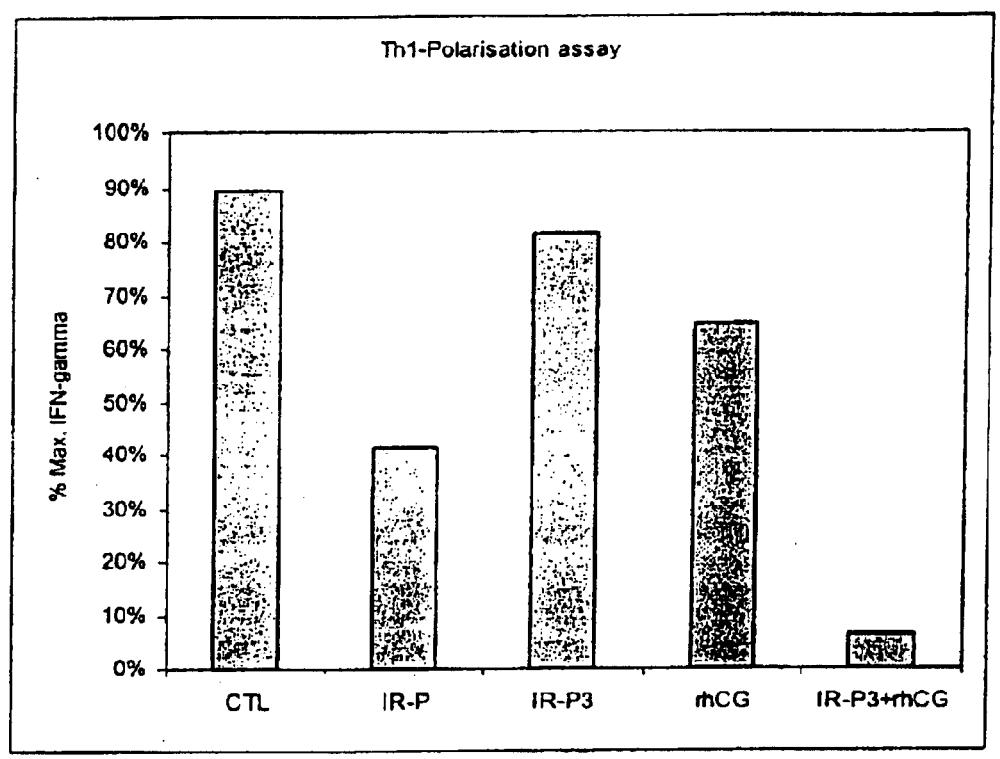

To determine whether IR-P3 needed an additional factor, such as hCG, to exert its full activity, we also treated NOD mice with IR-P, its fraction IR-P3, rhCG and IR-P3 in combination with rhCG and then Th1 polarisation was performed. FIG. 64 shows that IR-P inhibited the production of IFN-gamma in Th1 polarisation assay and thereby inhibited the outgrowth of Th1 cells under Th1 polarizing conditions. There was moderate inhibition of the Th1 polarisation found with IR-P3 and rhCG alone, while the outgrowth of Th1 cells was completely blocked with the combination of rhCG and IR-P3 (FIG. 64).

Figure 65:
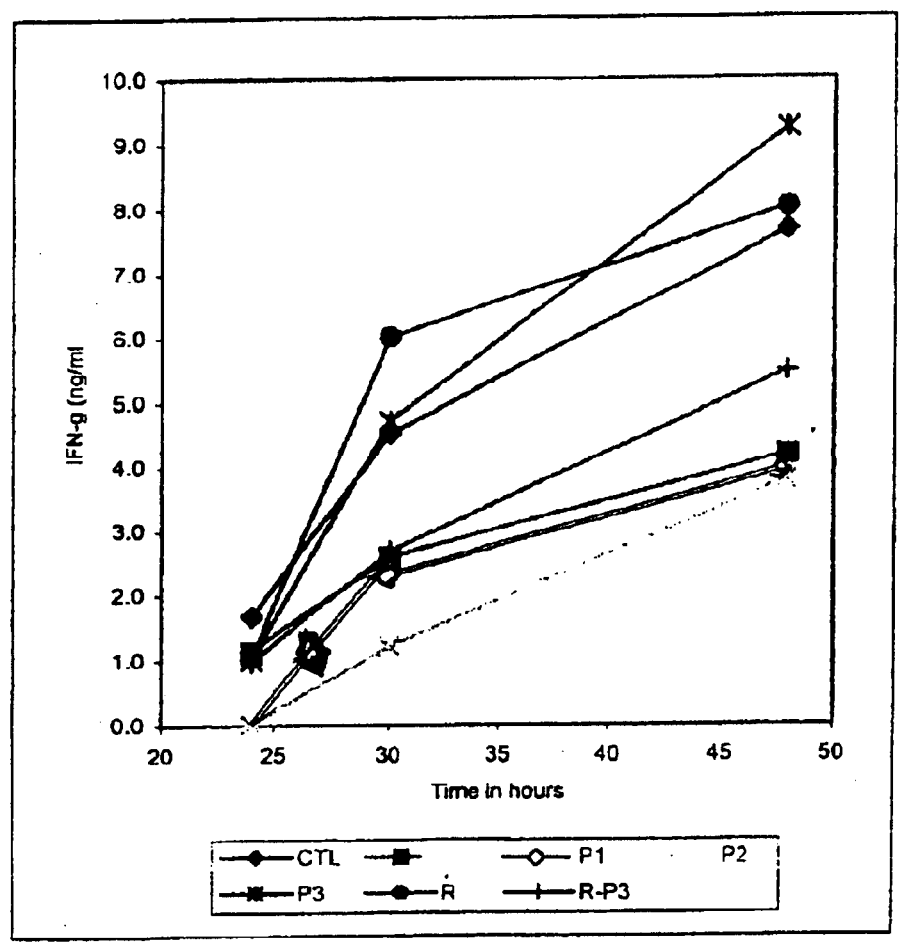

We also stimulated spleen cells from these IR treated mice with anti-CD3 and then at different time points IFN-gamma and IL-10 production was measured. Figure FIG. 65 shows that in vivo treatment with IR-P, and its fractions IR-P1, IR-P2 inhibited the in vitro anti-CD3 stimulated IFN-gamma production, while a moderate increase in IFN-gamma production was found with rhCG and IR-P3. In addition fraction IR-P3 in combination with rhCG was able to inhibit the production of IFN-gamma (FIG. 65). We also measured anti-CD3 stimulated IL-10 production (t=48) in splenocyte cultures of these in vivo treated mice. Figure (FIG. 67) shows that all fractions (IR-P, IR-P1, IR-P2, IR-P3) were able to increase the production of IL-10.

Since IR and its fraction promote anti-CD3 proliferation of splenocytes in vitro, so in order to know the effect of in vivo treatment with IR on anti-CD3 stimulated proliferation in vitro, we also measured the anti-CD3 stimulated proliferation of splenocytes obtained from these IR treated mice at different time points (t=12, 24, 48 h). FIG. (66) shows that anti-CD3 stimulated splenocytes from NOD mice treated with IR-P, and IR-P1 have a smaller capacty to proliferate in vitro. Furthermore, splenocytes from IR-P3 and rhCG treated mice showed a higher capacity to proliferate as compared to the PBS treated control mice (CTL), while IR-P3 in combination with rhCG caused the same decrease in proliferation as IR-P. Moderate effect was found in the anti-CD3 stimulated proliferation of splenocytes from IR-P2 treated NOD mice.

Figure 68:
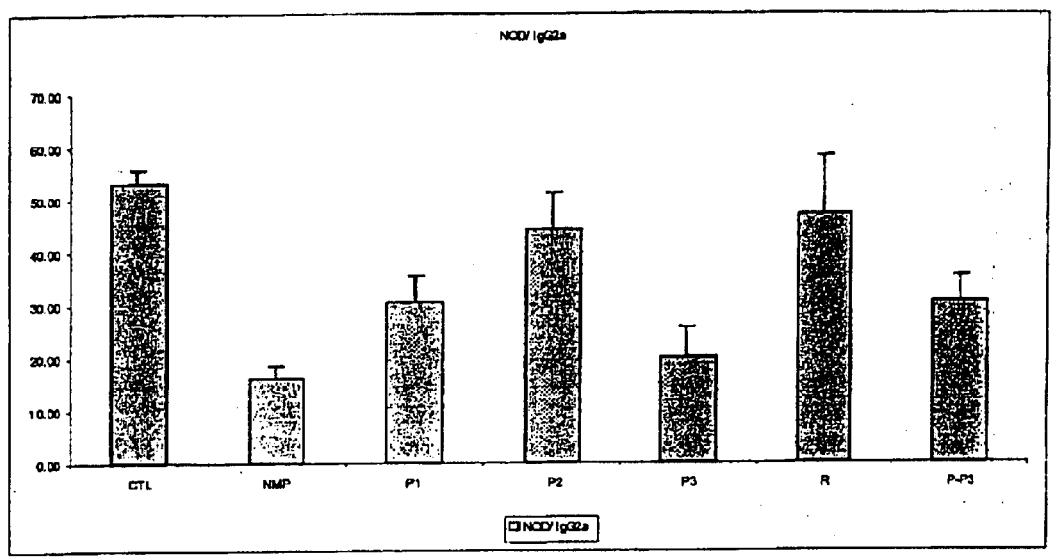

As mentioned above, dominant Th1 polarisation cause B cell switch from IgM to IgG2a production under the influence of massive production of IFN-gamma,. Therefore we also measured IgG2a production in LPS stimulated splenocytes obtained from IR treated NOD mice. FIG. 68 shows that LPS stimulated splenocytes from IR-P, IR-P1 and IR-P3 treated produced in vitro less IgG2a, while moderate inhibition of IgG2a was found with IR-P2. Furthermore, again rhCG treatment was not able to decrease the production of IgG2a while in combination with IR-P3 it did (FIG. 68).

GM-CSF Stimulated NOD Bone Marrow Cells:

In order to determine the effect of IR on the maturation of dendritic cells (DC) from the bone marrow, we cultured bone marrow cells from 8-wk-old NOD mice for 7 days in the presence of GM-CSF. Under these conditions the outgrowth of DC from bone marrow is more then 90%. When we co-cultured DC in the presence of GM-CSF and IR-P for 7 days, we observed that all DC treated with IR were less mature than control DC treated with GM-CSF only. This was concluded from the decrease in cell surface markers CD1d, ER-MP58, F4/80, CD14, and the increase in CD43, CD95, CD31 and E-cad (FIG. 29). Moreover no change was observed in cell surface markers ER-MP20/LY6C, MHC I and II (FIG. 29).

In contrast, when DC were cultured with GM-CSF for 6 days and at day 7 co-cultured with 300 IU/ml IR-P or 100 mg/ml (FIG. 30) of IR-U/LMDF (FIG. 31) for additional 24 hrs, the DC became more mature and could function better as APC. This was concluded from the increase in CD1d, CD40, CD80, CD86, CD95, F4/80, CD11c and MHC II cell surface markers (FIGS. 30 and 31).

Figure 45:
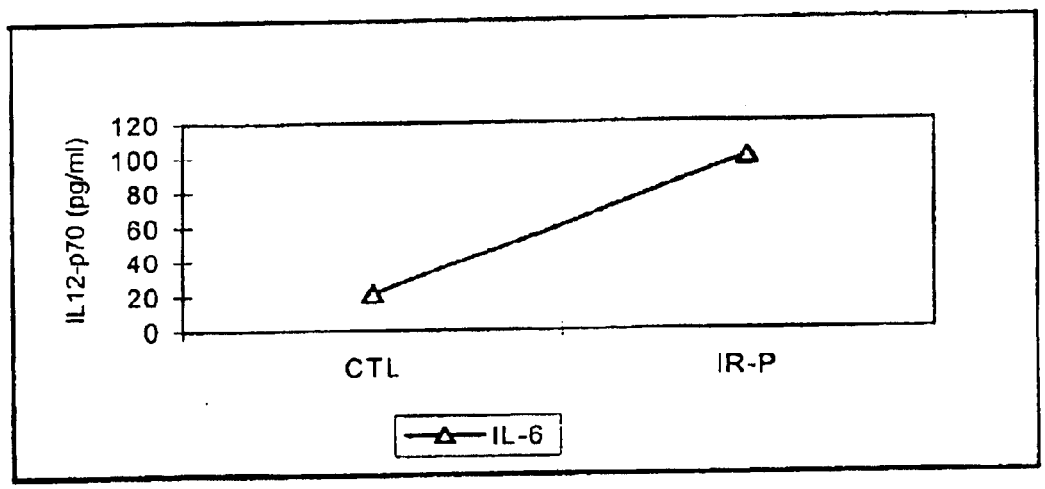
Figure 34:
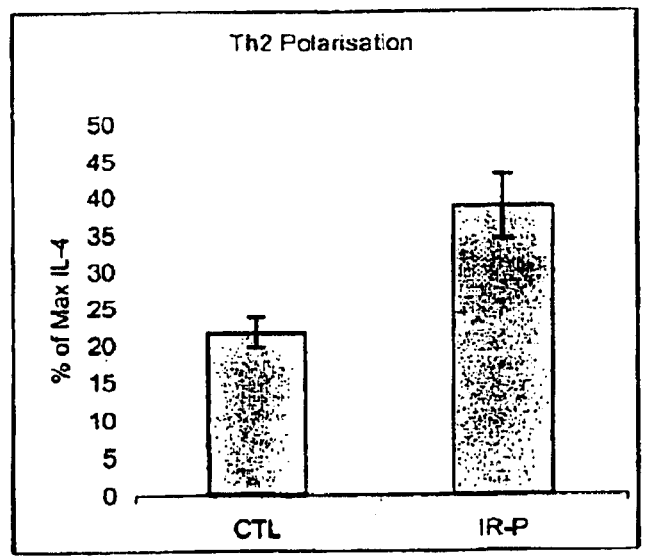
Figure 40:
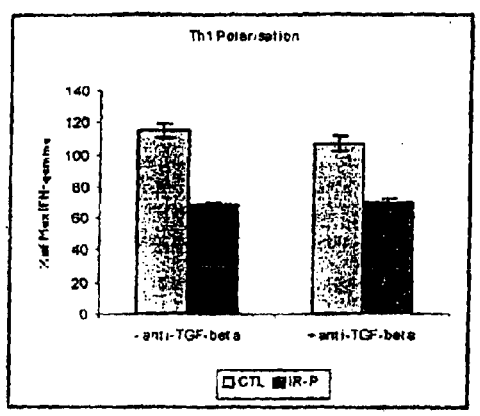
Figure 41:
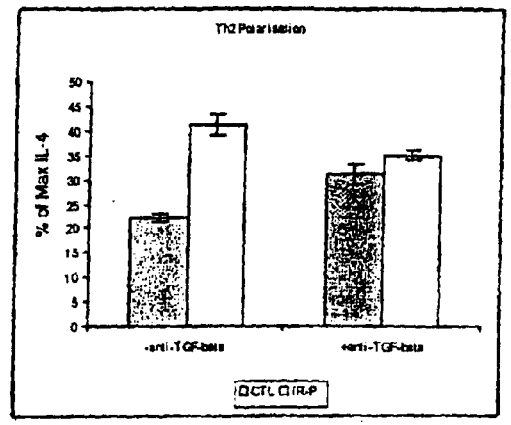
Figure 35:
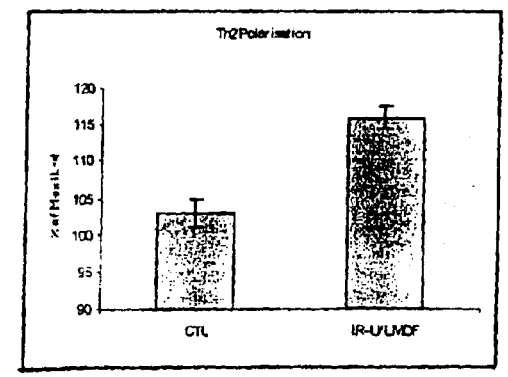
Figure 43:
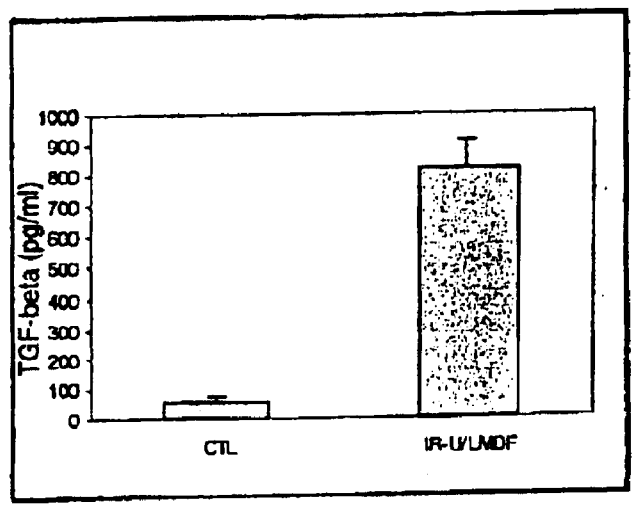

BALB/c Polarixation Assay:

In order to test whether IR has also effect on Th2 phenotype mice, we tested IR-P and IR-U/LMDF in BALB/c mice. After the IR treatment, we isolated CD4+ T cells in the polarization assay. Polarization assays revealed that CD4+ T cells from IR-P and IR-U/LMDF treated mice have less ability to produce IFN-gamma (FIGS. 32 and 33), while these cells produced more IL-4 as compared to cells from PBS-treated mice (FIGS. 34 and 35). This suggests that due to the in vivo treatment with IR, T cells are shifted more towards Th2 phenotype. CD4+ T cells from PBS treated and IR-P mice treated with different doses of IR-P showed an increase in IFN-gamma (FIG. 36) and a decrease in IL-4 (FIG. 37) production, which suggests a shift towards the Th1 phenotype. In order to determine whether a shift of CD4+ T cells towards the Th2 phenotype is IL-10 or TGF-beta dependent, we also added anti-IL-10 and anti-TGF-beta in the polarization assays of CD4+ T cells from IR-P treated mice. This caused an increase of IFN-gamma production under Th1 polarization conditions of IR-P treated mice cells and of IL-4 production under Th2 polarization conditions supported by anti-IL-10 addition (FIGS. 38 and 39) which suggests an involvement of IL-10 in Th1/Th2 polarisation with IR-P. Furthermore, no big differences were seen of IL-4 and IFN-gamma production in Th2 and Th1 polarization conditions with anti-TGF-beta in vitro treatment (FIGS. 40 and 41) between control and IR-P treated group. This proves that due to the IR treatment IL-10 and TGF-beta are involved. Moreover purified CD4+ cell from IR-U/LMDF produce more TFG-beta then the cells from control mice (FIG. 43). When anti-IL-10 or anti-IL-6 was added in both cultures, CD4+ cell from control group mice produce more TGF-beta then IR-U/LMDF treated group. This suggest an involvement of IL-6 and IL-10 in TGF-beta production. This is consistent with our data which shows that LPS stimulated spleen cells from IR treated mice produce high level of IL-6 (FIG. 45) as compared to control mice.

Figure 46:
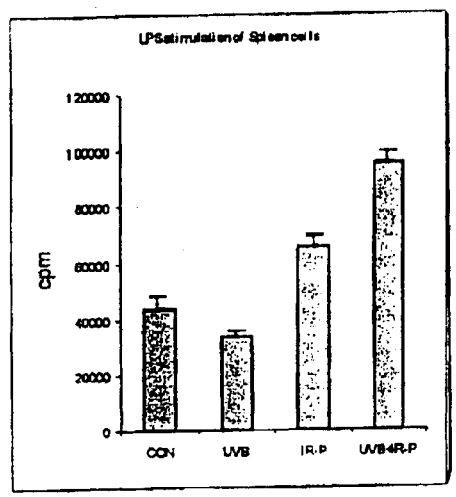
Figure 47:
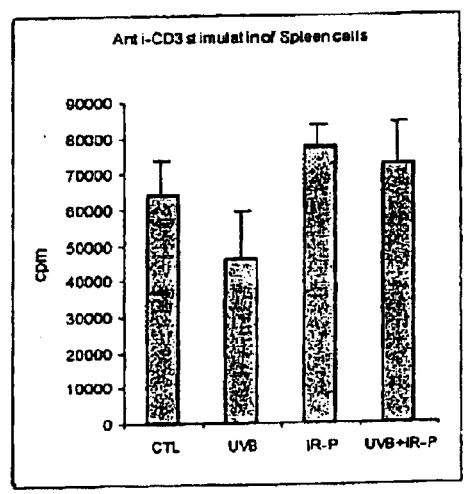

Spleen cells from mice irradiated with UVB also produced more IL-10 and induced suppression of Th1 cytokines. LPS and anti-CD3 stimulation of spleen cells from these mice revealed they are less capable to proliferate. We also compared the LPS and anti-CD3 stimulated proliferation of spleen cells from UVB and IR treated BALB/c mice. Reduction in LPS and anti-CD3 induced proliferation was observed after culture of splenocytes from UVB treated BALB/c mice (FIGS. 46 and 47), while IR or combined treatment by IR and UVB-irradiation treatment increased the LPS and anti-CD3 stimulated proliferation (FIGS. 46 and 47).

Figure 50:
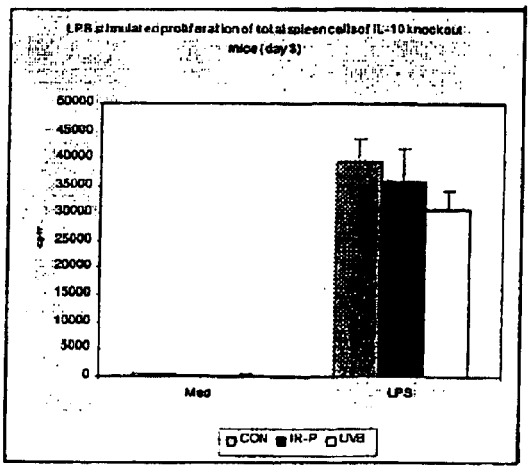
Figure 49:
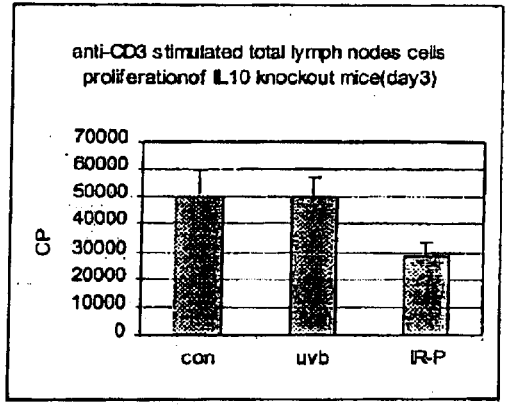

IL-10 Knockout Mice Result:

In order to determine whether this change in LPS and anti-CD3 stimulated proliferation is IL-10 dependent, we treated IL-10 knockout mice with IR-P or UVB. No change in proliferation pattern was seen in anti-CD3 stimulated spleen cells when UVB-irradiated and IR-P treated BALB/c mice were compared (FIG. 47), while the inverse pattern in proliferation was observed in anti-CD3 stimulated lymph node cells as compare to UVB-irradiated BALB/c both groups (FIG. 49). This shows that the decrease in anti-CD3 stimulated proliferation after UVB treatment or increase in proliferation after IR-P treatment of spleen cells is not completely IL-10 dependent, while this is true for anti-CD3 stimulated lymph node cells. When the LPS stimulated proliferation of spleen cells was evaluted at 48 hours, we observed an increase of proliferation in the UVB and IR-P treated groups as compared to the control group (FIG. 51), while a decrease in proliferation was observed in both groups at 72 hours of proliferation (FIG. 50).

In order to determine the influence of in vivo UVB or IR-P-treatment on the percentage of positive cells for CD4, CD8, B220, M5/114 cell surface markers, we performed flow cytometry analysis on lymph node cells and spleen cells. Reduction in B220 and M5/114 positive cells, and an increase in CD4 and CDB positive cells was observed in to the lymph nodes of IR-P-treated IL-10 knockout mice (FIG. 52), while an increase in CD4, CD8, B220 and M5/114 positive cells was observed in the spleen (FIG. 53). In the UVB treated group, an increase in CD8 positive cells and a decrease in CD4, B220, and M5/114 positive cells was seen in lymph nodes (FIG. 52), while no change in cell markers was observed among spleen cells, except for a moderate increase in CD8 positive cells (FIG. 53).

GM-CSF Stimulated Bone Marrow Cells Results:

In order to determine the effect of IR on the maturity of dendritic cells (DC) of the bone marrow, we cultured bone marrow cells from BALB/c mice for 7 days in the presence of GM-CSF. In this way the outgrowth of DC from bone marrow is more than 90%. When we co-cultured these DC in the presence of GM-CSF and IR (IR-P, IR-U, IR-U3-5, IR-U/LMDF) for 7 days, we observed that all DC treated with IR were less mature than control DC treated with GM-CSF only. This was concluded from the decrease in cell surface markers CD1d, CD40, CD80, CD86, ER-MP58, F4/80, E-cad and MHC II (FIG. 54). Moreover, moderate increase in CD95 was observed (FIG. 54). In contrast, when DC were cultured with GM-CSF for 6 days and on day 7 the culture were supplemented with 300 IU/ml IR-P or 100 mg/ml IR-U (IR-U, IR-U3-5, or IR-U/LMDF) for additional 24 hrs. they became more mature and could function better as APC. This was concluded from the increase in CD1d, CD14, CD40, CD80, CD86, CD95, ER-MP58, R4/80, RB6 8C5, E-cad and MHC II cell surface markers (FIG. 55).

Figure 56:
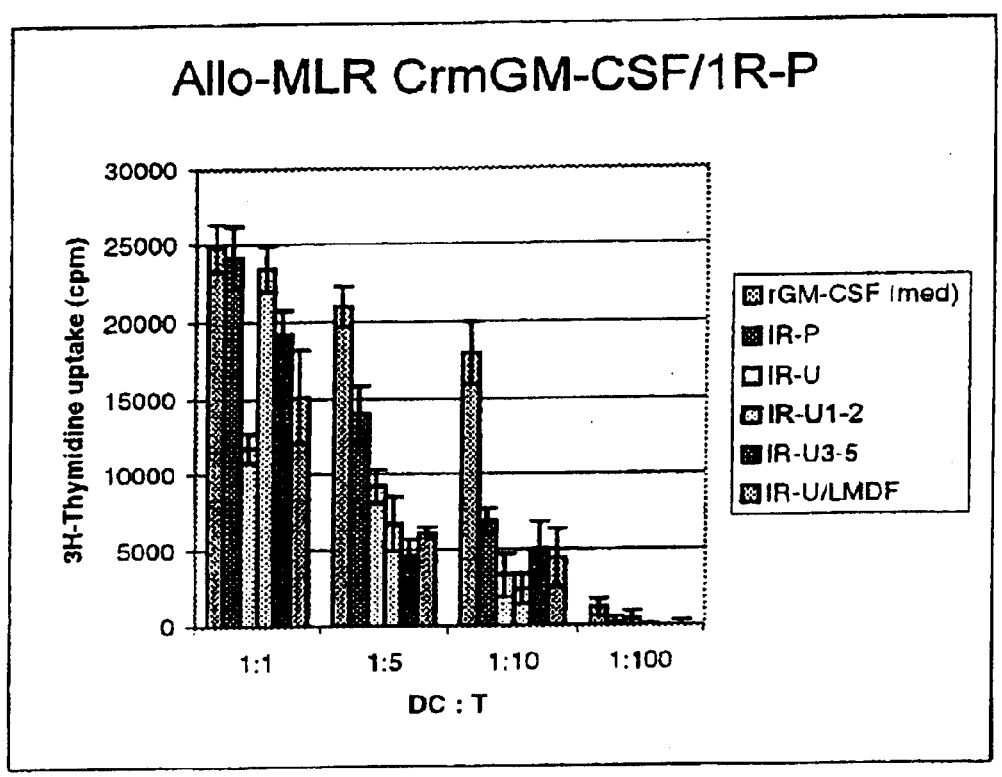

Allo-MLR Results:

In order to test the immunosuppressive activity of IR for instance for transplantation purposes, we also performed allo-MLR with BM cells from 9-wk-old female BALB/c as mentioned above and cultured with GM-CSF (20 ng/ml) and IR (IR-P, 300 I/ml; IR-U, 300 mg/ml; IR-U3–5, 300 mg/ml; IR-U/LMDF, 300 mg/ml) for 7 days. After 7 days these DC were irradiated (2,000 rad) and co-cultured in various ratios with splenic CD3+ cells isolated from 9-wk-old female C57BL6Ly. T cell proliferation was measured via [$^3$H]TdR incorporation during the last 16 hrs in culture. Proliferation data shows that IR treated DC in all DC versus T cells ratios tested are able to suppress proliferation (FIG. 56).

Anti-shock Activity of IR-U/LMDF, IR-P3, IR-A3:

Lower molecular weight fractions of IR obtained by purification method 2 (IR-U/LMDF), also had anti-shock activity (FIG. 57) and mice treated with this fraction remained alive. We also tested all three fractions obtained from the superdex™ column, IR-U/LMDF, IR-P3, and IR-A3, for anti-shock activity. The method for this activity screening is mentioned elsewhere in this document. Our results showed that all three fractions from the superdex™ column and IR-P3 had anti-shock activity, while IR-A3 had low to moderate activity (data not shown).

Figure 100:
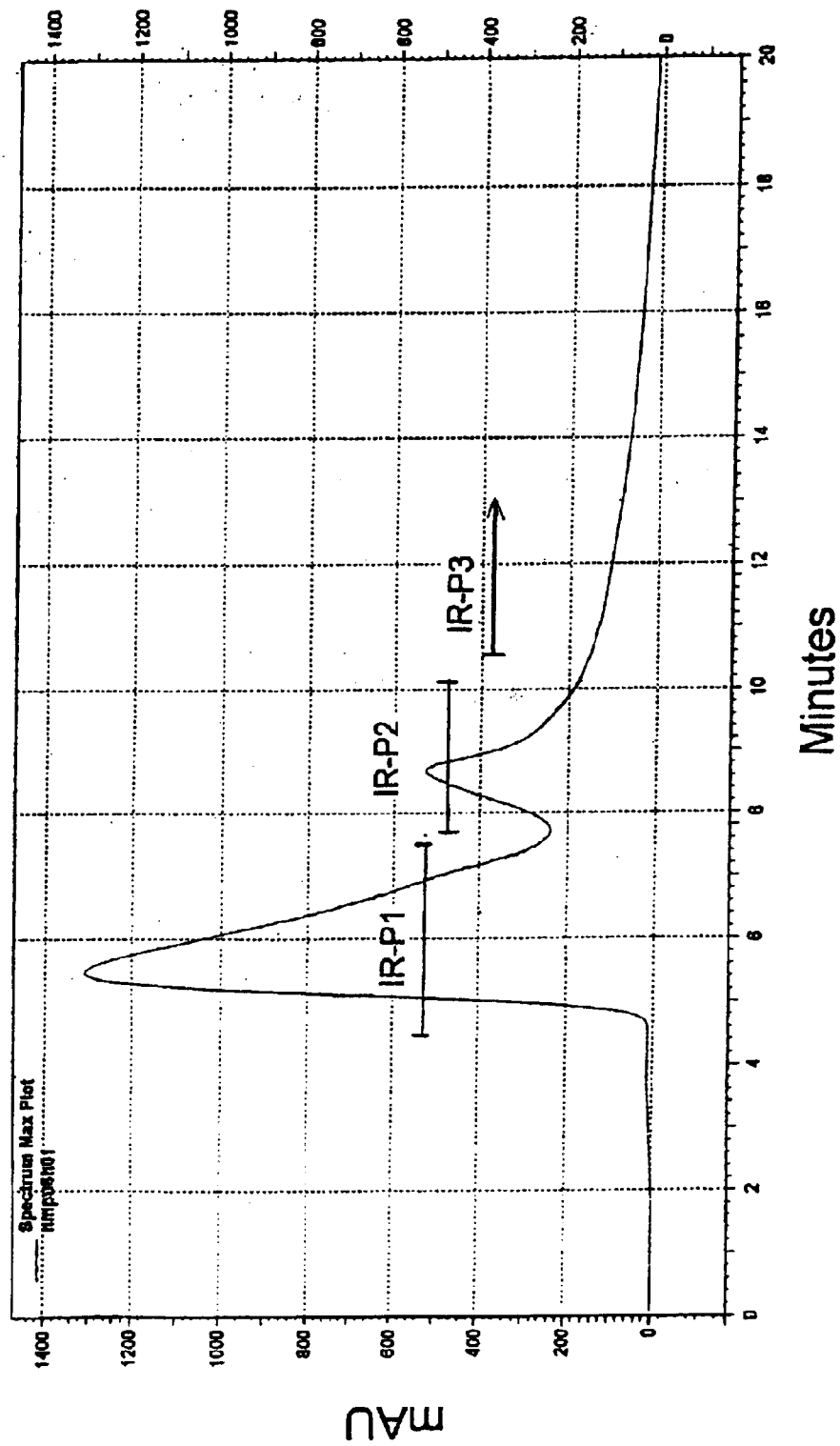

Purification by Method 3:

FIG. 100. shows macrosphere GPC 60 Å chromatogram of a IR-P sample.

Three selected areas were fractionated, IR-P1 which elutes apparently with molecular weight of >10 kDa, IR-P2 which elutes apparently with molecular weight between the 10 kDa–1 kDa, and IR-P3 which elutes aparently with molecular weight <1 kDa. All these activities were tested for at least anti-shock activity and they all had anti-shock activity (shown elsewhere in this document).

Figure 101:
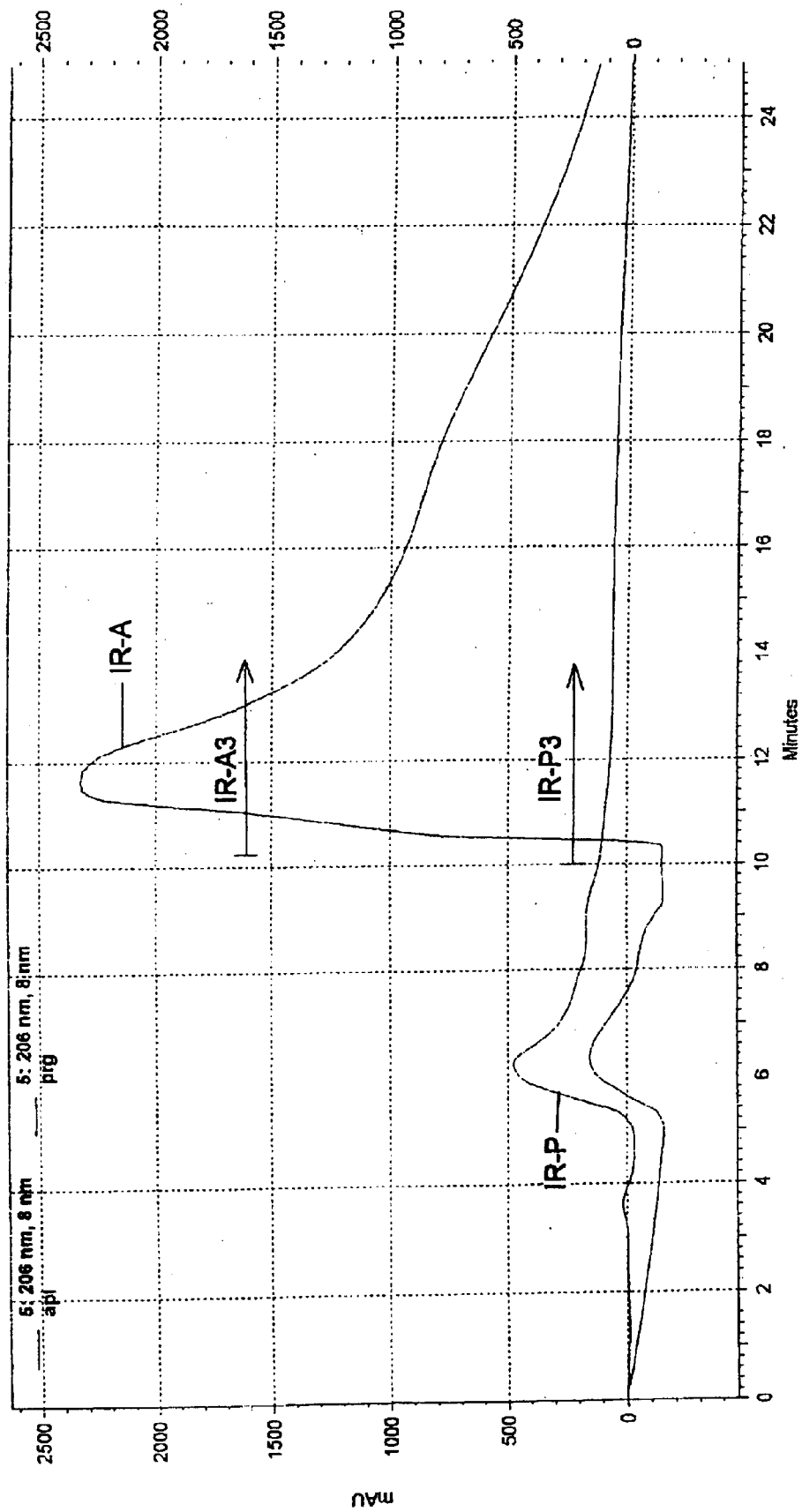

FIG. 101. shows macrosphere GPC 60 Å chromatrogram of IR-P and IR-A sample (500 IU of each sample was injected with a same injection volume). The results revealed that IR-A contains large amount of IR-A3 fraction as compare to IR-P3 fraction in the IR-P sample. We have tested same amount of IR-A and IR-P for their anti-shock activity. The results revealed that IR-A had low to moderate anti-shock activity compared to IR-P (result not shown).

Figure 97:
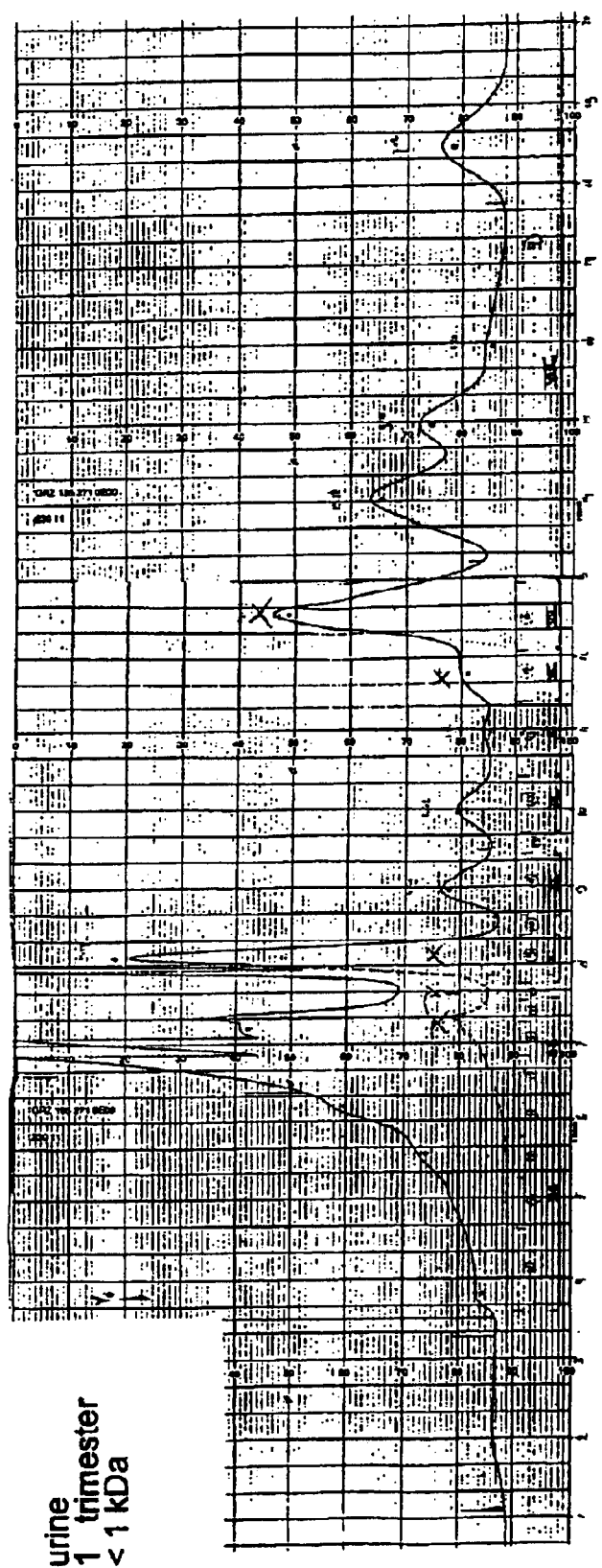

Purification by Method 4:

Pooled urine was obtained from pregnant women during the first trimester of their pregnancy. After desalting on a FDC column in a FPLC system and employing 50 mM ammonium bicarbonate as the running buffer, the pooled low molecular weight fractions (LMDF; <5 kDa) were lyophilized. The LMDF sample (13–17 mg) was suspended and applied on a Bio-Gel P-2 column using water for the elution. The elution profile was segregated into 8 different peaks and the poled fractions were tested for bioactivity in the LPS-induced septic shock (method mentioned elsewhere in document). Based on the inhibition of LPS shock the activity was located in fractions Ic ("?"), II, III,VI, and VII. These peaks comprised elution volumes between 40–45 ml (peak Ic "?"), 45–50 ml (peak III), 60–65 ml (peak VI) and 65–70 ml (peak VII) (FIG. 97).

Figure 98:
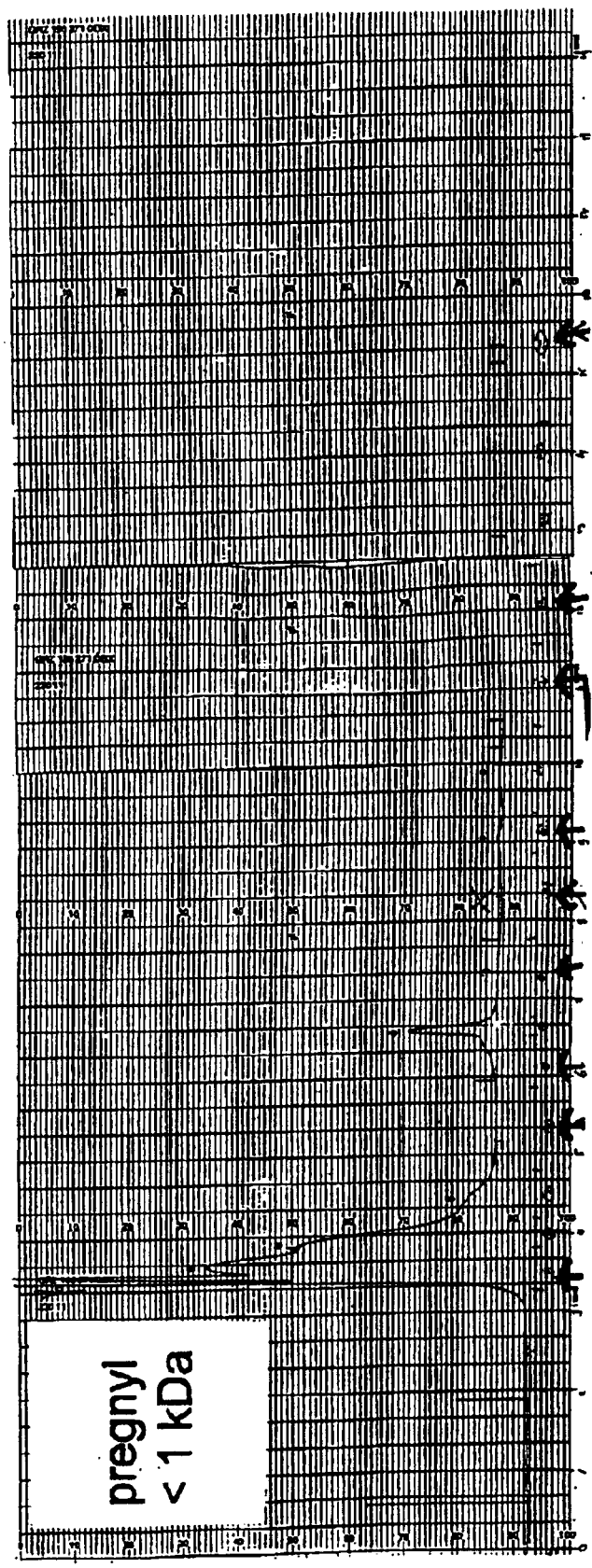

A sample of IR-P (Pregnyl) was applied on the Macroshere GPC 60 Å column and eluted with ammonium bicarbonate. The third peak fraction (FIG. 100) (IR-P3) was pooled and applied on the Bio-Gel P-2 column and eluted with water into various peaks. Testing for activity in the LPS shock model revealed that the activity was located in the fractions located between the elution time of 7 and 9 hours (FIG. 98).

Figure 99:
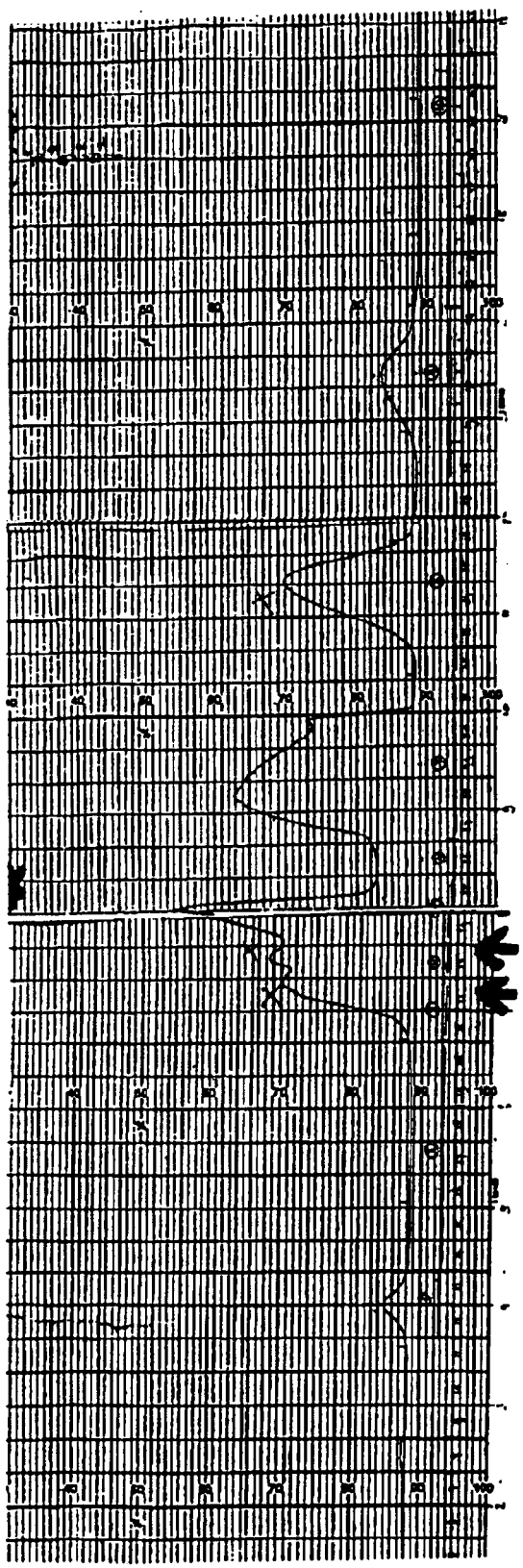

A sample of IR-A (APL) was applied on the Macroshere GPC 60 Å column and eluted with ammonium bicarbonate. The third peak fraction (IR-A3) was pooled and applied on the Bio-Gel P-2 column and eluted with water into various. Testing for activity in the LPS shock model revealed that the activity was located in the peaks 2, 3 and 7. These peaks comprised elution volumes between 103–115 ml (peak 2), 115–120 ml (peak 3) and 160–180 ml (peak 7) (FIG. 99).

In-vivo Anti-sepsis or Septic Shock Effect of IR

Figure 20:
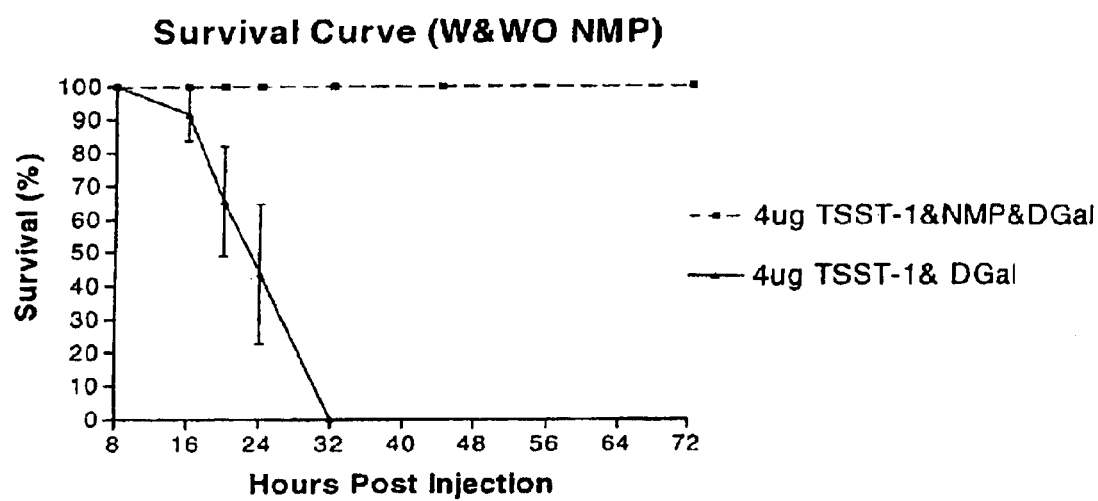

Survival Curve: The most striking results from this experiment are the black and white difference between those animals treated with IR-P prior to TSST-1 and D-Gal treatment versus those that were not (FIG. 20.). This is evident in the survival curve obtained from this experiment. While a 4 µg dose of TSST-1 coupled with D-Galactosamine sensitisation was 100% lethal by 32 hours; animals pretreated with IR prior to TSST-1 exposure did not succumb to the effects of lethal toxic shock.

LPS treated Balb/c mice and SJL mice revealed different sensitivity to LPS. 600 µg LPS was 100% lethal by 48 hours and 36 hours in Balb/c and SJL, respectively, while IR pre-treated Balb/c and SJL mice remained alive. We also pre-treated Balb/c mice with IR-U fractions namely, IR-U1, IR-U2 and IR-U3-5[pooled] and then treated with LPS. These experiments showed that IR-U1 and IR-U1 pre-treated mice were very sick by 48 hours and were killed along with LPS group. However, mice treated with IR-U3-5 remained alive.

A group of Balb/c mice were treated twice with 700 IU IR-P after the injection of LPS. The control group mice (only LPS) were killed at 48 hours time point because of their severe sickness. Mice treated with IR-P remained alive, except two (2/6) mice were killed at 60 hours time point.

Illness Kinetics: Visible signs of sickness were apparent in all of the experimental animals, but the kinetics and obviously the severity of this sickness were significantly different; like IR-P pretreated Balb/c mice group did not exceed the sickness level 2 in TSST-1 exotoxin model (FIG. 21.) and also in LPS endotoxin model in addition to IR-U3-5 pre-treated mice. IR-P pre-treated SJL mice and IR-P post-treated Balb/c mice in LPS model did not exceed the sickness level 3. All mice in both models were killed when they exceed the sickness level 5.

Figure 12:
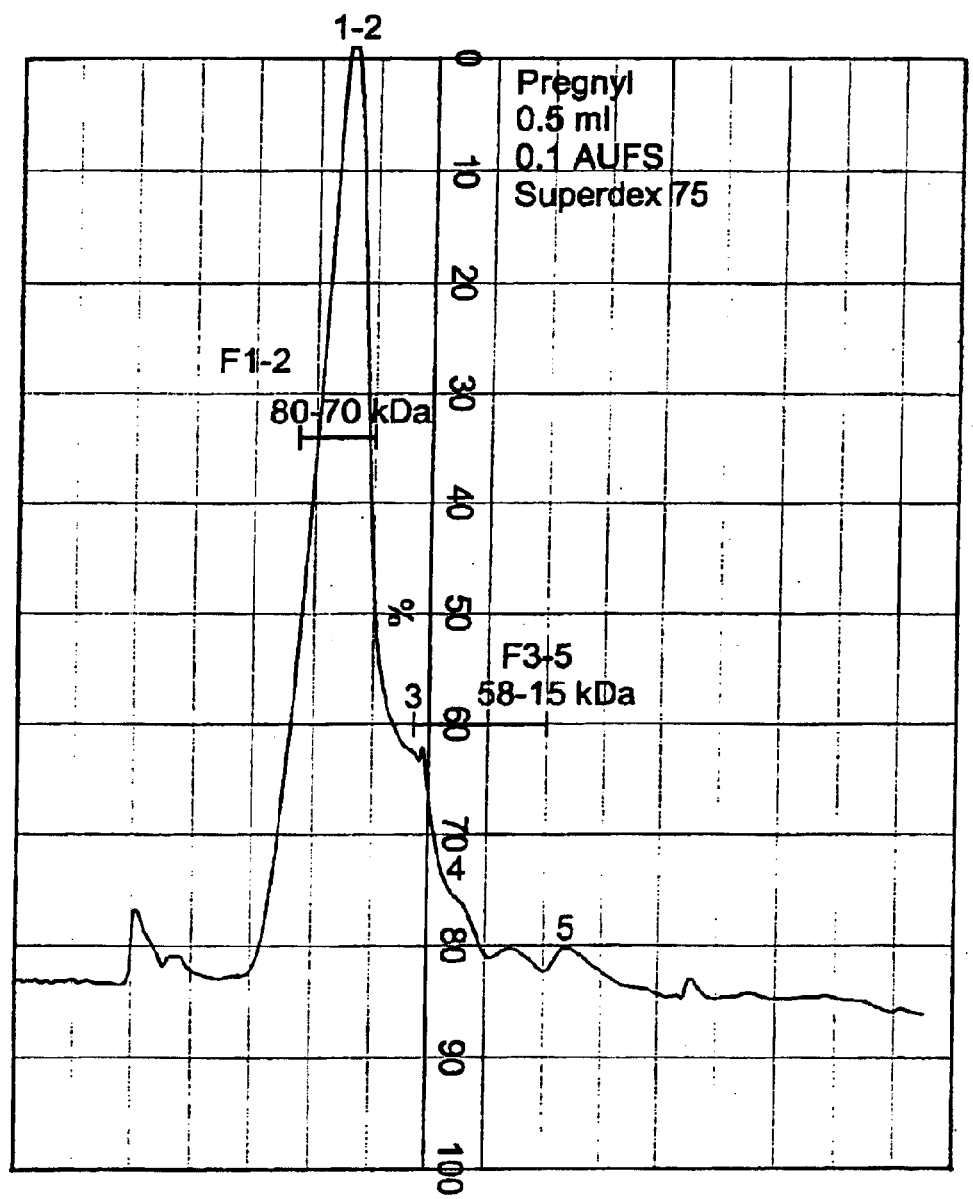

Shock Induced Weight Lose in TSST-1: IR pretreatment also resulted in significantly reduced weight loss of survivors of toxic shock. Weight loss data from this experiment was combined with that from another experiment which followed identical illness kinetics (data not shown), but resulted in two survivors of the 4 ug TSST-1 &D-Gal without IR pre-treatment group. (FIG. 12.).

When this weightless data was statistically analysed using a 2-sample T-test (using Minitab statistical software, version 11.21) significant differences (P(HO:$\mu1=\mu2$)<O05) in weight loss were observable at 32 and 48 hours despite low n numbers, indicating an even higher possible significance if n were increased:

Two sample T for weight loss at 32 hours

Two sample T for weight loss at 32 hours
(group 1 = TSST1&D-Gal; group 2 = T&D with IR pre-treatment)

| group | N | Mean | StDev | SE Mean |
|---|---|---|---|---|
| 1 | 4 | 4.75 | 1.79 | 0.89 |
| 2 | 6 | 1.28 | 2.22 | 0.91 |

95% CI for $\mu1-\mu2$: (0.45, 6.48)
T-Test $\mu1-\mu2$ (Vs not =): T=2.72 P=0.030 DF=6

Two sample T for weight loss at 48 hrs
(group 1 = TSST1&D-Gal; group 2 = T&D with IR pretreatment)

| group | N | Mean | StDev | SE Mean |
|---|---|---|---|---|
| 1 | 3 | 10.05 | 2.25 | 1.3 |
| 2 | 6 | 3.49 | 4.41 | 1.8 |

95% CI for $\mu1-\mu2$: (1.1/12.0)
T-Test $\mu1-\mu2$ (Vs not =): T=2.95 P=0.026 DF=6

WBC and Platelets Counts: White-blood cell levels in blood (FIG. 23) were significantly higher in TSST- and D-Gal alone treatment (bar #2) versus WBC counts in regular mice (bar #1) and IR-P pre-treated mice (bar #3. This indicates, as expected, a higher level of immune activation in the mice suffering from lethal toxic shock. There is still a normal level of WBC in the IR-P group, such a finding also fits our other results, as this group did not show severe visible signs of illness.

Blood platelet counts (FIG. 24) were also reduced in TSST-1 D-Gal treated mice. Elevated platelet counts were seen in IR-P treated mice.

Transplantation Results:

A major goal of transplantation research is the development of strategies to inhibit allograft rejection and even better, to induce allospecific tolerance. For this purpose, animal models have been widely used and it has become clear that skin allograft rejection may be one the most difficult to prevent.

MHC-disparate graft loss is inevitable if alloreactivity is not suppressed by immunosuppressive agents. Currently, immunosuppressive protocols are based upon the combined use of multiple immunosuppressive agents which may potentially interfere with distinct steps of the rejection process, including antigen recognition, T cell cytokine production, cytokine activity and T cell proliferation, macrophages, NK cells and cytotoxic T cell. In experimental settings many drugs and monoclonal antibodies mAb) have been and are being evaluated for their immunosuppressive capacity. Among these are mizorbine, RS-61443, 15-deoxyspergualin, brequinar sodium and mAb against LFA-1, ICAM-1, CD3, CD4 and IL-2R. Cytokines produced by many cell types, such as T cells, macrophages and NK cells, may influence the rejection process. Because of their central role in graft rejection, CD4+ T cells and the cytokines they produce have been studied widely in rejection and acceptance of allografts. CD4+ T lymphocytes can be subdivided into at least two subsets, Th1 and Th2 cells, based on their cytokine production pattern. Th1 cells, which produce IL-2, IFN-gamma and TNF-beta, play a role in delayed type hypersensitivity (DTH) reactions and cellular cytotoxicity, whereas Th2 cells, which produce IL-4, IL-5, IL-6 and IL-10, are effective stimulators of B cell differentiation and antibody production. These two Th subsets can regulate each others proliferation and function. While IFN-gamma inhibits Th2 cell proliferation and antagonizes IL-4 effects, IL-10 inhibits Th1 cytokine production. There are indications for the existence of regulatory T cells which can also regulate these two subsets. Graft rejection is thought to be mediated by Th1 cells, that may stimulate DTH and CTL activity. On the other hand, suppression of alloreactive Th1 cells may lead to graft acceptance.

Immunosuppression may be achieved by neutralizing pro-inflammatory cytokines by administration of anti-cytokine mAb or soluble cytokine receptors. Alternatively, "skewing" of T cell differentiation towards one of the Th subsets can be achieved by varying the cytokine environment. For example, IFN-gamma (Th1, NK cells) and IL-12 (macrophages, B cells) promote Th1 cell differentiation, whereas IL-4 (Th2) enhances Th2 cell development. Changing the in vivo cytokine environment by anti-cytokine mAb or cytokines, may have a similar effect. Moreover, induction of regulatory cells like Th3 and Tr1, and like DC1 and QC2 also reduce transplant rejection and induce tolerance for graft.

Figure 95:
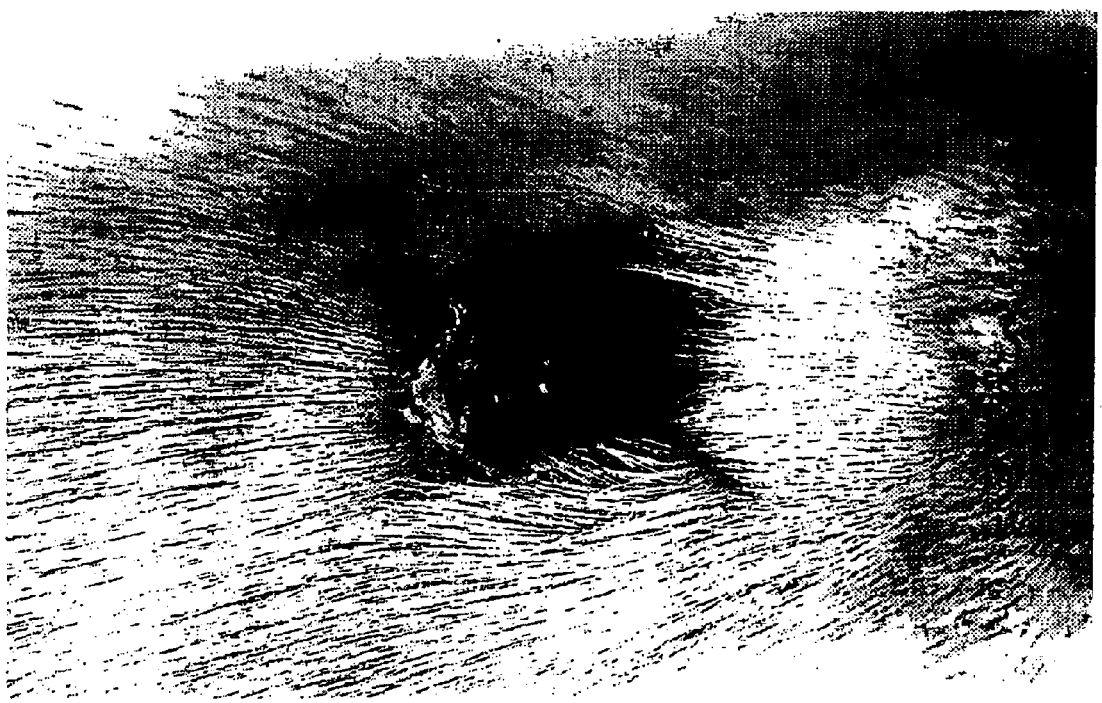
Figure 96:

Results: Treatment of BALB/c recipients with IR-P prolonged C57BL/6 skin graft survival as compared to the untreated control group. The control recipients rejected skin graft within 12 days (FIG. 95) while IR-P treated recipients were able to prolonged the graft till 22 days after transplantation (FIG. 96). FIGS. 95 and 96 show one such prolonged graft (picture taken on day 19) due to the IR-P treatment and a rejected graft from the control mice.

Figure 60:
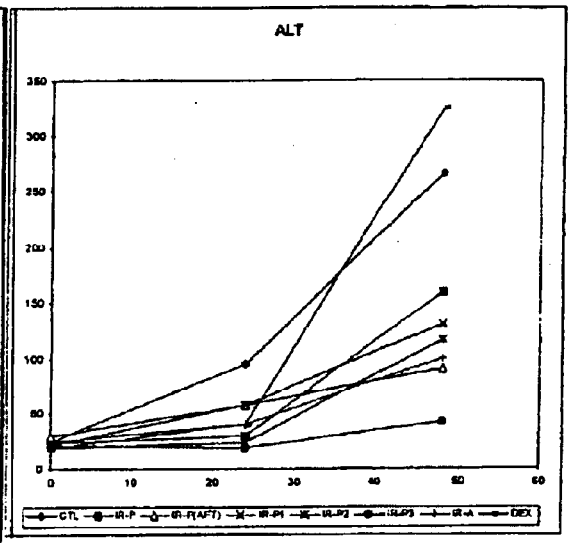
Figure 77:
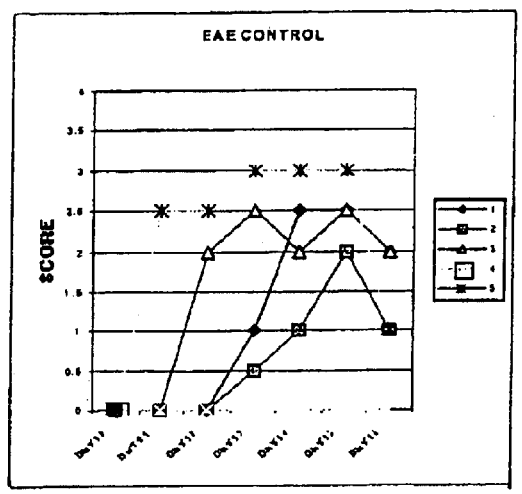
Figure 78:
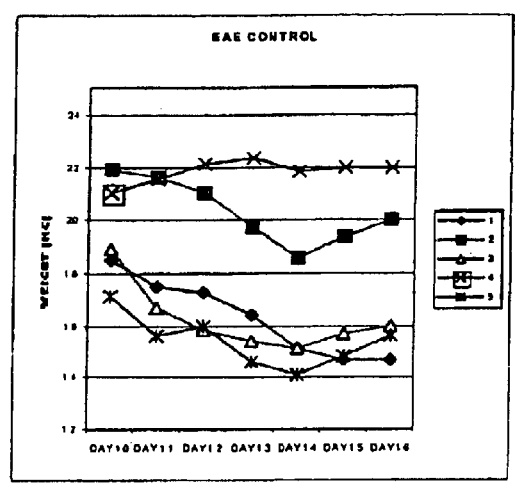
Figure 79:
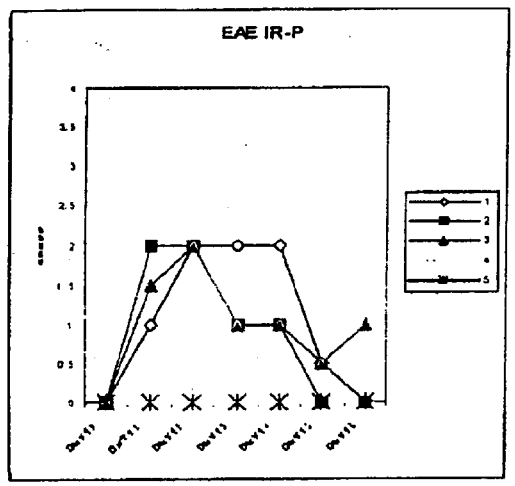

EAE Results:

Mice treated with PBS only lost weight during the first three weeks (FIG. 77). These mice had all clinical signs of EAE of at least 2 and longer duration of the disease, except for one mice which remained resistance to disease during the whole experiment (FIG. 78). In IR treated mice group there was less weight lost observed during the experiment (FIG. 79) and two mice were free of disease during the experiment. Sick mice in this group had maximum clinical scores of 2 and had short duration of the disease and recovered faster from EAE symptoms then PBS treated group (FIG. 60).

Results on Shock:

IR treated mice are resistant to LPS-induced shock: To determine the effect of high-dose LPS treatment in IR treated mice, BALB/c mice (n-30) were injected intraperitoneally with LPS (150 mg/kg) and survival was assessed daily for 5 days. PBS-treated BALB/c mice succumbed to shock between days 1 and 2 after high-dose LPS injection, with only 10% of mice alive on day 5 (FIG. 55). In constrast, 100% of IR-P, or its fractions IR-P1 or IR-P3, treated mice were alive on day 5 (P<0.001) (FIG. 58), while groups of IR-P2, IR-A and Dexamethasone treated mice demonstrated around 70% of survivers (FIG. 56).

Figure 58:
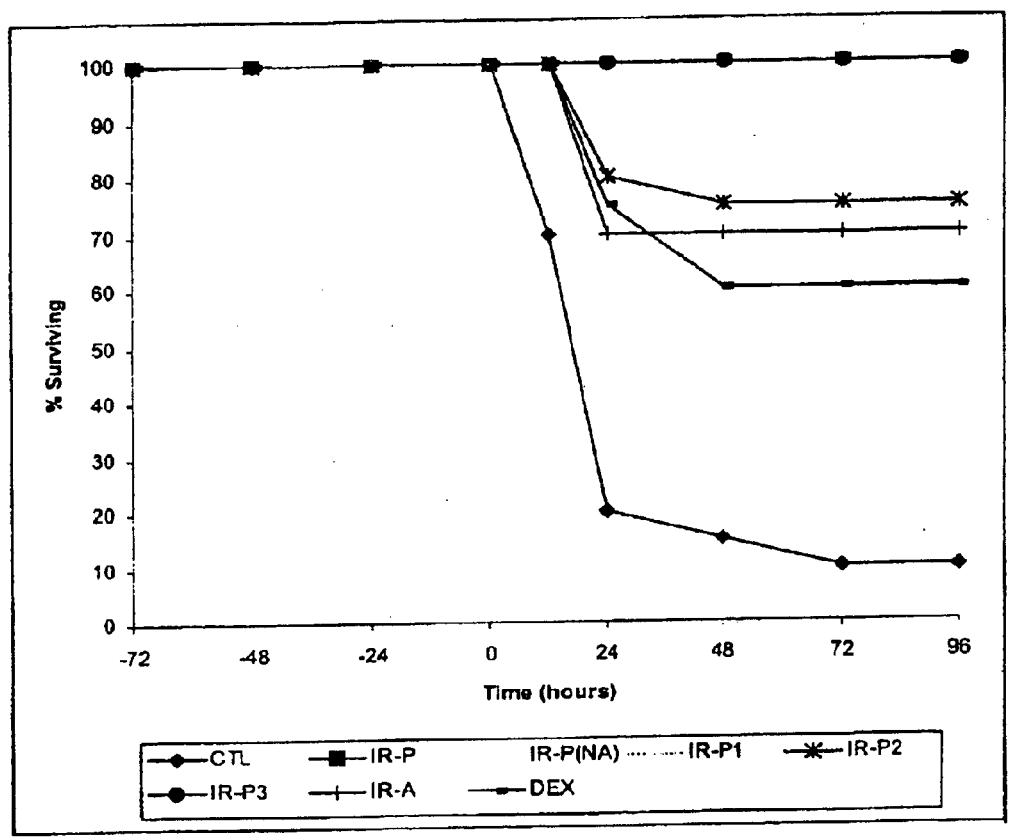
Figure 59:
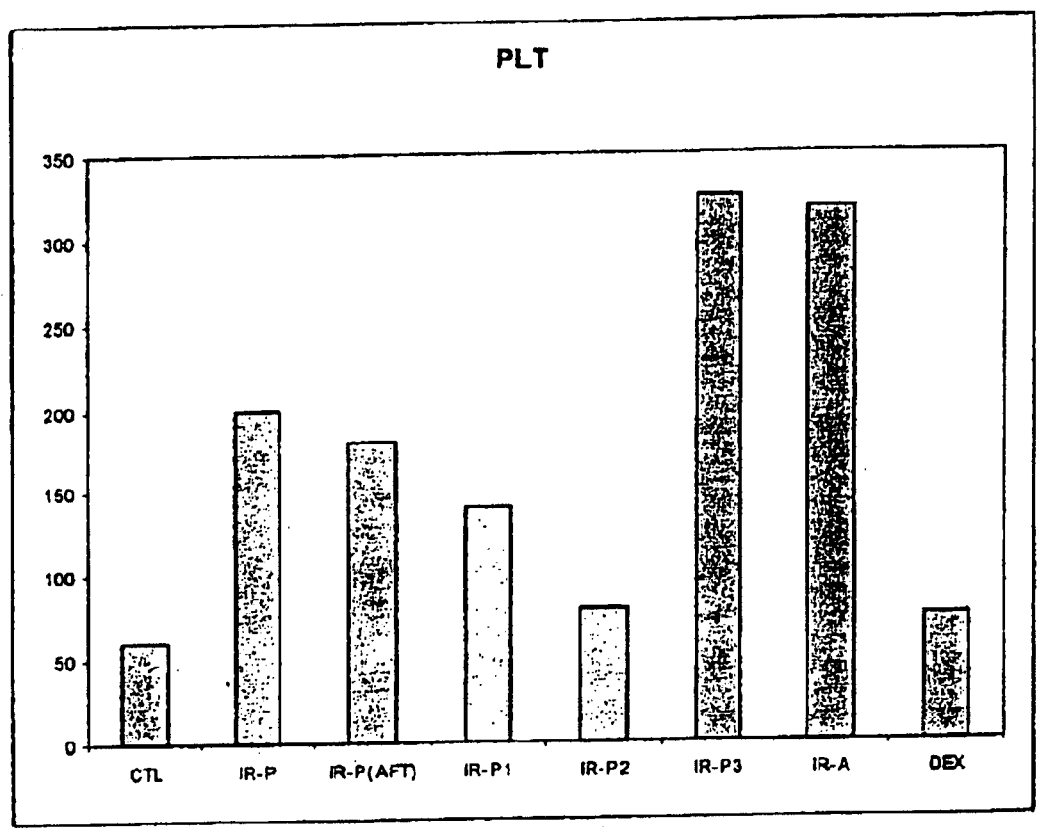
Figure 61:
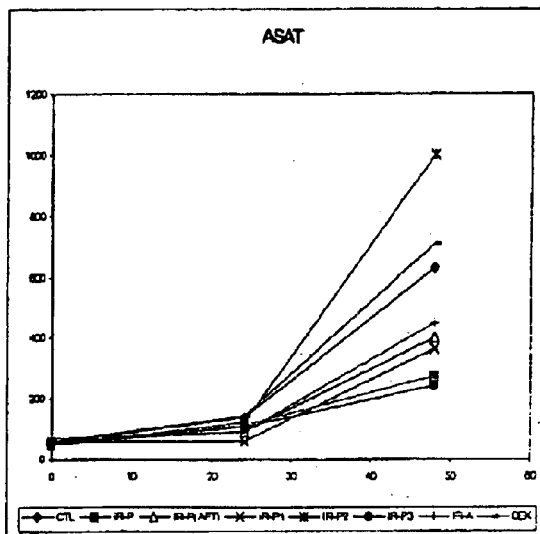
Figure 62:
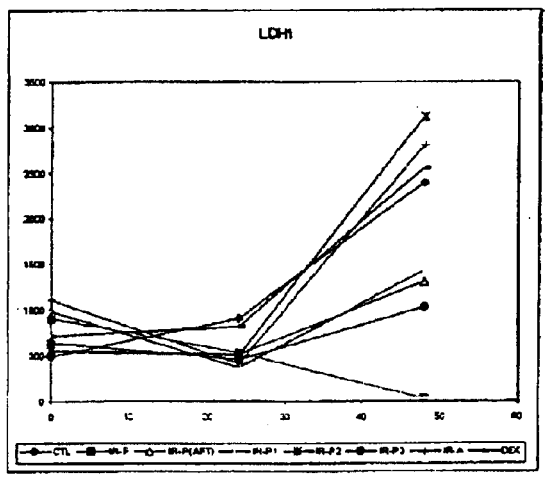
Figure 63:
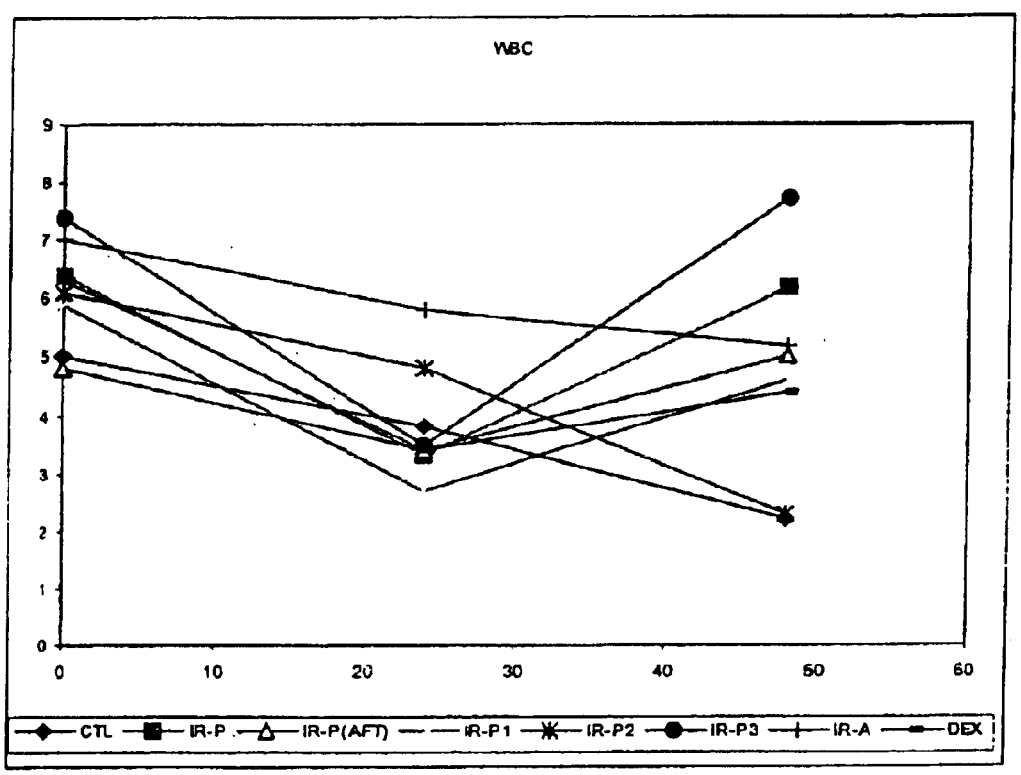

Blood test: Major manifestations of systemic response on LPS in shock is severe inflammation in organs, leading to organ failure or organ system dysfunction, initially in liver. Therefore, we measured enzymes like ALAT, ASAT, LDH1 as well as WBC and platelets. FIG. 59 shows that IR-A, IR-P and its fraction IR-P1, IR-P3 have all platelets counts within normal range 1100–300×$10^9$/ml., while control, IR-P2 and Dexamethasone treated mice have platelets counts below normal range. FIGS. 60–62 show that mice treated with IR-A, IR-P and its fraction IR-P1, IR-P2 or IR-P3 had relatively low levels of ALAT, LDH1 and ASAT enzymes in the plasma as compared to control and dexamethasone treated mice. These enzymes were present in higher concentrations in blood during shock due to organ damage. These results are consistent with our surviving results (FIG. 58). In addition, during shock low numbers of WBC were found in blood because of their migration to the sites of inflammation. Our results in FIG. 63 show that mice treated with IR-A, IR-P and its fractions have moderate to normal levels of WBC at t=48 hours than control and dexamethasone treated mice, suggesting weaker inflammatory responses in IR treated mice.

Ex Viva NOD/LTJ Results:

FIG. 64 shows inhibition of IFN-gamma production in Th1 polarisation assay with CD4+ cells isolated from NOD mice treated with IR-P or IR-P3 in combination with rhCG, while moderate inhibition was found in Th1 polarisation by rhCG and IR-P3 alone. This shows that treatment with IP-P3 in combination with rhCG gives massive inhibition of Th1 outgrowth in NOD mice. This suggests that IR-P3 fraction needs rhCG for it maximum inhibition of the Th1 subset.

FIG. 65 shows inhibition of IFN-gamma production in anti-CD3 stimulated spleen cells obtained from NOD mice treated with IR-P, IR-P1, IR-P2 or with IP-P3 in combination with rhCG as compared to PBS treated mice. rhCG and IR-P3 separately did not have the same effect as in combination. This suggests again that IR-P3 fraction needs rhCG for its IFN-gamma inhibition.

Figure 66:
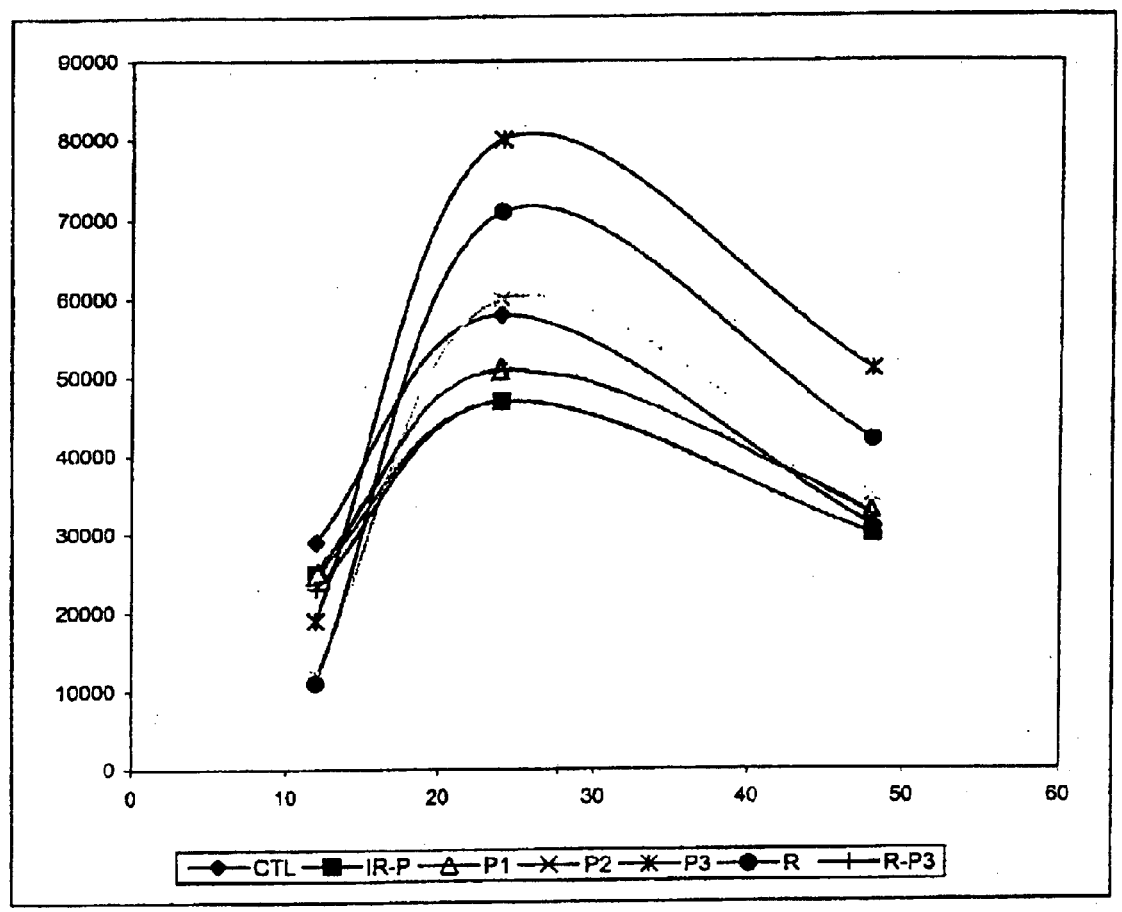

FIG. 66 shows anti-CD3 stimulated proliferation at different time points (t-12, 24, 48 h) of spleen cells obtained from NOD mice treated with IR-P, its fractions, rhCG, or IR-P3 in combination with rhCG. Again the results are consistent with the previous IFN-gamma inhibition (FIG. 65). Here, IR-P3 fraction also needed rhCG for its inhibitory effect on anti-CD3 induced proliferation of spleen cells from in vivo treated NOD mice.

Figure 67:
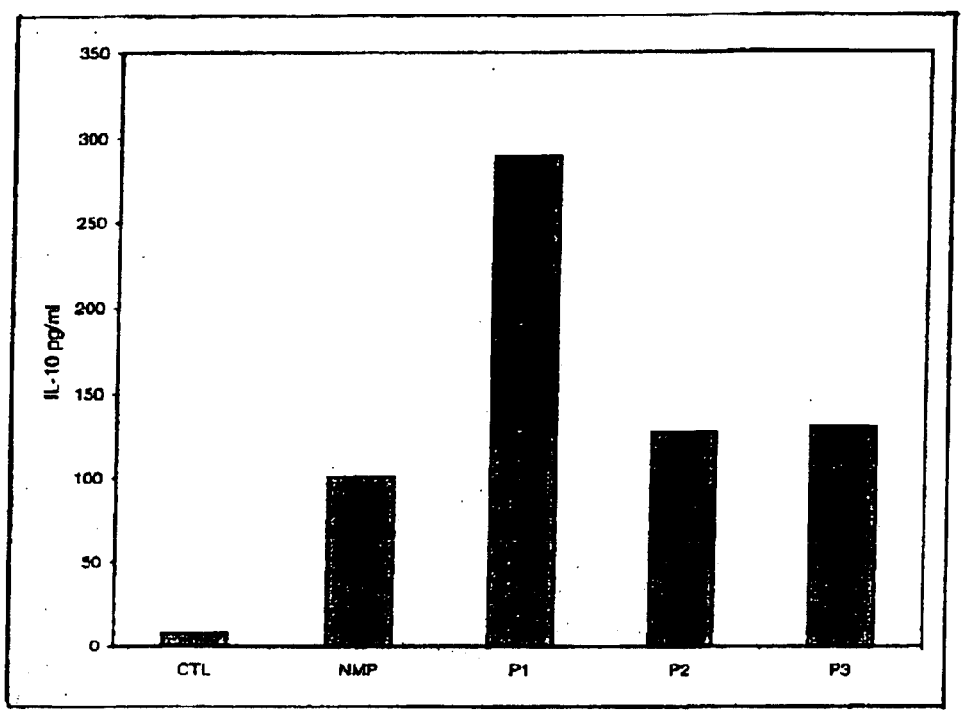

FIG. 67 shows that IR-P and its fractions promote IL-10 production of anti-CD3 stimulated spleen cells from treated NOD mice as compared to PBS treated mice. FIG. 68 shows that IgG2a production is not inhibited by in vivo treatment of NOD mice with IR-P2 or rhCG, while IR-P, IR-P1, IR-P3 and IR-P3 in combination with rhCG did inhibit the IgG2a production.

Since, IR-P3 in combination with rhCG has the same characteristics as IR-P, it is thinkable that this combination can also be used for the induction of pregnancy, IVF, prevention of abortions or related problems.

STZ Model

The determining event in the pathogenesis of diabetes I is the destruction of insulin-producing pancreatic beta cells. There is strong evidence that the progressive reduction of the beta-cell mass is the result of a chronic autoimmune reaction. During this process, islet-infiltrating immune cell, islet capillary endothelial cells and the beta cell itself are able to release cytotoxic mediators. Cytokines, and in particular nitric oxide (NO), are potent beta-cell toxic effector molecules. The reactive radical NO mediates its deleterious effect mainly through the induction of widespread DNA strand breaks. This initial damage presumably triggers a chain of events terminating in the death of the beta cell.

Diabetes induced in rodents by the beta-cell toxin streptozotocin (SZ) has been used extensively as animal model to study the mechanisms involved in the destruction of pancreatic beta cells. SZ is taken up by the pancreatic beta cell through the glucose transporter GLUT-2. This substance decomposes intracellularly, and causes damage to DNA either by alkylation or by the generation of NO. The appearance of DNA strand breaks leads to the activation of the abundant nuclear enzyme poly(ADP-ribose) polymerase (PARP), which synthesizes large amounts of the (ADP-ribose) polymer, using NAD+ as a substrate. As a consequence of PARP activation, the cellular concentration of NAD+ may then decrease to very low levels, which is thought to abrogate the ability of the cell to generate sufficient energy and, finally, to lead to cell death.

Reactive radicals also play an important role in the pathogenesis of many diseases like nephropathy, obstructive nephropathy, acute and chronic renal allograft rejection, auto-immune diseases (like SLE, rheumatoid arthritis, diabetes, MS) AIDS, diseases related to angiogenesis, atherosclerosis, thrombosis and type II diabetes mellitus. For instance, recently increased oxidative damage to DNA bases has been shown in patients with type II diabetes mellitus which contribute to the pathogenesis and complications of diabetes. We tested whether IR has also the capacity to delay the induction of STZ induced diabetes and thus also has effect on cellular reactive radical forming and protection.

Figures 69, 70:
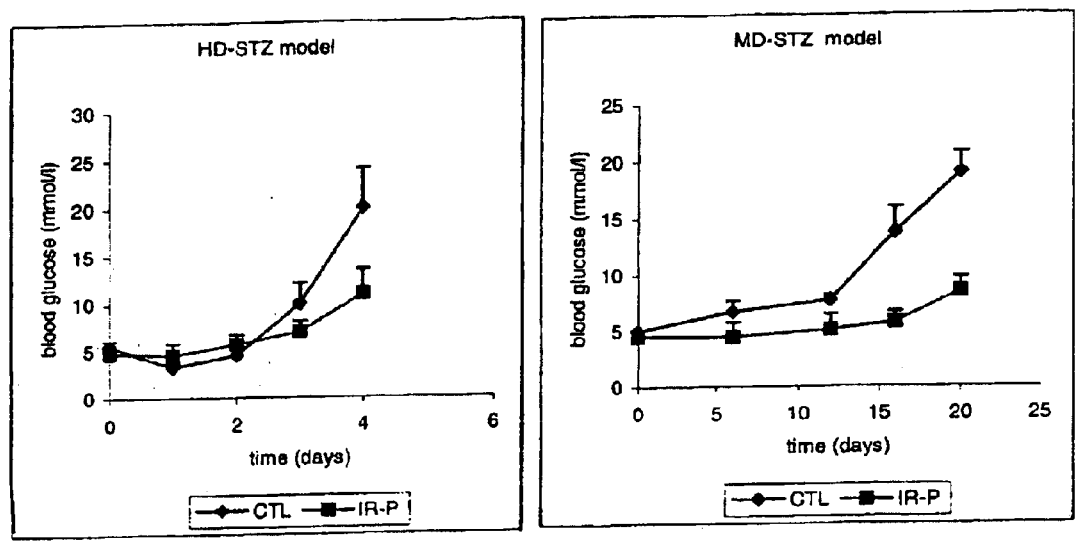

In HD-STZ model the induction of diabetes is due to direct effect on beta cells of pancreatic tissue by inducing activation of PARP. Consequently, decrease of NAD+ and abrogation of the ability of the cell to generate sufficient energy finally leads to the cell death. This suggests that there is not any immunological component involved in this process. In contrast, in the MD-STZ model strong immunological components are present. FIGS. 69 and 70 show that IR-P treatment is able to delay the induction of diabetes in both models. The mechanism behind this delay is probably of different nature.

Human Studies

The immune system has a remarkable capacity to maintain a state of equilibrium even as it responds to a diverse array of microbes and despite its constant exposure to self-antigens. After a productive response to a foreign antigen, the immune system is returned to a state of rest, so that the numbers and functional status of lymphocytes are reset at roughly the preimmunization level. This process is called homeostasis, and it allows the immune system to respond effectively to a new antigenic challenge. The size and the repertoire of the preimmune lymphocyte subpopulations are also closely regulated, as new emigrants from the generative lymphoid organs compete for "space" with resident cells. Lymphocytes with receptors capable of recognizing self-antigens are generated constantly, yet normal individuals maintain a state of unresponsiveness to their own antigens, called self-tolerance.

In autoimmune diseases, the immune system inappropriately recognizes "self," which leads to a pathologic humoral and/or cell-mediated immune reaction. In a normal, nonautoimmune state, self-reactive lymphocytes are deleted or made unresponsive to peripheral self ligands.

Populations of potentially autoreactive cells can be demonstrated, yet appear not to give rise to apathogenic autoimmune reaction to their ligands. A picture of autoimmune disease is emerging wherein these autoreactive cells are activated through molecular mimicry, given that T cell receptor (TCR) interactions can be degenerate and T cells can be activated by a diversity of ligands (1, 2). There is evidence that under appropriate conditions activation of autoreactive T cells is facilitated by the induction of cytokines and the up-regulation or particular costimulatory molecules (e.g., CD80/CD86 and CD40), leading to autoimmunity.

When the immune system mistakes self tissues for nonself and mounts an inappropriate attack, the result is an autoimmune disease. There are many different autoimmune diseases. Some examples are Wegener's granulomatosis, multiple sclerosis, type 1 diabetes mellitus, and rheumatoid arthritis. Moreover, infection can also induce immune responses that lead to the induction of immune diseases, while infection itself is not dangerous to host. For example, the role of Tubercle bacilli in Tuberculosis, in which the immune system reacts to agressively on Tubercle bacilli resulting in inflammatory illness and tissue destruction due to own immune response. Same is also true, for example, for lepra tuberculoid.

Autoimmune diseases can each affect the body in different ways. For instance, the autoimmune reaction is directed against the brain in multiple sclerosis and the gut in Crohn's disease. In other autoimmune diseases, such as Sjögren disease and systemic lupus erythematosus (lupus; SLE), affected tissues and organs may vary among individuals with the same disease. Many autoimmune diseases are rare. As a group, however, they afflict many people in Western societies.

Many autoimmune diseases are more prevalent in women than in men. The sexual dimorphism covers a broad range of autoimmune disorders, ranging from organ-specific (such as Graves's disease) to generalized such as SLE. In MS, there is a female-to-male preponderance approaching 2:1 to 3:1. The reasons for the sex bias in MS and other autoimmune diseases are unclear but many include factors as sex-related differences in immune responsiveness to infection, sex steroid effects, and sex-linked genetic factors. It is recognized that MS, Sjögren, SLE, and RA are different diseases and probably differ in etiology.

However, the common link is the overwhelming prevalence of these diseases in women. Considering that each of these diseases is autoimmune, the effects of sex hormones and gender may be similar, making a comparison of these diseases useful. Autoimmune diseases strike women, particularly during their working age and their childbearing years. However, the clinical course of these diseases are surprisingly less severe or even remission is seen during pregnancy.

During pregnancy, women undergo immunologic changes consistent with weakening of cell-mediated immunity (Th1 responses) and strengthening certain components of humoral immunity (Th2 responses). This Th2-biased like responses by the maternal system during pregnancy introduces a status of temporary immunosuppression or immunomodulation, which results in suppression of maternal rejection responses against fetus but maintain, or even increase, her resistance to infection. In addition, decreased susceptibility to some autoimmune diseases, especially Th1-cell mediated immune disorders have been also observed. For instance, approximately 77% of women with rheumatoid arthritis (predominantly a Th1-cell mediated autoimmune disorder) experience a temporary remission of their symptoms during gestation, which are apparent from the first trimester in the majority of cases. Hence, clinical improvement during gestation in Th1-cell mediated autoimmune diseases should probably be related to physiologic immune changes during the early pregnancy.

Since our IR is able to inhibit the development of autoimmune disease in animal models such as NOD and EAE, we treated few patients with immune diseases. All patients were treated because of refractory disease and after informed consent.

PATIENT 1: Wegener's Granulomatosis

Wegener's granulomatosis is an autoimmune vascular disease that can affect both men and women; and although it is more common in persons in their middle age, it can affect persons of any age. The initial manifestations generally involve the upper and lower respiratory tract, with a chronic, progressive inflammation. The inflammation may form lumps or granulomas in the tissues or in the skin. It may progress into generalized inflammation of the blood vessels (vasculitis) and kidneys (glomerulonephritis). A restricted form of the disease that does not involve the kidneys may occur.

The vasculitis is the result of an autoimmune reaction in the wall of small and medium-sized blood vessels. Chronic vasculitis causes a narrowing of the inside of the blood vessel and can result in obstruction of the flow of blood to the tissues. This situation may cause damage to the tissues (necrosis).

Autoimmune diseases occur when these reactions inexplicably take place against the body's own cells and tissues by producing self-reactive antibodies. In Wegener's granulomatosis, an autoantibody is directed toward components in the cytoplasm of certain white cells. The cause of Wegener's granulomatosis remains unknown. Though the disease resembles an infectious process, no causative agent has been isolated. Anti-Neutrophilic Cytoplasmic Antibody (ANCA) is found in the majority of patients, and its level appears to correlate with the disease activity. Wegener's granulomatosis is a quite rare disease, especially in Europe and in dark people (africana, south-americans, asian people). The exact number of patients is not known, but a rough estimate is two new cases per million Americans per year, or about 500 new cases diagnosed every year in the United States. The disease can occur at any age; however, it has its peak in the 4th or 5th decade of life It effects males and females equally 85% of the patients are above age 19

The mean age of patients is 41 (current age range is 5–91)

97% of all patients are Caucasian, 2% Black and 1% are of another race

The symptoms of Wegener's granulomatosis, and the severity of these symptoms vary from one patient to another, although most patients first notice symptoms in the upper respiratory tract. A common manifestation of the disease is a persistent rhinorrhea ("runny nose") or other cold-like symptoms that do not respond to standard treatment, and that become progressively worse.

Rhinorrhea can result from sinus drainage and can cause upper respiratory obstruction and pain. Complaints include discharge from the nose, sinusitis, nasal membrane ulcerations and crusting, inflammation of the ear with hearing problems, cough, coughing of blood and pleuritis (inflammation of the lining of the lung).

Other initial symptoms include fever, fatigue, malaise (feeling ill), loss of appetite, weight los, joint pain, night sweats, changes in the color of urine, weakness. Mostly Wegener's patients experience not all of the above symptoms, and the severity of the disease is different with each patient. Fever is often present, sometimes resulting from bacterial infection in the sinuses. One third of patients may be without symptoms at the onset of the disease.

Laboratory tests are not specific for Wegener's granulomatosis and only suggest that that the patients has an inflammatory disease. Blood tests often show anemia (low red blood cell count) and other changes in the blood. Chest X-rays and kidney biopsy are important tools used in diagnosing Wegener's granulomatosis. For effective treatment, early diagnose is critical. Asymptomatic patients can be diagnosed by ANCA blood tests and CT scans of sinuses and lungs. It takes 5–15 months, on average, to make a diagnosis of Wegener's granulomatosis 40% of all diagnoses are made within less than 3 months, 10% within 5–15 years.

Other diagnositic tools are as follows;

Erythrocyte sedimentation rate is generally elevated

Complete blood count will often shows anemia, elevated white counts, elevated platelet counts Urinalysis is often considered as a screening test for kidney involvement 24-hour urine collection is used in certain patients to assess kidney function c-ANCA is characteristic, measuring Proteinase-3 antibodies Our initial results of treatment of patient1 with IR-P The patient was treated because of refractory disease and after informed consent.

Diagnosis: Wegener's granulomatosis based on sinal histopathology and cANCA test.

Case: A 34 year old male patient known with relapsing Wegener's granulomatosis for 5 years. This patient was treated with high dosage steroids, cyclosporine (5 mg/kg) and cyclophosphamide (1–2 mg/kg). Because of progressive disease in July 1998 he was treated with IR (pregnyl), 5000 I.U, s.c. daily.

FIG. 81 shows that before IR treatment the patient was immuno-compromised due to the high dosis of steriods. After IR treatment the levels of T-lymphocytes (CD4. CD8) were increased and within normal range, except for B cells. We also measured cytokines in LPS and PMA/Ca stimulated PBMC obtained from patient during the IR treatment. We observed that LPS stimulated PBMC produced more TNF-alpha, IL-10 and IL-12 during treatment (FIG. 82a), while PMA/Ca stimulated PBMC produced less IFN-gamma (FIG. 82b). So here we show that IR treatment increases the production of anti-inflammatory cytokines (IL-10, TNF) while it decreases the production of inflammatory cytokine (IFN-gamma). This is consistent with our clinical observation that during 3 months of treatment no further progression was observed as measured by sinal inflammation activity. These results suggest a beneficial effect of IR-P.

PATIENT 2: Polymyoistis

Definition; A systemic connective tissue disease, which occurs through T cell mediated inflammation causing destruction of muscle fibers. Other possible causes of these syndromes include complement activation, infection, drugs, stress, vaccines. It can affect people at any age, but most commonly occurs in those between 50 to 70 years old, or in children between 5 to 15 years old. It affects women twice as often as men. Muscle weakness may appear suddenly or occur slowly over weeks or months. There may be difficulty with raising the arms over the head, rising from a sitting position, or climbing stairs. The voice may be affected by weakness of the larynx. Joint pain, inflammation of the heart, and pulmonary (lung) disease may occur. A similar condition, called dermatomyositis, is evident when a dusky, red rash appears over the face, neck, shoulders, upper chest, and back. A malignancy may be associated with this disorder. The incidence of polymyositis is 5 out of 10,000 people.

Patient 2: Diagnosis: Systemic sclerosis/Polymyositis overlap (based on histopathology).

Case; A 50 year old woman who suffered for two years from systemic sclerosis with an active polymyositis component. She was treated with Dapsone, steroids, methotrexate and cylosporine. Because of refractory myositis as measured by the creatin phosphate level she was treated for three months with a combination of prednisone, zyrtec and pregnyl 5000 I.U., s.c. During treatment the CPK level dropped from 1100 to 750. This reflects a decrease in disease activity.

Figure 86:
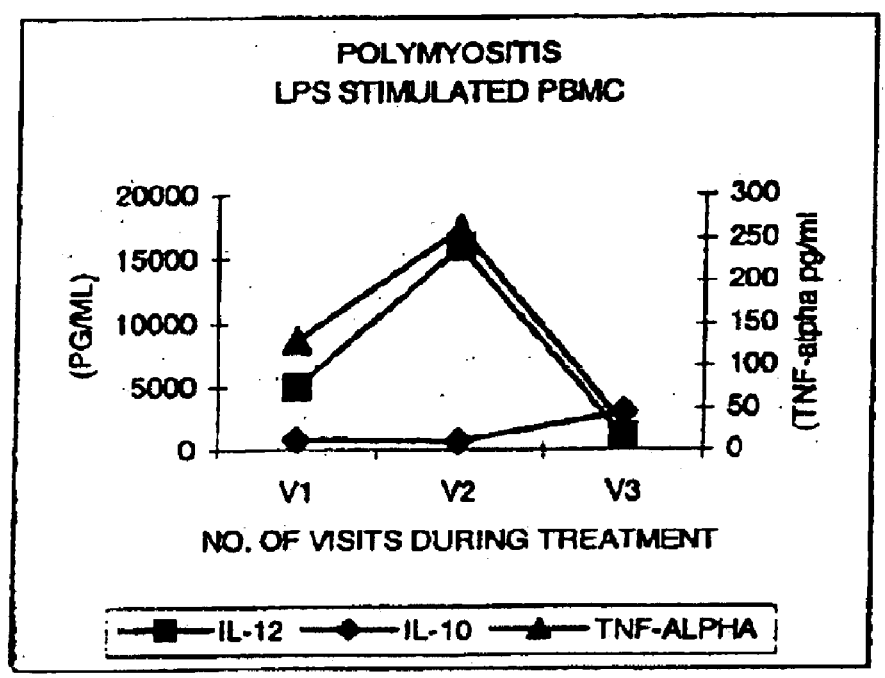

FIG. 83 shows that due to the IR-P treatment the number of lymphocytes, T cells (CD4, CD8) and B cells were decreased which indicates the down-regulation of the hyperactive immune system due to the treatment. This is also consistent with our cytokine data (FIG. 86) which shows inhibition of LPS stimulated IL-12 and TNF-alpha by PBMC. Moreover, there was an increase in IL-10 production during the treatment, which is an anti-inflammatory cytokine (FIG. 86). In addition, the elevated CPK and liver enzymes (ASAT, ALAT) were also decreased (FIGS. 84 and 85). This all reflects a decrease in the disease activity.

PATIENT 3: Diabetes Mellitus (Type I)

Diabetes mellitus is a chronic disorder characterized by impaired metabolism of glucose and other energy-yielding fuels, as well as the late development of vascular and neuropathic complications. Diabetes mellitus consists of a group of disorders involving distinct pathogenic mechanisms with hyperglycemia as the common denominator. Regardless of cause, the disease is associated with insulin deficiency, which may be total, partial, or relative when viewed in the context of coexisting insulin resistance. Lack of insulin plays a primary role in the metabolic derangements linked to diabetes, and hyperglycemia, in turn, plays a key role in the complications of the disease. In the United States diabetes mellitus is the fourth most common reason for patient contact with a physician and is a major cause of premature disability and mortality. It is the leading cause of blindness among working-age people, of end-stage renal disease, and of nontraumatic limb amputations. It increases the risk or cardiac, cerebral, and peripheral morbidity and mortality. On the bright side, recent data indicate that most of the debilitating complications of the disease can be prevented or delayed by prospective treatment of hyperglycemia and cardiovascular risk factors.

Insulin-dependent diabetes mellitus (IDDM) is one of the clinically defined types of diabetes and develops predominantly in children and young adults, but may appear in all age groups. The major genetic susceptibility to IDDM is linked to the HLA complex on chromosome 6. These genetic backgrounds interact with environmental factors (possibly certain viruses, foods and climate) to initiate the immune-mediated process that leads to beta cell destruction. While non-insulin dependent diabetes (NIDDM), which is another clinically defined type of diabetes, is the most common form of diabetes. The prevalence of NIDDM varies enormously from population to population. The greatest rates have been found in Pima Indians. The major environmental factors identified as contributing to this form of diabetes are obesity and reduced physical activity. NIDDM shows strong familial aggregation in all populations and is clearly the result of an interaction between genetic susceptibility and environmental factors. Before NIDDM develops, insulin concentrations are high for the degree of glycaemia and of obesity, reflecting the presence of insulin resistance. As insulin resistance worsens, glucose levels increase, with the appearance of glucose intolerance and, finally, of NIDDM, when insulin response cannot compensate for insulin resistance.

Since our preliminary mice data shows that IR has the ability to shift Th1 phenotype cytokines towards Th2 phenotype and IR is also able to inhibit diabetes in NOD mice, we postulated that it should also has positive clinical effects in human immune diseases like diabetes.

Patient 3: Diagnosis: Diabetes Mellitus Type I.

Figure 87:
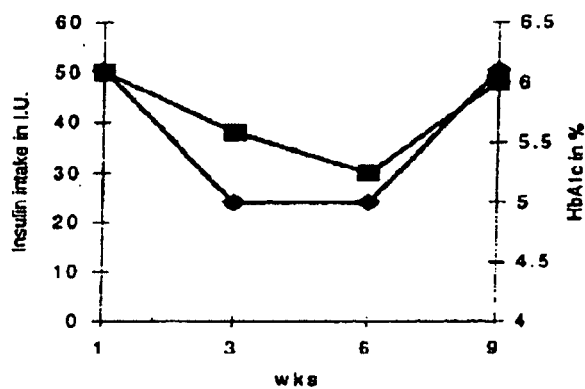
Figure 88:
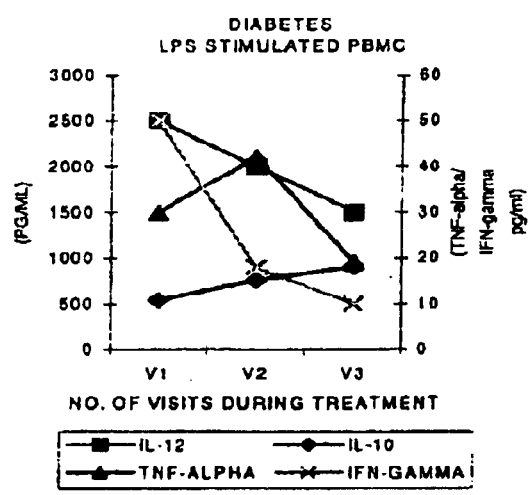

Case: Patient is a 21 year old male suffering from diabetes mellitus since 3 months. He was treated with insulin (actrapid and insulatard). High level of anti-island cell antibodies was in his blood. He was treated with pregnyl 5000 I.U. s.c. for three months. During his treatment the insulin need to maintain euglycaemia decreased as shown in FIG. 87. After withdrawal of pregnyl his insulin need raised again (FIG. 87). In this patient with newly onset of diabetes mellitus the insulin need dropped significantly during treatment with IR-P and also improvement of the glucose control was found, supported by a decrease in glycosylated HbAlc level during IR-P treatment (FIG. 87) and decrease in inflammatory cytokines (IL12, TNF-alpha, IFN-gamma) produced by LPS stimulated PBMC (FIG. 88). Furthermore, increase in TL-10 (anti-inflammatory cytokine) was also observed during the treatment (FIG. 88). This all suggests an improvement of the island cell function and eventually also better glucose regulation.

Multiple Sclerosis and Related Conditions (in Vitro Data)

Multiple Sclerosis (MS) is a disorder of unknown cause, defined clinically by characteristic symptoms, signs and progression, and pathololologically by scattered areas of inflammation and demyelination affecting the brain, optic nerves, and spinal cord. The first symptoms of MS most commonly occur between the ages of 15 and 50.

The cause of MS is unknown, but it is now widely believed that the pathogenesis involves immune-mediated inflammatory demyelination. Pathologic examination of MS brain shows the hallmarks of an immunopathologic process-perivascular infiltration by lymphocytes and monocytes, class II MHC antigen expression by cells in the lesions, lymphokines and monokines secreted by activated immune cells, and the absence of overt evidence for infection. Additional evidence for an autoimmune pathogenesis includes (1) immunologic abnormalities in blood and cerebrospinal fluid (CSF) of MS patients, notably selective intrathecal humoral immune activation, lymphocyte subset abnormalities, and a high frequency of activated lymphocytes in blood and CSF; (2) an association between MS and certain MHC class II allotypes, (3) the clinical response of MS patients to immunomodulation tends to improve with immunosuppressive drugs and worsens with interferon-gamma treatment, which stimulates the immune response; and (4) striking similarities between MS and experimental autoimmune encephalomyelitis (EAE)—an animal model in which recurrent episodes of inflammatory demyelination can be induced by inoculating susceptible animals with myelin basic protein or proteolipid protein.

Epidemiologic studies suggest environmental and genetic factors in the etiopathogenesis of MS. The uneven geographic distribution of the disease and the occurrence of several point-source epidemics have suggested environmental factors; however, intense study over the past 30 years has failed to establish an infectious cause. Migration studies have shown that exposure to undefined environmental factors prior to adolescence is required for subsequent development of MS. A genetic influence is well-established by excess concordance in monozygotic compared with dizygotic twins, clustering of MS in families, racial variablility in risk, and association with class II MHC allotypes. In Caucasians, the HLA class II haplotype DR15, DQ6, Dw2 appears strongly and consistently associated with an increased risk of MS.

The evidence—immunologic, epidemiologic, and genetic—supports the concept that exposure of genetically susceptible individuals to an environmental factor(s) during childhood (perhaps any on of many common viruses) may lead eventually to immune-mediated inflammatory demyelination. The precise interplay between genetic, environmental and immunologic factors and the nature of the environmental trigger(s) remains to be elucidated. We isolated PBMC from MS patients and stimulated these with LPS or PMA/Ca. After 24 hours of culture, supernatants were collected for cytokine analysis (TGF-beta, IL-10, IFN-gamma).

MS patient 1 (in vitro): there was an increase in production of TGF-beta and IL-10 in LPS stimulated PBMC treated with IR-P (FIGS. H and I). No differences were observed in TGF-beta and IL-10 production in cultures stimulated with PMA/Ca and treated with IR-P (FIGS. 89 and 90), while IR-P inhibited the production of IFN-gamma in PMA/Ca stimulated PBMC (FIG. 91).

Figure 92:
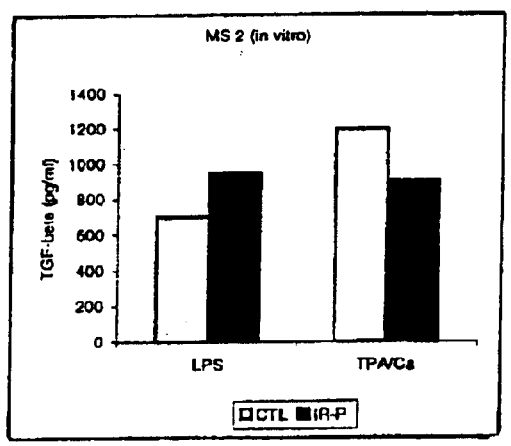
Figure 93:
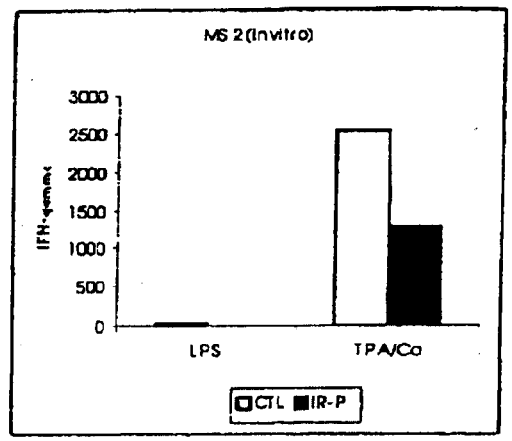
Figure 94:
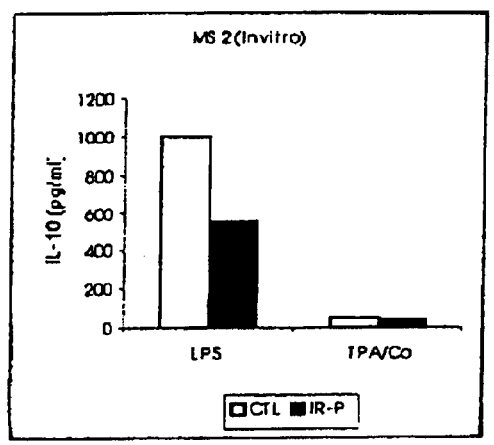

Ms patient 2 (in vitro): PBMC obtained from patient 2 showed a decreased production of TGF-beta and IFN-gamma in cultures treated with IR-P as compared to TPA/Ca stimulation alone, while IR-P treatment increased LPS stimulated TGF-beta production (FIGS. 92 and 93). IL-10 production was inhibited with IR-P in both LPS and TPA/Ca stimulated cultures (FIG. 94).

The stimulating effect of IR-P on the production of anti-inflammatory cytokines by PBMC from MS patients in vitro and the inhibitory effects on the production of inflammatory cytokines correlated with the benefical clinical effects of IR-P treatment of SJL mice in which EAE was induced (see elsewhere in this document).

Human Bronchial Epithelial Cell Line BEAS 2B (Asthma in Vitro Data):

Diseases characterized by airway inflammation affect a substantial proportion of the population. These diseases include asthma and chronic obstructive pulmonary disease (COPD). In the European Union, COPD and asthma, together with pneumonia, are the third most common cause of death. The production of cytokines and growth factors in response to irritants, infectious agents and inflammatory mediators play an important role in the initiation, perpetuation and inhibition of acute and chronic airway inflammation.

Airway inflammation is associated with excessive production and activity of several mediators and cytokines released by inflammatory and resident cells in the airways. Now it is clear that the epithelium is not only an important target for the action of mediators of inflammation, but also an active participant in the inflammatory process itself. Bronchial epithelial cells are able to recruit inflammatory cells to the airways through the release of chemoattractants, to direct inflammatory cell migration across the epithelium through the expression of cell adhesion molecules, and to regulate the inflammatory activity of other cells through the release of mediators, like cytokines, chemokines, arachidonic acid metabolities and relaxant and contractile factors.

Bronchial epithelial cells not only form a passive barrier but also play an active role in the immune respone. They are able to produce a variety of mediators that may act either pro- or anti-inflammatory. In addition, bronchial epithelial cells may express adhesion molecules for many different cell types, thereby contributing to their recruitment.

TNF-alpha produced by inflammatory cells present in the air ways can trigger other inflammatory cytokines and chemokines like RANTES and IL-6. It can also down-regulate the production of anti-inflammatory cytokines and thereby damage the barrier function of epithial cells.

Glucocorticoids inhibit the transcription of most cytokines and chemokines that are relavant in asthma, including IL-6, RANTES, IL-4. This inhibition is at least partially responsible for the therapeutic effects of glucocorticoids.

Figure 71:
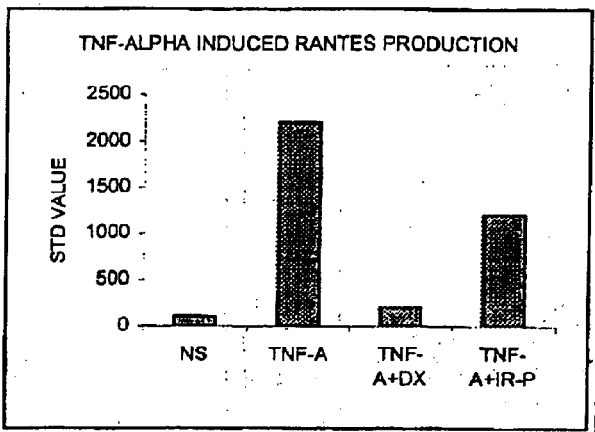
Figure 72:
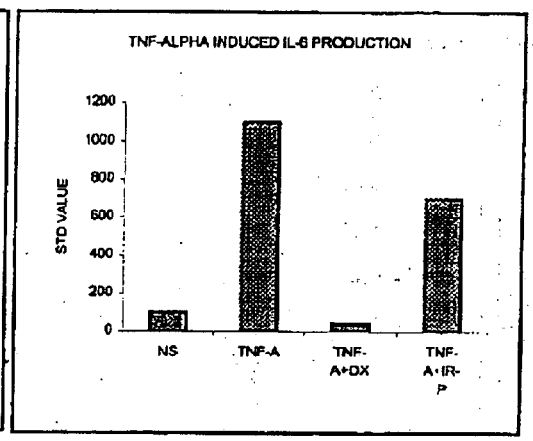
Figure 73:
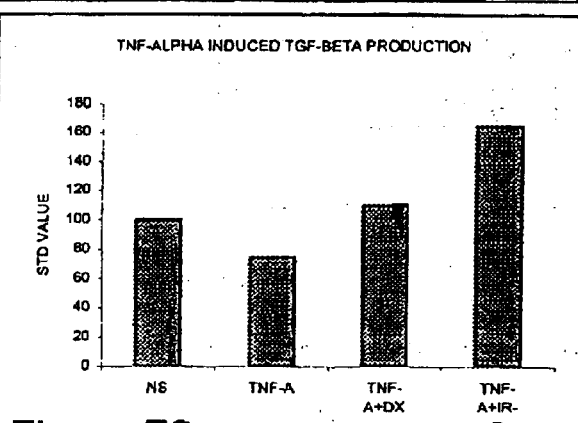
Figure 74:
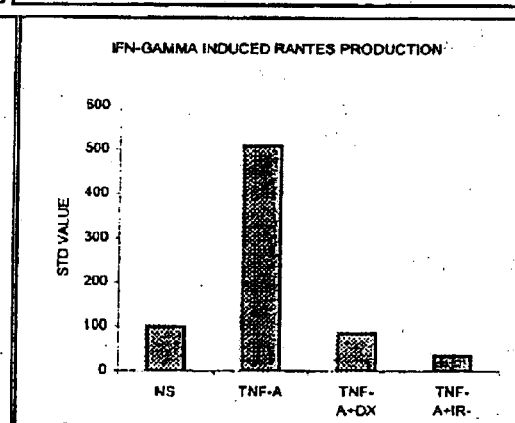

Our results (FIGS. 71–73) are consistent with these findings, and show that Dexamethasone is able to inhbit TNF-alpha induced IL-6 and RANTES production in the BEAS 2B cell line. IR-P is also able to inhibit the production of TNF-alpha induced inflammatory cytokines. Moreover, dexamethasone was able to restore TNF-alpha induced down-regulation of anti-inflammatory TGF-beta cytokine, while IR-P not only restores TGF-beta production but also promotes this anti-inflammatory cytokine further (FIG. 73). In addition, Dexamethasone and IR-P were both able to inhibit IFN-gamma induced production of RANTES (FIG. 74).

Figure 75:
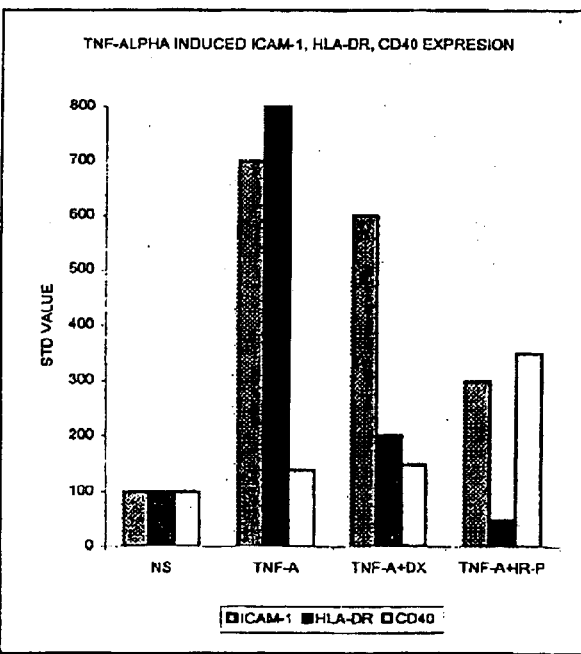
Figure 76:
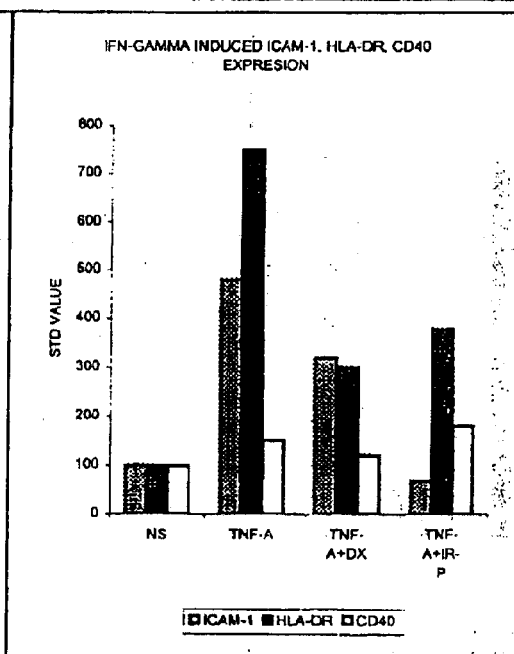

TNF-alpha can also induce cell adhesion markers, such as HLA-DR and ICAM-1 on the surface of epithial cells which then recruit inflammatory cells. In this way epithial cells can also function as antigen presenting cells (APC). Our results show that Dexamthesone and IR-P both were able to down-regulate the TNF-alpha induced expression of HLA-DR and ICAM-1 (FIGS. 75 and 76).

These results show that IR-P has also the ability to affect the clinical course of diseases characterised by Th2-type cytokine phenotype like allergy, asthma and particular parasitic diseases.

Discussion

Nonobese diabetic (NOD) mice naturally develop an insulin-dependent diabetes (IDDM) with remarkable similarity in immunopathology and clinical symptoms to human IDDM patients. As a result, NOD mice have become a valuable tool for studying the underlying immunobiology of IDDM and the complex genetics that control it. Through their study we now know that diabetes is caused by a disbalance in the ratio of the Th1/Th2 subsets and consequently, the destruction of insulin producing β-cells. This destruction is co-ordinated by β-cell antigen-specific CD4+ T cells that produce proinflammatory cytokines like IFN-γ, TNF-á/γ and IL-1. A growing number of studies has now correlated diabetes (in mice and in humans) with a preferential development of Th1-like cells.

In contrast, pregnancy is thought to be a selective Th2 phenomenon, and surprisingly during pregnancy the severity of many immune-mediated diseases has been seen reducing. In contrast, Gallo et al. have shown that hCG mediated factor(s) (HAF) present in the urine of first trimester pregnancy have an anti-tumour (and anti-viral) effect, which is possibly achieved by a direct cytotoxic effect on tumour cells and, according to these authors, not by an immune-mediated response.

Here we show an immunoregulator obtainable for example from urine of (first trimester) pregnancy not only effects the above mentioned immune deviation during pregnancy, but also effects the development of diabetes in NOD mice.

Our result show that for example Pregnyl, a partially purified hCG preparation from urine of first trimester pregnancy, can delay the onset of diabetes, for example in 15-wk-old NOD when treated only for 3 times a week during four weeks. In addition, spleen cells isolated from these treated mice upon transfer have also the potential to delay the onset of diabetes in immuno-compromised NOD.scid mice. We fractionated a Pregnyl preparation to assess whether this anti-diabetic activity resides in hCG itself, its subunits, β-core (naturally break-down product of β-hCG) or in unidentified factors (HAF). It is worth knowing that Pregnyl is one of the most purified hCG preparations available and it contains only low amounts of β-core fragments. We found that most of the anti-diabetic activity resided in a fraction without hCG. Furthermore, we showed that human recombinant á-hCG and β-HCG also had no effect. However, we do not exclude the possibility that hCG can synergize with other factors in diabetes and other immune mediated diseases.

Immunohistological analysis of the presence of insulin and infiltration in the pancreas of NOD mice showed that NOD mice treated with 600 IU Pregnyl did not reveal a significant infiltrate. Moreover, new insulin islets were seen the in pancreas, which shows a possible regeneration process induced by this treatment. As mentioned before, normally at the age of 9 weeks infiltrating cells penetrate into the islets and the islets become swollen with lymphocytes. In our experiments, the NOD mice were 15-wk-old and the PBS treated control mice had many infiltrating cells and almost no insulin producing cells at that time in their pancreas. In addition, PBS treated mice had also an elevated ratio of CD8/CD4 in their spleen and many T cells in their pancreas. Since our treated mice had a normal CDB/CD4 ratio in their spleen and no infiltration was found in their pancreas, the elevated CD8/CD4 ratio was due to selective recruitment of CD4+ cells into the pancreas. IN-γ and TNF-á are involved in the recruitment of T lymphocytes (Rosenberg et al. 1998).

Our results show that treatment of NOD mice with 600 IU Pregnyl for four weeks had dramatic effects on the morphology and function of their otherwise inflamed pancreas. Furthermore, our 300 IU Pregnyl NOD mice were kept alive till the age of 28 weeks without treatment and remained non-diabetic. The 600 IU Pregnyl NOD mice were also examined for symptoms of generalised auto-immune diseases, like Sjögren's disease, which were not found.

Our in vitro experiments with total spleen cells and purified CD4+ cells of NOD are consistent with the in vivo data. There was marked inhibition of IFN-γ, IL-1 and TNF-á release by spleen cells (data not shown) from NOD mice treated in vitro with Pregnyl, F3-5, and to lesser extent with human recombinant β-hCG. Increase in IL-4 production was also observed implying a shift of Th1 co Th2 type response with the treatment. However, doses above 800 IU Pregnyl caused opposite results and may be due to the presence of high amount of hCG itself.

The immune system is clearly involved in the onset of diabetes. Treatment with Pregnyl effects the immune system and thereby can reduce the disease activity in NOD mice. In order to separate the immune-modulating activity of Pregnyl from its benefical clinical effect, we treated healthy BALB/c mice. This strain is generally considered to react upon stimulation with a Th2 driven immune response. Our results suggest that purified CD4+ T cells obtained from Pregnyl-treated BALB/c mice display a further Th2 skewing. The same cells when restimulated with Pregnyl in vitro showed an enhancement of IFN-γ production and a decrease in IL-4 production. This implies that Pregnyl effects different regulatory T cells subsets upon treatment in vivo versus in vitro. We suggest that treatment in vivo stimulates the outgrowth of a population of presumably CD4+ Tr1 cells, characterised by selective production of TGF-β and a lower or no production of IL-10. These CD4+Tr1 cells have been shown (O'Garra et al. 1997) in different models of Th1 driven diseases including diabetes and MS, to selectively inhibit the activity of Th1 cells, thereby decreasing the disease severity also. Similar by CD4+ T cells from Pregnyl treated BALB/c mice restimulated in vitro with Pregnyl showed an increase of Th1 cells concomitant with a decrease of Th2 cells. This is consistent with a preferential stimulation of the CD4+ Th3 cells characterized by a high production of IL-10 and a low production of TGF-β. These regulatory cells are inhibitors of IFN-γ production by Th1 cells as well as the outgrowth of Th2 type cells. It has been also shown that in NOD.scid mice a steady increase of Th2 cells is responsible for the less severe hyperglycemia and the different nature of the infiltrates in the pancreatic islets.

Our results of the 300 IU Pregnyl treated NOD and our reconsituted NOD.scid mice showed a similar slow increase in blood glucose, particularly in NOD.scid, and a different nature of the infiltrates as compared to PBS-treated NOD. In NOD mice the activity of Pregnyl might well be mediated with the induction of Th3 cells inhibiting both Th1 and Th2 cells. These Th3 cells may suppress the disease activity for prolonged periods of time at the very least. In NOD.scid mice, having no functional T cells, reconstitution with Pregnyl-treated spleen cells is mediated with selective induction of Tr1 cells and thereby inhibiting the Th1 subset only. After prolonged periods the steady outgrowth of diabetogenic Th2 cells is responsible for the late onset of a less severe form of diabetes. Similarly our F3-5, but not F1-2, displays the above discussed phenomenon, arguing that hCG can not be responsible for the observed effects. This F3-5 is principally pointing towards a decisive effect on the immune response in the onset of auto-immune diabetes and is an active component for immunotherapy of this disease and other immune mediated disorders.

In addition, Pregnyl and immunoregulators functionally equivalent thereto, is effective in Non-insulin-diabetes mellitus (NIDDM). The essential problem in NIDDM patients is the insulin resistancy and obesity, it has been shown that TNF-(alpha) is the cause of the insulin resistance of obesity and NIDDM (Miles et al. 1997, Solomon et al. 1997, Pfeiffer et al. 1997, Hotamisligil et al. 1994), Argiles et al. 1994). This insulin resistance induced by TNF-alpha can be reversed by recently developed medicines like Pioglitazone and Metformin, and with engineered human anti-TNF-alpha antibody (CDP571) (Solomon et al. 1997, Ofei et al. 1996), which possibly achieved their benefical action by lowering TNF-alpha induced free fatty acids (FFA) concentration of the blood and/or by stimulating glucose uptake at an intracellular point distal to insulin receptor autophosphorylation in muscle. Furthermore, the presence of retinopathy (Pfeiffer et al. 1997) (one of the late complications of diabetes) has been mediated with significantly elevated plasma TNF-alpha and is sex-dependent (Pfeiffer et al. 1997). The increased TNF-alpha occurs in male but not in female NIDDM and may participate in the development of retinopathy and other complications like neuropathy, nephropathy or macroangiopathy (Pfeiffer et al. 1997). Since Pregnyl and fraction 3–5 have immune modulating potential and in particular inhibit TNF-alpha directly or indirectly, Pregnyl and its fraction 3–5 have also benefical effects in NIDDM patients. Besides, lower incidence of diabetes complications among female could implicate the involvement of female hormones. A key pathogenic cytokine indicated in sepsis or septic shock is the immunological mediator TNFα which occupies a key role in the patho-physiology associated with diverse inflammatory states and other serious illnesses including sepsis or septic shock and cachexia. When TNF is produced by T cells (for example by T cell activation through superantigen [exotoxin]) or by macrophages through endotoxin), it mediates an inflammatory response that may alienate and repel the attacking organisms. When the infection spreads, the subsequent release of large quantities of TNF into the circulation is catastrophic, damaging the organ system and triggering a state of lethal shock. These toxic effect occur by direct action of TNF on host cells and by the interaction with cascade of other endogenous immunological mediators including IL-1, IFN-gamma.

This has been shown by induction of shock like symptoms in mice sensitised with D-Calactosamine and treated with TNFα as well as inhibition of both lethality and visible signs of disease after concurrent infusion of anti-TNFα Abs following TSST-1 and D-Galactosamine treatment. In the low dose endotoxin model and in exotoxin model, D-Galactosamine treatment is necessary to inhibit the transcription of acute phase proteins that allow the liver to detoxify the high levels of TNFα present following shock induction. The lack of these acute phase proteins leads to increased susceptibility of murine hepatocytes to TNFαmediated apoptosis induction. This apoptosis, and inability to neutralise the inflammatory effects of TNFα eventually lead to death. We have shown that factors (IR) with or without hCG present in for example the urine of first trimester of pregnancy (IR-U) and in commercial hCG preparations (IR-P) have immune regulatory effects. In particular, they have the potential to inhibit auto-immune and inflammatory diseases. Since TNF and IFN-gamma are pathologically involved in sepsis or septic shock and also in auto-immune and inflammatory diseases, IR has also the ability to inhibit TNF and IFN-gamma in acute inflammatory states like shock. Our results show that IR inhibits sepsis or septic shock in BALB/c or SJL, treated with LPS (endotoxin model) or with TSST-1 (exotoxin model). IR has not only the potency to inhibit chronic inflammatory diseases but it can also suppress acute inflammatory diseases like shock. Moreover, we also show that even post-treatment with IR inhibits the shock. Furthermore, our IR fraction data show that most of the anti-shock activity resides in fractions IR-(U/P)3–5[pooled] which contain mostly individual chains of hCG, homodimers of these chains or beta-core residual chains, breakdown products of these chains and other molecules (>30 kDa). We have also shown that the same fractions IR-U/P3-5 have anti-diabetic effect in NOD mice model. Thus the endotoxin and exotoxin model serves as a fast readout model for the determination of anti-diabetic activity in NOD mice and NOD.scid mice. With the help of endotoxin and exotoxin model we can check for anti-diabetic activity in IR fractions within 48 hours.

Thus, IR such as Pregnyl and its fraction 3–5 have high potency to suppress auto-immune diabetes by modulating the immune system by effecting regulatory T cells subsets. Our NOD and BALB/c data show that they have the potential to restore the T-cell subset balance (Th1->Th2/Th2->Th1). Therefore, Pregnyl and its fraction 3-5 are effective in modulating the severity of other immune-mediated diseases too, like diseases where Th1 cytokines are dominant such as Rheumatoid Arthritis (RA), Multiple Sclerosis (MS), NIDDM, Systemic lupus erythematosus (SLE), transplantation models and diseases like allergies and asthma where Th2 cytokines responses are dominant. Animal models of these diseases (like EAE-model for MS, BB-rats for NIDDM, Fishe-rat and MLR-models for RA, OVA-model for allergies, MLR/1pr and BXSB-models for SLE), KK-Ay-mice, GK rats, wistar fatty rate, and fa/fa rats provide, amongst others, models of other immune-mediated diseases.

FIGURE LEGENDS

FIG. 1. Shows that 15-weeks-old NOD mice treated with PBS for 4 weeks, become diabetic (>13.75 mmol/l) at the age of 17 weeks and within a week they had blood glucose levels above 30 mmol/l, while NOD mice treated with 300 Pregnyl remained nondiabetic till they were killed (at the age of 28-weeks) even the treatment was stopped at age 19 weeks. There blood glucose level remained lower than 8 mmol/l.

Figure 2:
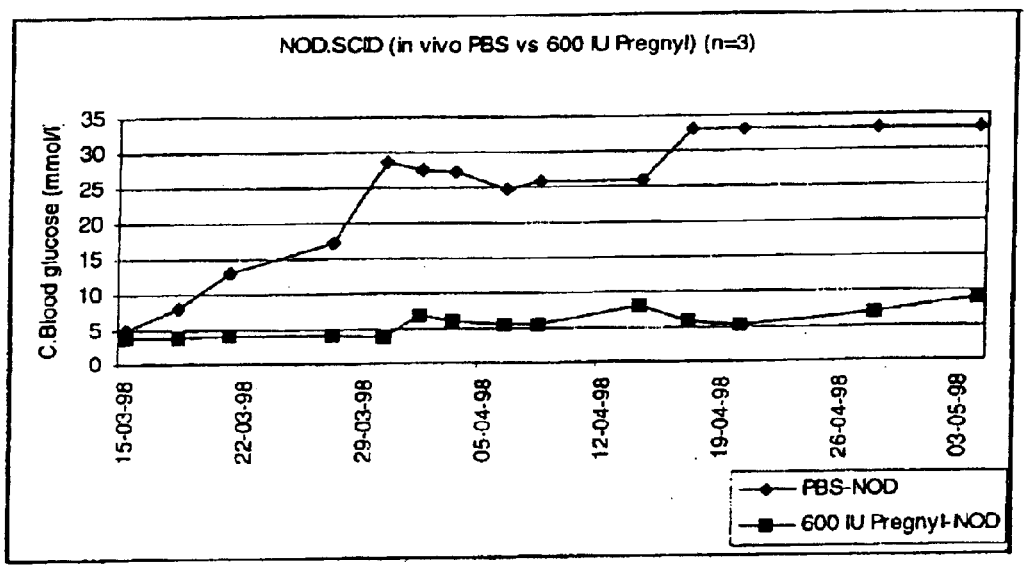

FIG. 2. shows that reconsituted NOD.scid mice receiving spleen cells from PBS treated NOD mice (FIG. 3) became diabetic after 22 days of transferring, while reconsituted NOD.scid mice with 600 IU Pregnyl treated NOD remained nondiabetic till they were killed (8 weeks after transferring).

FIG. 3. Shows that 15-weeks-old NOD mice treated with PBS for 4 weeks, become diabetic (>13.75 mmol/l) at the age of 17 weeks and within a week they had blood glucose levels above 30 mmol/l, while NOD mice treated with 600 IU Pregnyl remained nondiabetic till they were killed along with PBS group (at the age of 21-weeks). 15-weeks-old NOD mice treated with 300 IU Pregnyl remained nondiabetic till they were killed (at the age of 28-weeks) even the treatment was stopped at age 19 weeks. There blood glucose levels remained lower than 8 mmol/l.

FIG. 4. Spleens cells from 20-weeks-old female NOD were islolated and were cultured for 48 hrs with different conditions ('–' only medium, '+' with anti-CD3, 50, 100, 300, 600, 800 IU/ml Pregnyl, F1-2, F3-5, rh-hCG, rh-alpha-hCG, rh-beta-hCG [each at 200 ug/ml]) in the presence of anti-CD3 and IL-2. After 48 hrs INF-(cytokine ELISA were done. Results shows that there is dose dependent inhibition of INF-(with Pregnyl (50–600 IU/ml) and fraction 3-5 (F3-5) containing no hCG. There is an increase in INF-g with 800 IU/ml Pregnyl which suggests the effect of hCG itself. NO effect on INF-g were seen with fraction 1-2 (F1-2) containing hCG, human recombinant (rh) hCG, rh-alpha-hCG. Slight decrease in INF-g level is seen with rh-beta-hCG.

FIG. 5. Spleens cells from 20-weeks-old female NOD were isolated and were cultured for 46 hrs with different conditions ('–' only medium, '+' with anti-CD3, 50, 100, 300, 600, 800 IU/ml Pregnyl, F1-2, F3-5, rh-hCG, rh-alpha-hCG, rh-beta-hCG (each at 200 μg/ml)] in the presence of anti-CD3 and IL-2. After 46 hrs IL-4 cytokine ELISA was done. Results shows that there is a dose dependent increase of IL-4 with Pregnyl (50-600 IU/ml) and fraction 3-5 (F3-5) containing no hCG. There is an decrease in IL-4 with 800 IU/ml Pregnyl which suggests the effect of hCG itself. NO effect on IL-4 were seen with fraction 1-2 (F1-2) containing hCG, human recombinant (rh) hCG, rh-alpha-hCG and rh-beta-hCG.

FIG. 6. CD4 T-cells from spleen of 20-weeks-old female NOD were isolated and were cultured for 48 hrs with different conditions ('−' only medium, '+' with anti-CD3, 50, 100, 300, 600, 800 IU/ml Pregnyl, F1-2, F3-5, rh-hCG, rh-alpha-hCG, rh-beta-hCG [each at 200 μg/ml]) in the presence of anti-CD3, IL-2 and anti-CD28. After 48 hrs INF-γ cytokine ELISA were done. Results shows that there is dose dependent inhibition of INF-γ with Pregnyl (50-300 IU/ml) and fraction 3-5 (F3-5) containing no hCG. There is an increase in INF-γ with 600-800 IU/ml Pregnyl which suggests the effect of hCG itself. NO effect on INF-g were seen with fraction 1-2 (F1-2) containing hCG, human recombinant (rh) hCG, rh-alpha-hCG. Slightly decrease in INF-γ level is seen with rh-beta-hCG.

FIG. 7. Show the transfer experiment of 20-weeks old female spleen cells treated with PBS, 600 IU Pregnyl, fraction 1-2(F1-2), Fraction 3-5(F3-5) or human recombinant beta-hCG (b-hCG) for 48 hrs and then transferred into 8-weeks old NOD.scid (n=3). After 22 days of transfer the NOD.scid mice receiving PBS treated NOD spleens were diabetic. NOD.scid mice receiving F1-2 and b-hCG were diabetic after 4 and 5 weeks respectively while NOD.scid mice receiving 600 IU Pregnyl and F3-5 remained nondiabetic about 6 weeks and then all mice were killed. It shows that the maximum antidiabetic effect resides in Pregnyl and F3-5. Since F1-2 which contain mostly hCG have no effect on the incidence of diabetes in these mice, it is clear that antidiabetic effect does not reside in hCG itself. There is slightly anti-diabetic affect in recombinant human beta-hCG.

FIGS. 8–11

Figure 8:
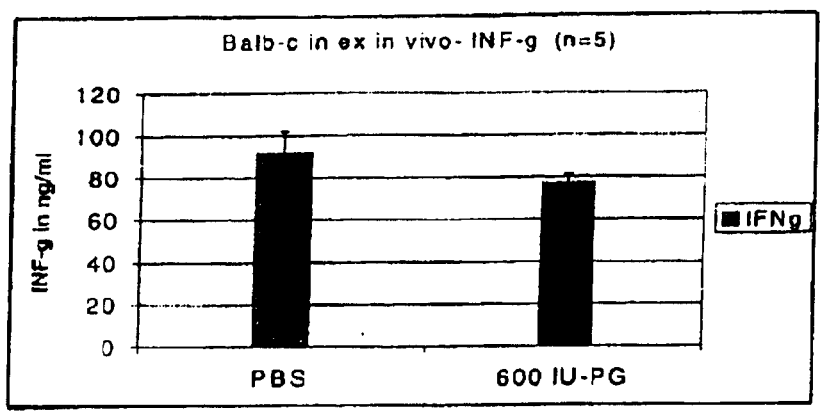
Figure 9:
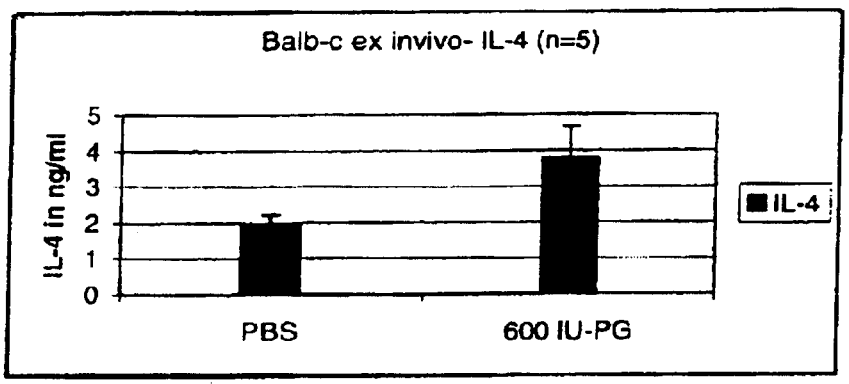
Figure 10:
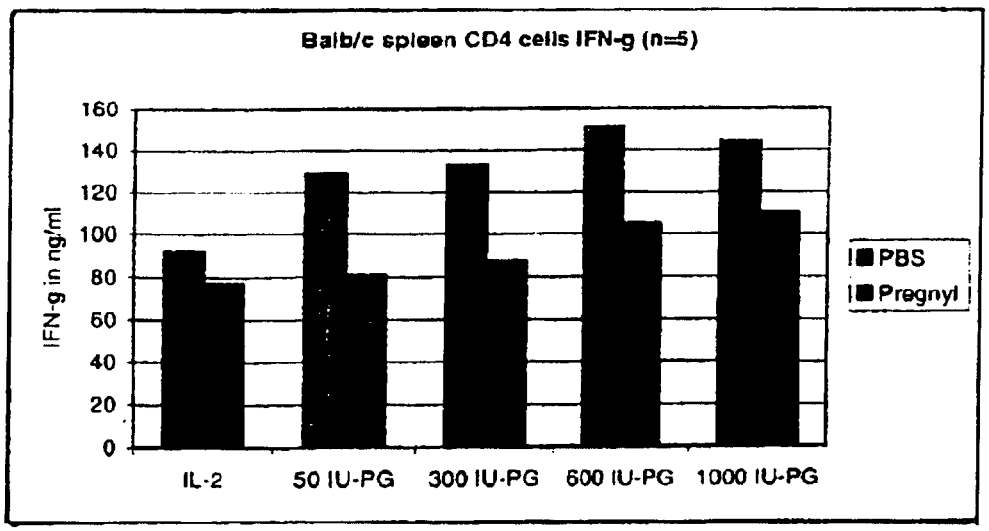
Figure 11:
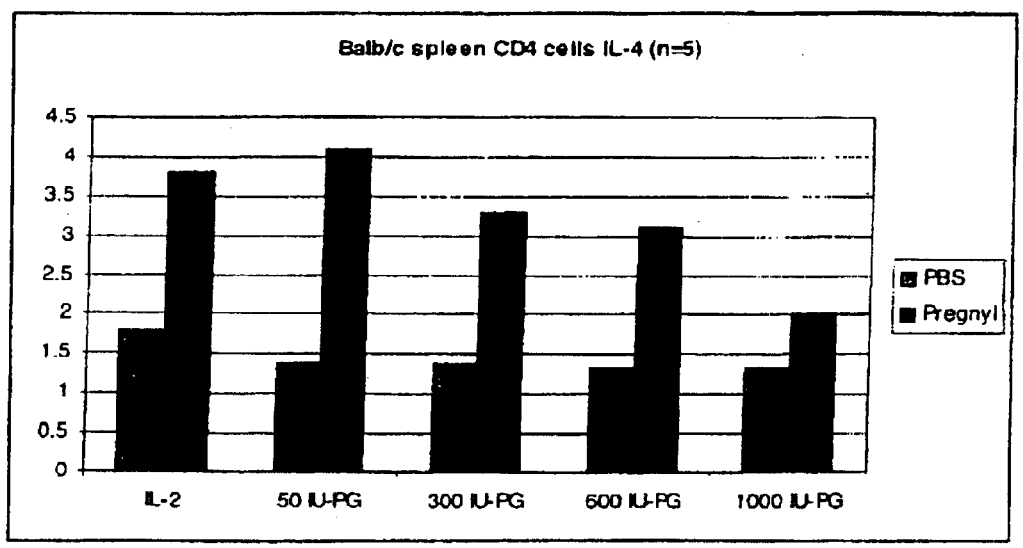

In order to test whether Pregnyl has also effect on Th2 type mice, we treated BALB/c mice (n=5) with 300 IU Pregnyl i.p. for four days and with PBS (n=5). After isolating CD4$^+$ cells from spleens we stimulated them with anti-CD3/IL-2 for 48 hours and the supernatants were collected for the determination of IFN-γ (FIG. 8) and IL-4 (FIG. 9) cytokines. We also treated CD4$^+$ cells with different doses of Pregnyl. Subsequently the supernatants were collected for INF-g ELISA (FIG. 10) analyses. FIG. 8 shows the invivo treatment with 300 IU Pregnyl suppress INF-g and on the other hand increases IL-4 production. This implies that there is more shift towards Th-2 phenotype. Same cells treated again in vitro with different dosis of Pregnyl show (FIG. 10) increase in INF-g and decrease in IL-4 (FIG. 11) which suggest the shift towards Th-1 phenotype. This all implies that Pregnyl and F3-5 have affect on regulatory T-cell subset (Th3, Tr1).

FIG. 12

Column

Superdex 75 HR 10/30; FPLC system (Pharamcia) total volume V$_t$=25 ml; void volume V$_0$=8.7 ml; flow rate: 1 ml/min; buffer: 10 mM
phosphate-buffered saline, pH 7.3; at room temperature column efficiency=38,000 N/m
selectivity K$_{AV}$=1.737−0.2782 log (r$^2$=0.982), MW=molecular mass
separation range: 3,000-100,000 Dalton for globular proteins

| running method METHOD NO. 4 | | |
|---|---|---|
| 0.0 | CONC % B | 0.0 |
| 0.0 | ML/MIN | 0.20 |
| 0.0 | CM/ML | 0.20 |
| 0.5 | ML/MIN | 0.50 |
| 0.5 | CM/ML | 0.50 |

-continued

| running method METHOD NO. 4 | | |
|---|---|---|
| 0.8 | ML/MIN | 1.00 |
| 2.0 | CLEAR DATA | |
| 2.0 | ALARM | 0.1 |
| 2.0 | HOLD | |
| 2.0 | VALVE.POS | 1.2 |
| 2.0 | MONITOR | 1 |
| 2.0 | LEVEL % | 5.0 |
| 2.0 | ML/MARK | 2.0 |
| 2.0 | INTEGRATE | 1 |
| 4.0 | VALVE.POS | 1.1 |
| 6.0 | PORT.SET | 6.0 |
| 30.0 | INTEGRATE | 0 |
| 45.0 | CONC % B | 0.0 |

Sample
Pregnyl (Organon, lot nr.;168558, exp.date:28, Nov. 1999) sample volume=0.5 ml ~2,000 units; sensitivity 0.1 AUFS
Chromatogram
Peak 1=fractions 1-2: Ve 14.7–15.1 ml;K$_{AV}$=0.37–0.39
Peak 2=fractions 3-5: Ve 15.38–17.99 ml;
K$_{AV}$=0.41–0.57
K$_{AV}$=(V$_e$−V$_0$)/(V$_t$−V$_0$)

Peak 1 elutes at a volume between 14.7–15.1 ml after start of the separation. This corresponds to a molecular mass between 70,000-80,000 Dalton. This fraction contains in part the dimeric form of hCG (Textbook of Endocrine Physiology, Second edition, J. E. Griffin, S.R. Ojeda (Ed.) Oxford University Press, Oxford, 1992, pp. 199). Peak 2 elutes at a volume between 15.38 and 17.99 ml, corresponding to a volume between 1500-58,000 Dalton. This fraction contains partly β-subunit (MW=22,200 Dalton), breakdown products of hCG and other, as yet, unknown molecules. These calculations were based on the above-mentioned selectivity of this column.

Figure 13:
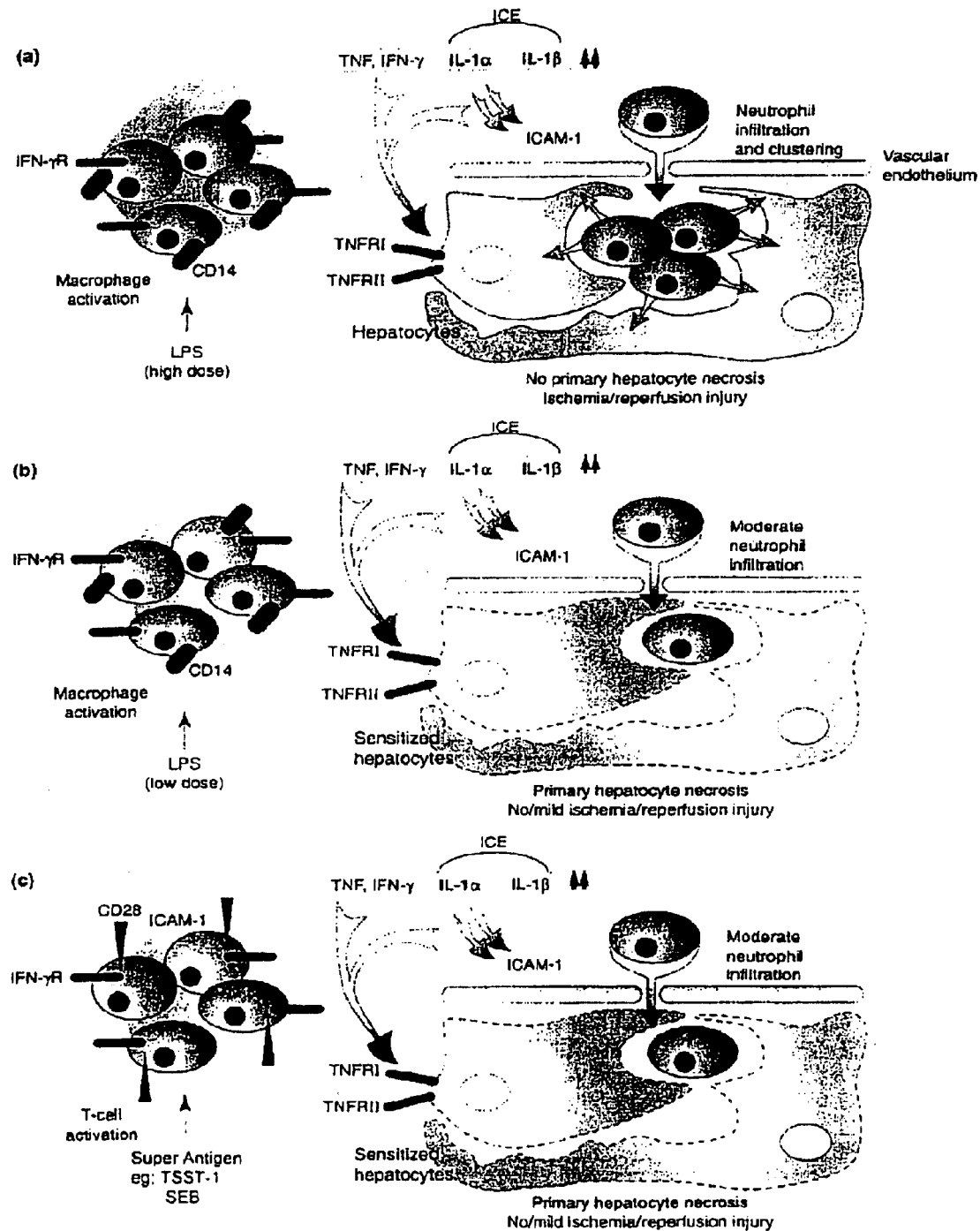

FIG. 13. Prosposed mechanisms operating in three different models of sepsis or septic shock. A) is a high-dose endotoxin model. B) is a low-dose endotoxin model. C) is exotoxin model for TSST-1/SEB. In high and low-dose endotoxin model (a,b) the systemic effects of endotoxin (LPS) is largely mediated by macrophages while in exotoxin model (c) the systemic effects of supper antigen (TSST-1/SEB) is mediated by T-cells. In both cases production of TNF, IFN and ICE (IL-1 alpha and beta) play important role in the pathogenesis of septic shock.

FIG. 14. T-cell activation induced by super-antigens like TSST-1 can be seen as a polyclonal T-cell activation in that T-cells expressing a specific V-beta family are all activated through non antigen specific binding of the TCR/MHCII/ and superantigen.

FIG. 15. An FPLC chromatogram of 50 μl of undiluted IR-U sample.

Figure 16:
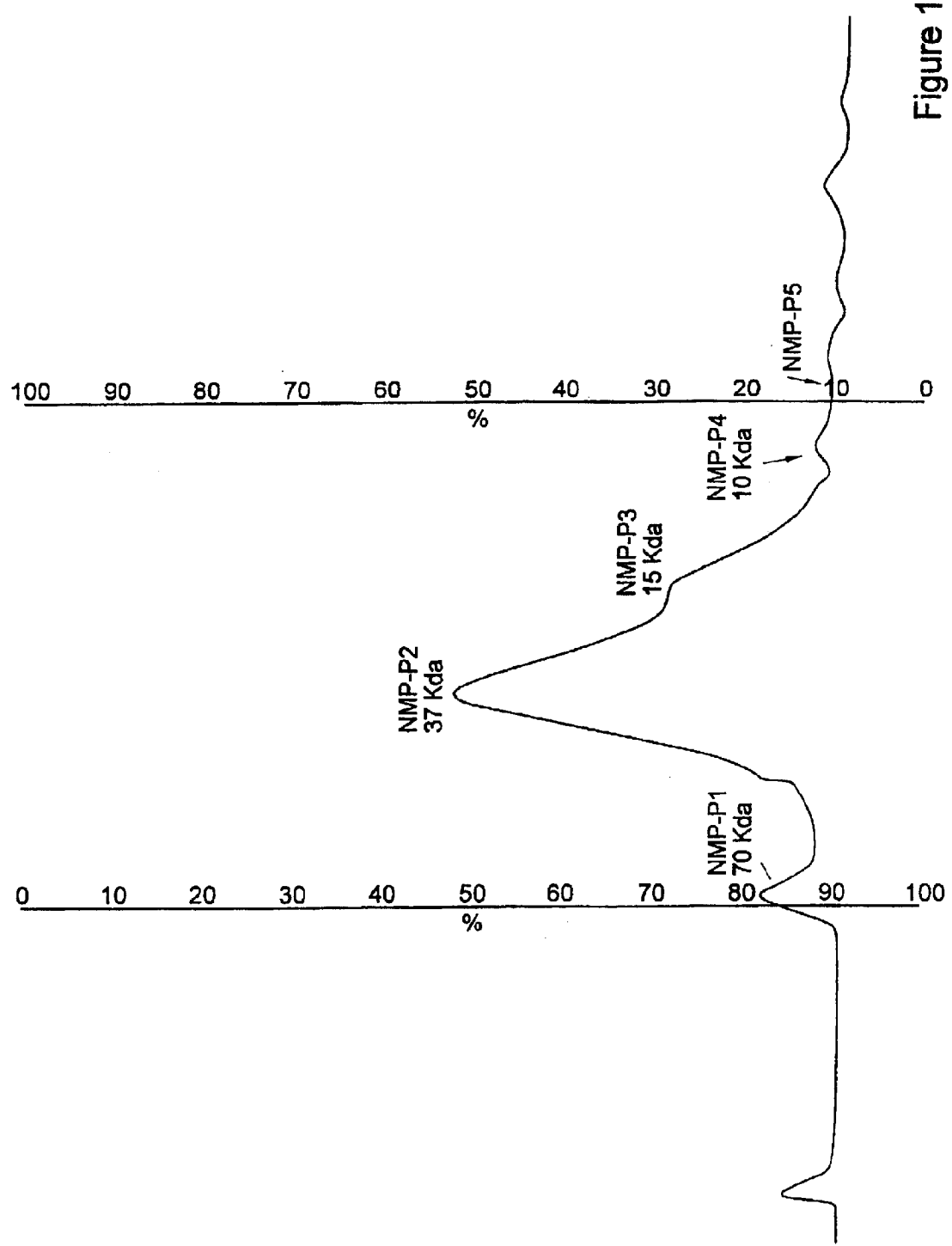

FIG. 16. An FPLC chromatogram of 500 μl of undiluted IR-P sample.

FIG. 17. Further separation of fractions 2 and 3 from FIG. 15.

FIG. 18. An FPLC chromatogram of 50 μl 2-mercapto ethanol treated IR-U sample.

Figure 19:
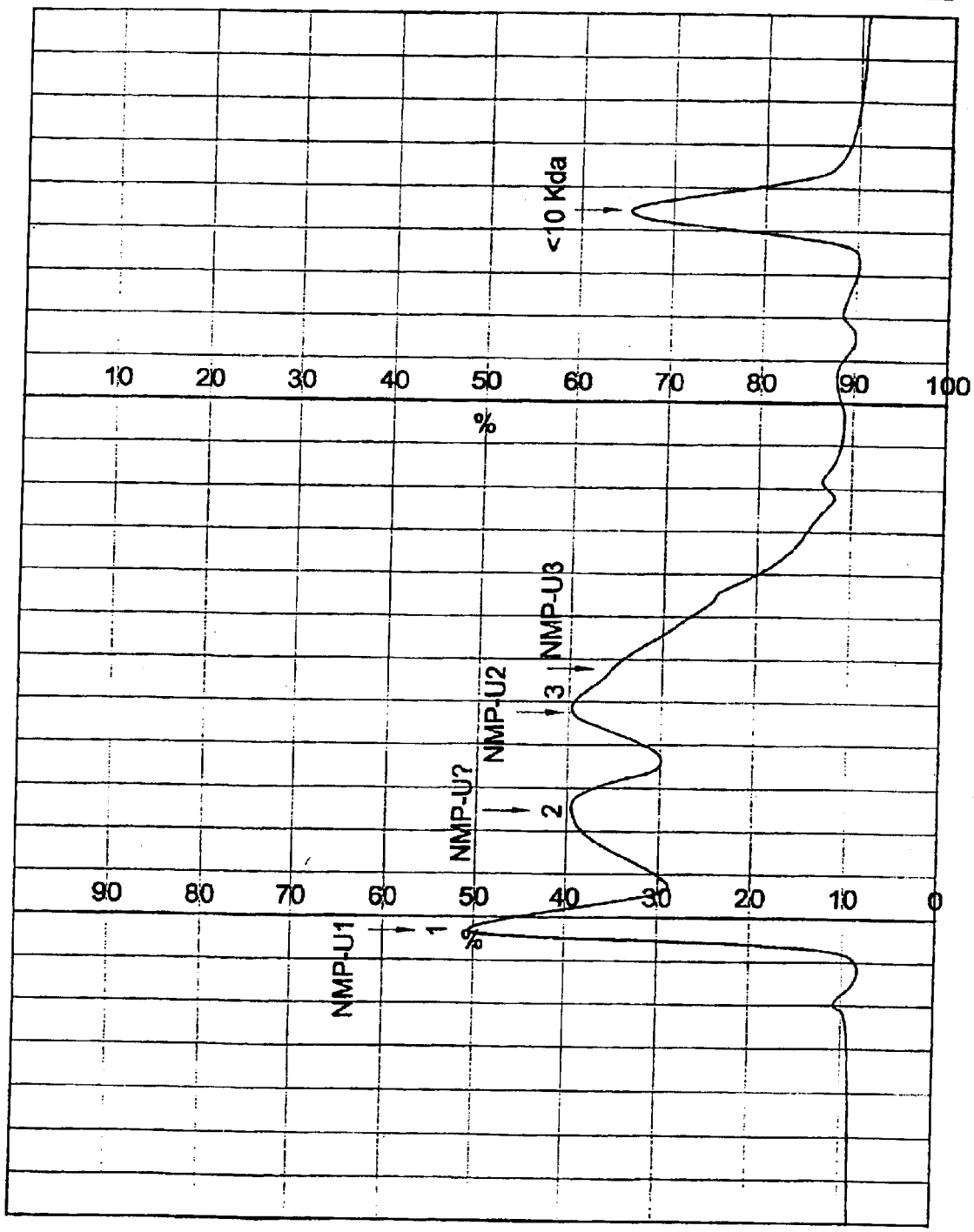

FIG. 19. An HPLC chromatogram of 500 μl 2-mercapto ethanol treated IR-P sample.

FIG. 20. A black and white difference in survival between those animals treated with IR-P prior to TSST-1 and D-Gal treatment versus those that were not is found.

Figure 21:
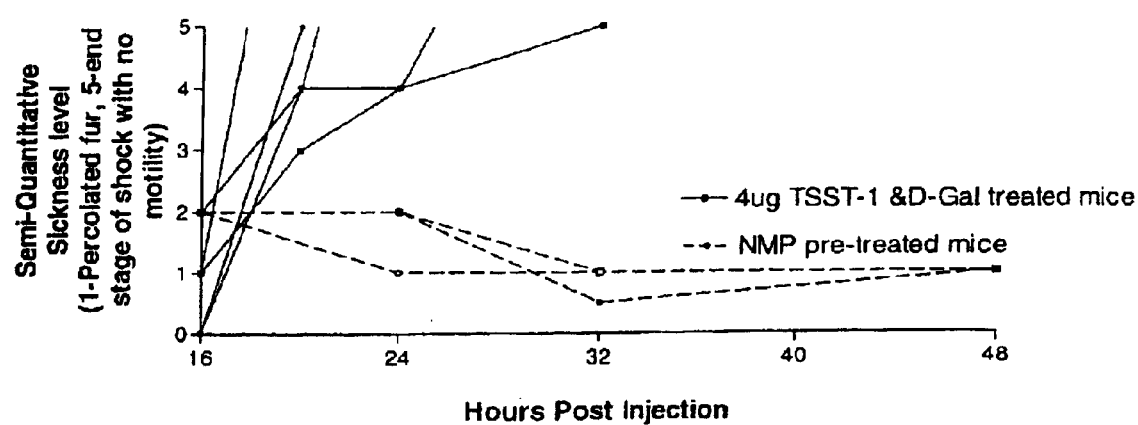

FIG. 21. IR-P pretreated Balb/c mice group did not exceed the sickness level 2 in TSST-1 exotoxin model while D-Gal-TSST-1 group exceed the sickness level 5 and were killed.

Figure 22:
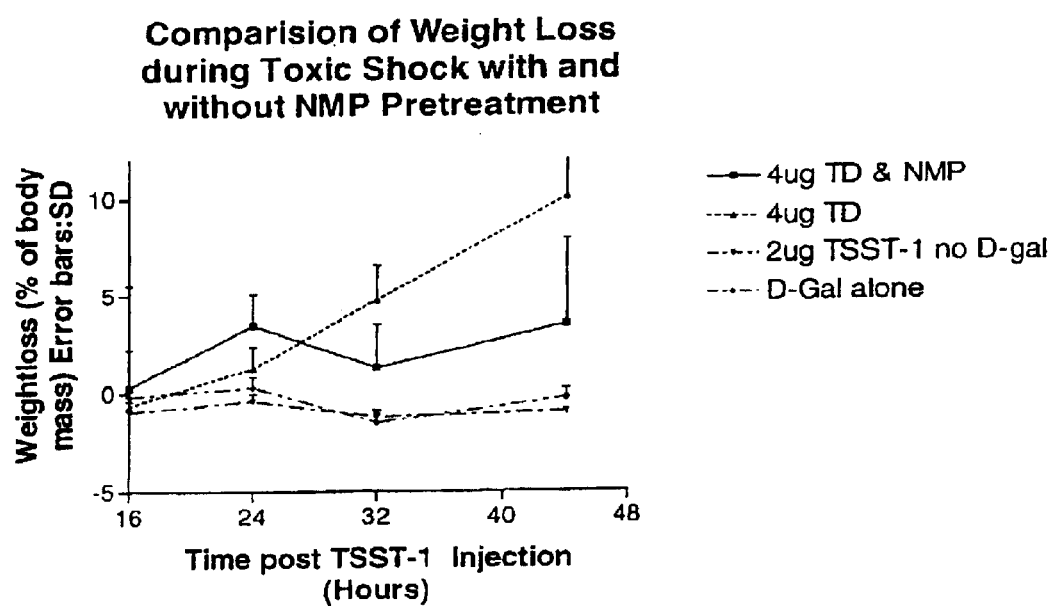

FIG. 22. IR pretreatment also resulted in significantly reduced weight loss of survivors of toxic shock.

Figure 23:
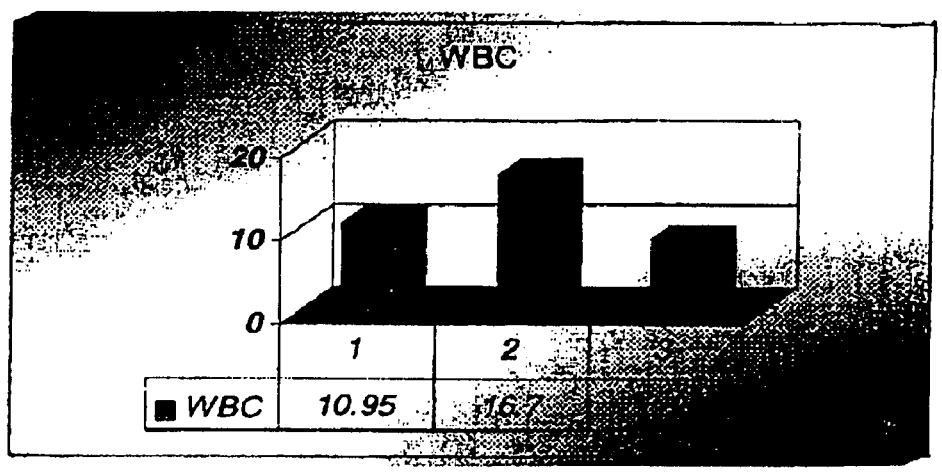

FIG. 23. This figure indicates a higher level of immune activation in the mice suffering from lethal toxic shock (bar#2). There is still a normal level of WBC in the IR-P group (bar#3) as compared to normal Balb/c mice (bar#1).

Figure 24:
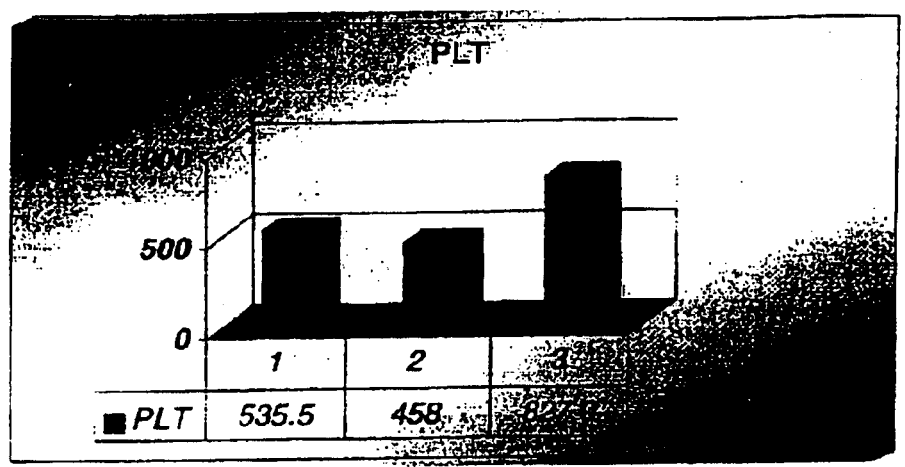

FIG. 24. This figure indicates slight reduction in platelets count in TSST-1 group (bar#2) as compared to normal Balb/c mice (bar#1). The platelets count were seen very high in IR-P treated group Balb/c mice (bar#3).

Figure 25:
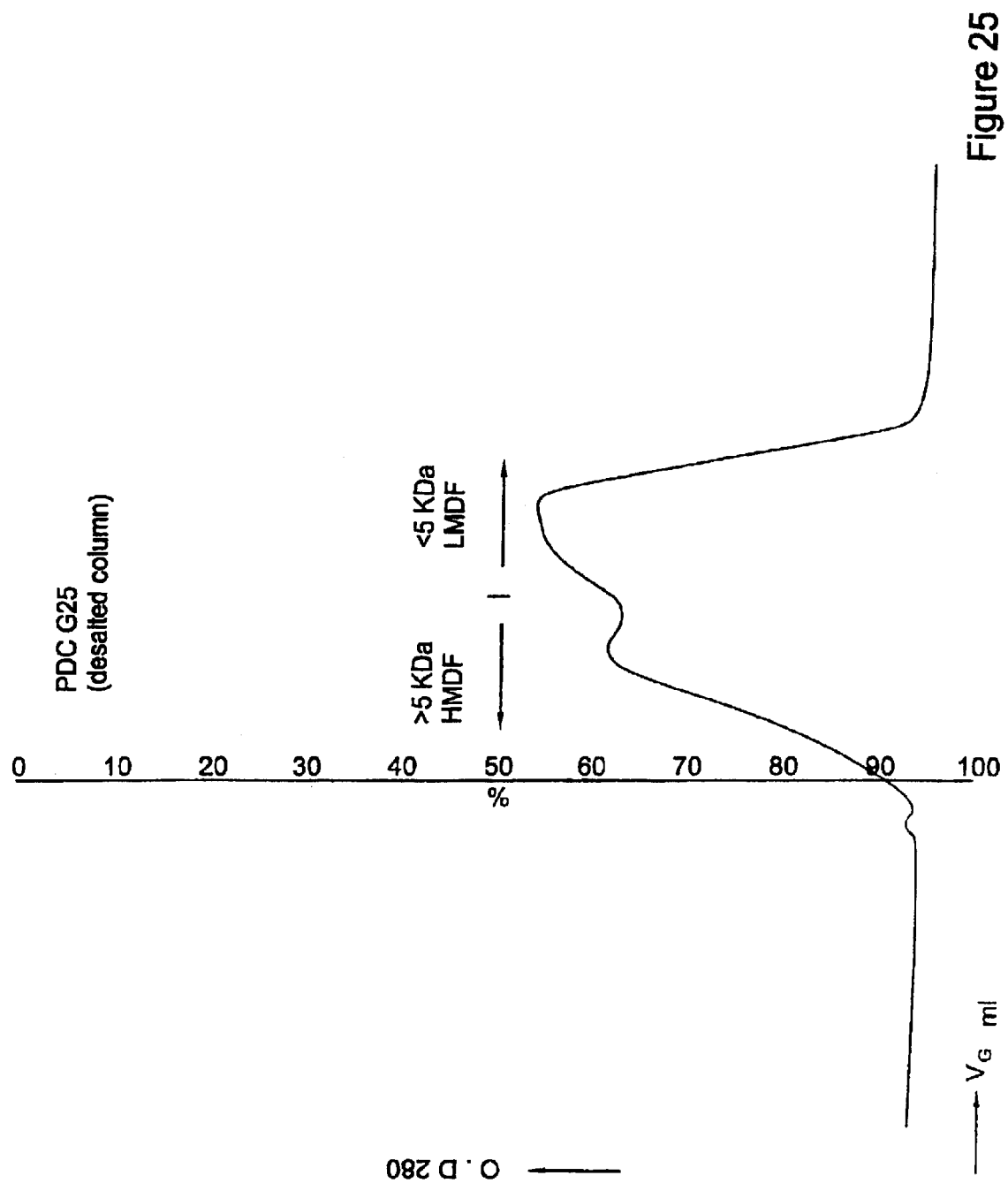

FIG. 25. This figure shows FDC G25 chromatogram of first trimester pregnancy urine sample (IR-U). Fraction IR-U/HMDF (high molecular weight desalted column fraction) has apparently molecular weight of greater then 5 kDa, while IR-U/LMDF (low molecular weight desalted column fraction) has apparently molecular weight of less then 5 kDa.

Figure 26:
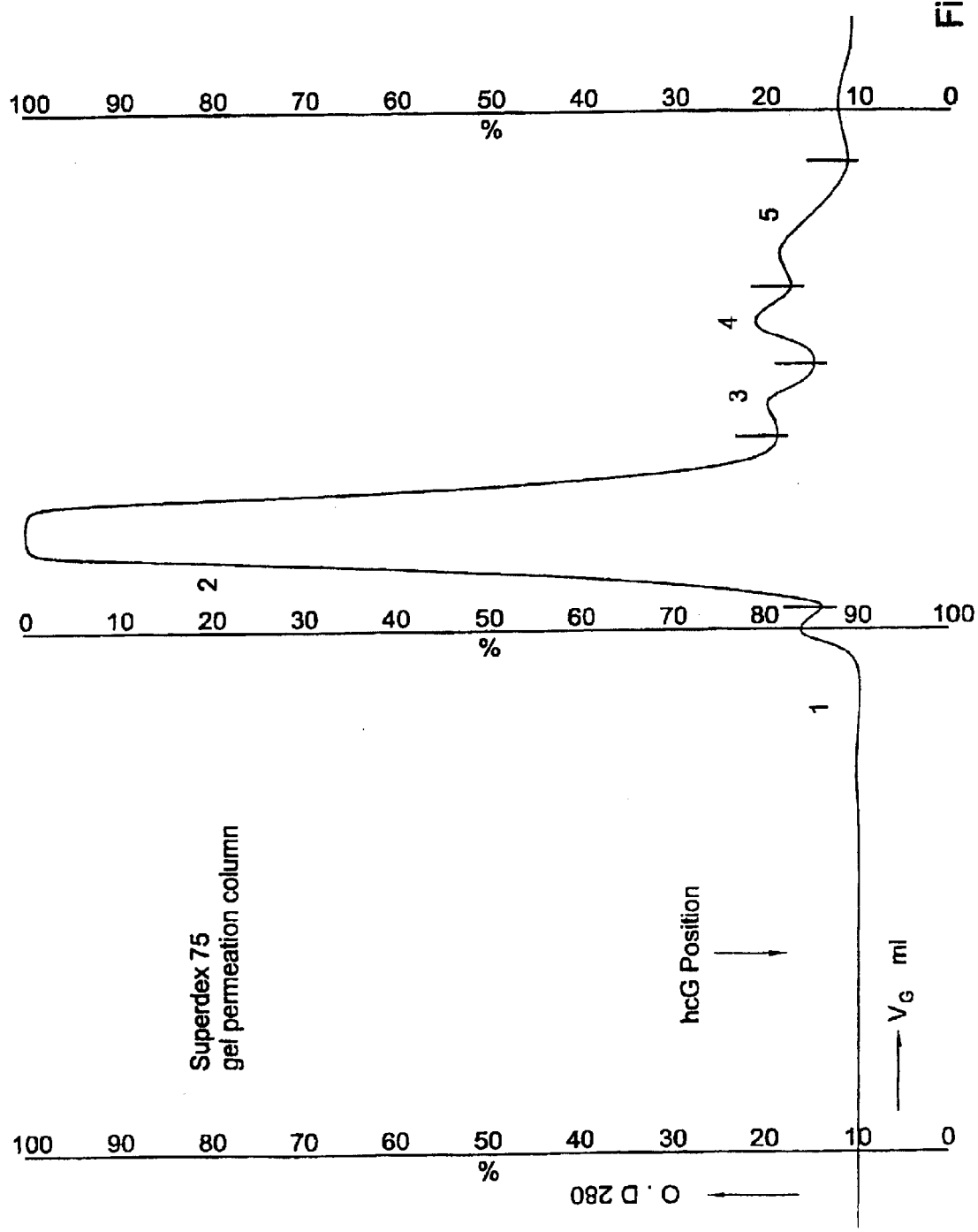

FIG. 26. This figure shows a Superdex 75 GPC chromatogram of IR-U/LMDF sample. The profile obtained displayed at least 5 peaks although the ratios were different.

Figure 27:
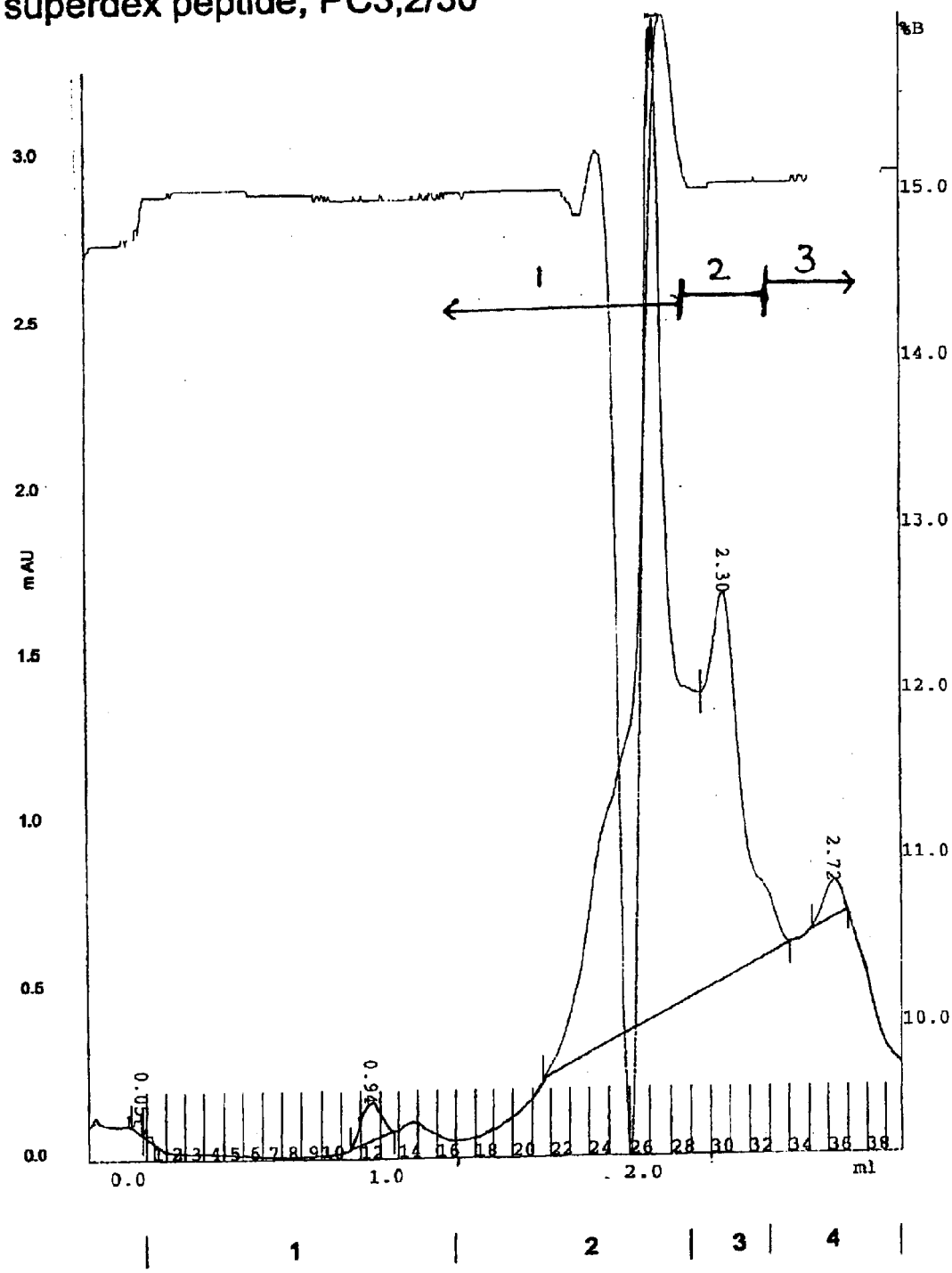

FIG. 27, shows low molecular weight fraction (IR-U/LMDF) on a Pharmacia Biotech SMART system equipped with a Superdex®peptide, PC 3.2/30. For the running buffer 40 mM Tris, 5 mM $MgCl_2$ 150 mM NaCl was used and the flow rate was 50 ml/min for 75 minutes and the signal was analyzed at 214 and 254 nm wavelength. There were 1-3 fractions collected (LMDF1-3). Cytochrome C and Gly16 were used as internal size markers. Peak [1], 2 and 3 were eluted at about 1.3 kDa, 1.15 kDa, 400Da, respectively.

FIG. 28. This figure shows that there is strong inhibition of IFN-gamma production found with IR-P and IR-U/LMDF on CD4+ cells polarizing towards Th1 phenotype (in vivo). There was only a moderate inhibition of IFN-gamma production observed with recombinant beta-hCG and no effect was seen with recombinant hCG as compare to control (MED)

Figure 29A:
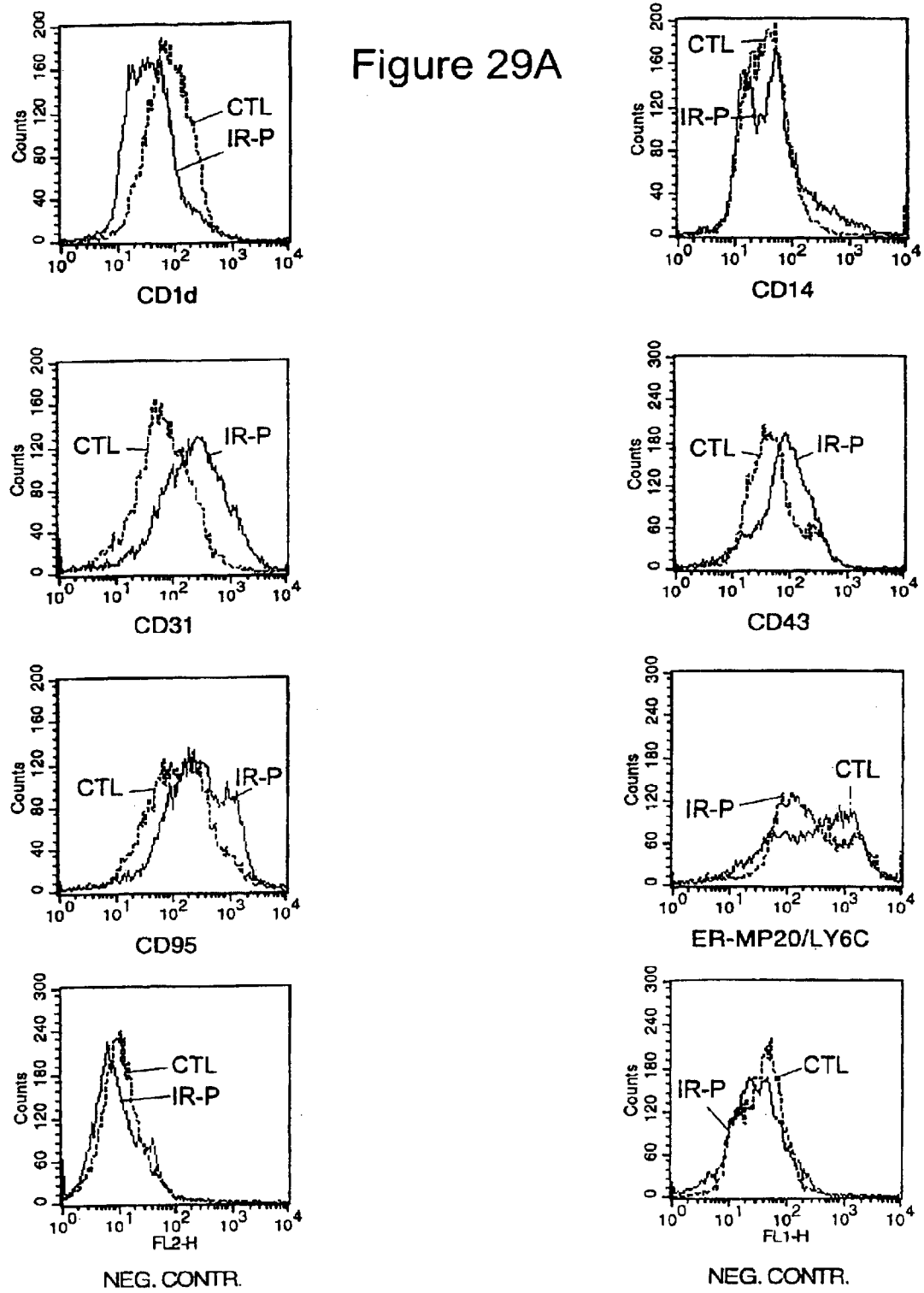
Figure 29B:
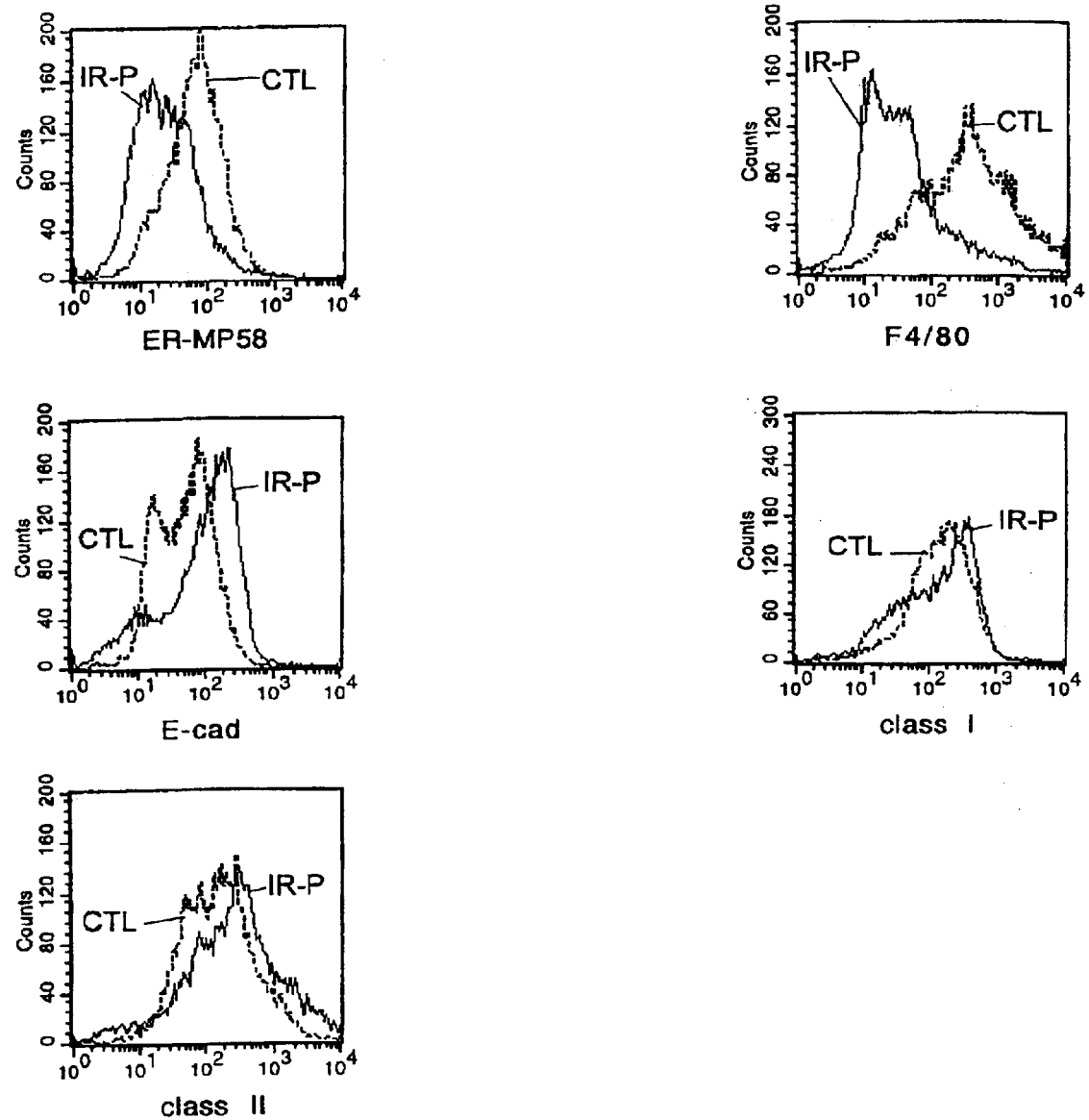
Figure 30A:
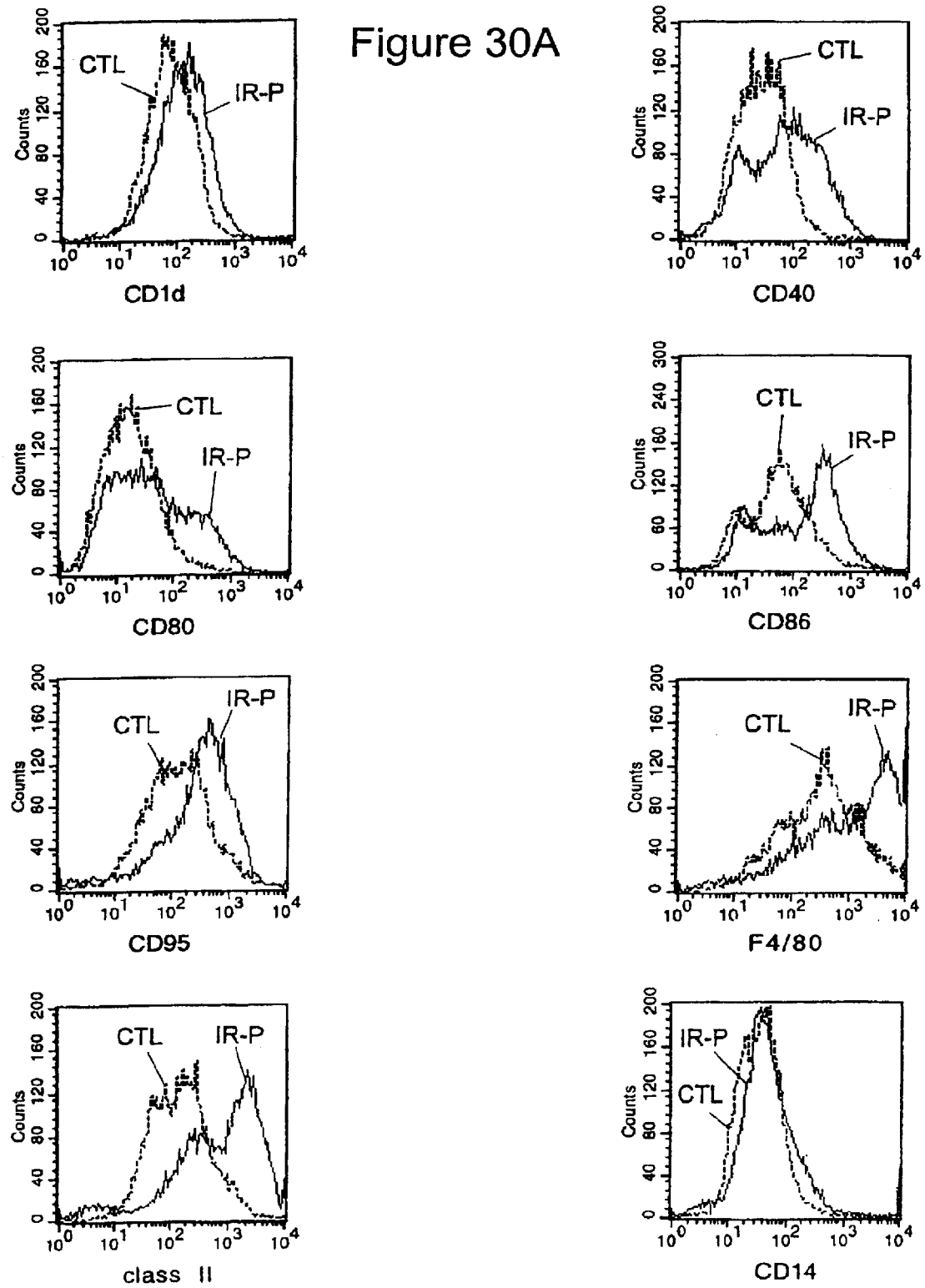
Figure 30B:
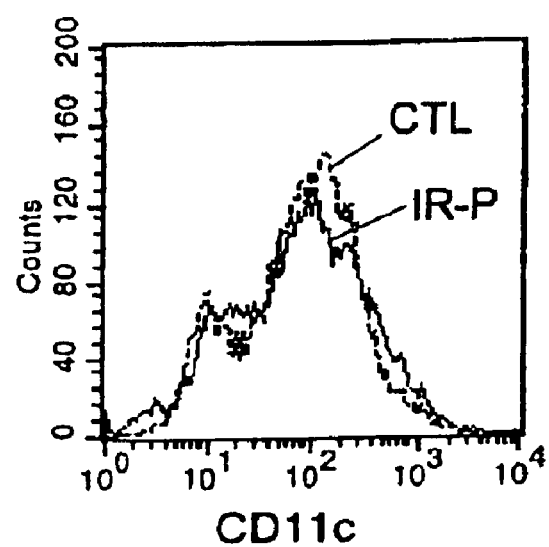

FIGS. 29–31. In order to know whether IR has also effect on the maturation of DC, BM from NOD mice were also directly co-cultured with GM-CSF and IR for 7 days. At day 8 all cells were analyzed by a flow cytometer for expression of the following markers: CD1d, CD11c, CD14, CD31, CD40, CD43, CD80, CD86, CD95, ER-MP20, ER-MP58, F4/80, E-cad, MHC II, MHC I, RB6 8C5. We observed that all DC treated with IR were less mature than control DC treated with GM-CSF only. This was concluded from the decrease in cell surface markers CD1d, ER-MP58, F4/80, CD14, and the increase in CD43, CD95, CD31 and E-cad. Moreover no change was observed in cell surface markers ER-MP20/LY6C, MHC I and II (FIGS. 29A and 29B). FIGS. 30A, 30B and 31 show, when DC were cultured with GM-CSF for 6 days and at day 7 co-cultured with 30 IU/ml IR-P (FIG. 30) or 100 mg/ml of IR-U/LMDF (FIG. 31) for additional 24 hrs, the DC became more mature and could function better as APC. This was concluded from the increase in CD1d, CD40, CD80, CD86, CD95, F4/80, CD11c and MHC II cell surface markers (FIGS. 30A, 30B and 31).

Figure 32:
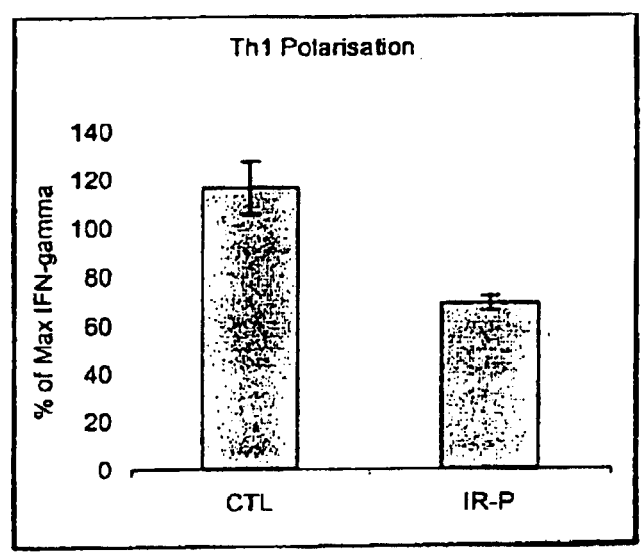

FIG. 32 shows that due to the IR-P treatment in BALB/c mice the CD4+ cell are shifted towards Th2 phenotype, appearing from the inhibition of IFN-gamma production as compared to control (CTL) group.

Figure 33:
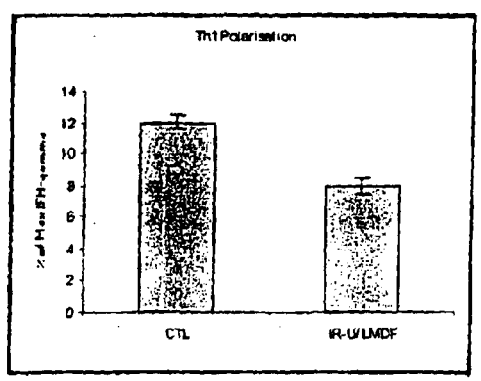

FIG. 33. Shows that purified CD4+ cells of BALB/c mice treated with IR-U/LMDF produce less IFN-gamma in Th1 polarisation assay as compare to PBS treated mice, suggestive of down-regulation of Th1 subsets.

FIG. 34 shows that due to the IR-P treatment in BALB/c mice the CD4+ cell are shifted towards Th2 phenotype, appearing from the increase in IL-4 production as compared to control (CTL) mice.

FIG. 35. shows that purified CD4+ cell of BALB/c mice treated with IR-U/LMDF produce more IL-4 in the Th2 polarisation assay as compare to PBS treated mice, suggestive of up-regulation of Th2 subsets.

Figure 36:
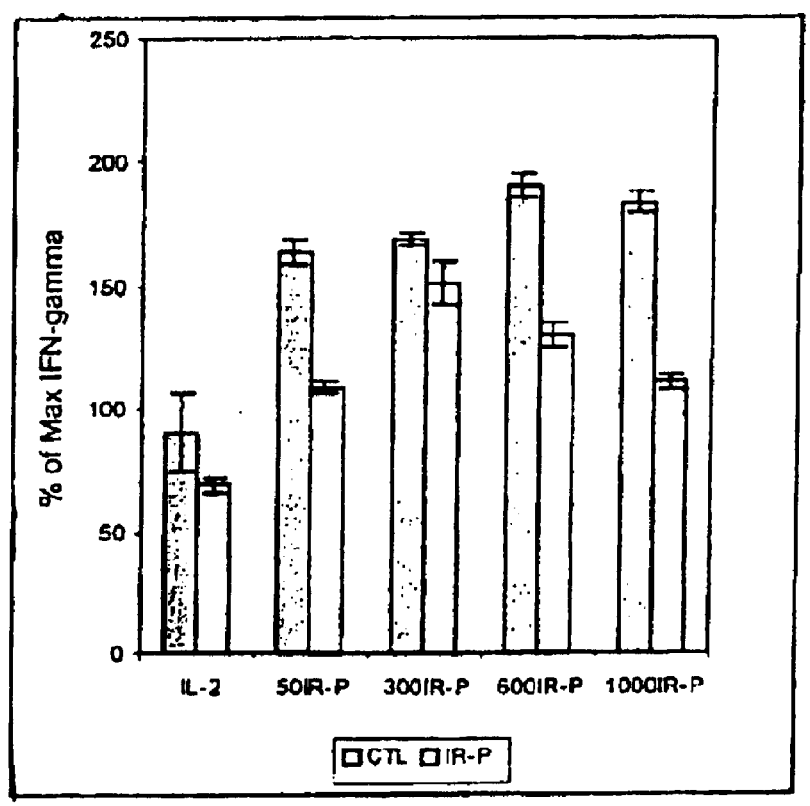
Figure 37:
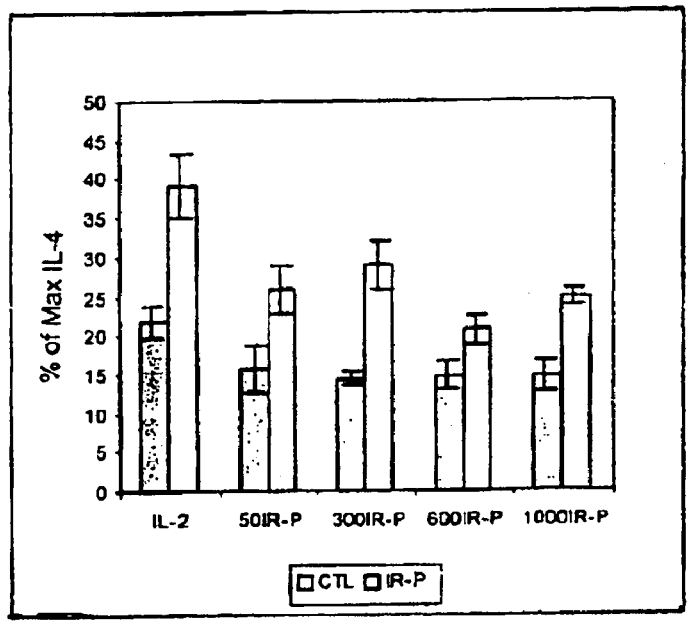

FIG. 36 shows that CD4+ T cells from PBS and IR-P mice treated (in vivo) with different doses of IR-P (in vitro) show increase in IFN-gamma production which suggest the shift towards Th1 phenotype (see also FIG. 37).

FIG. 37. Shows that CD4+T cells from PBS and IR-P mice treated (in vivo) with different doses of IR-P (in vitro) show decrease in IL-4 production which suggests the shift towards Th1 phenotype (see also FIG. 36).

Figure 38:
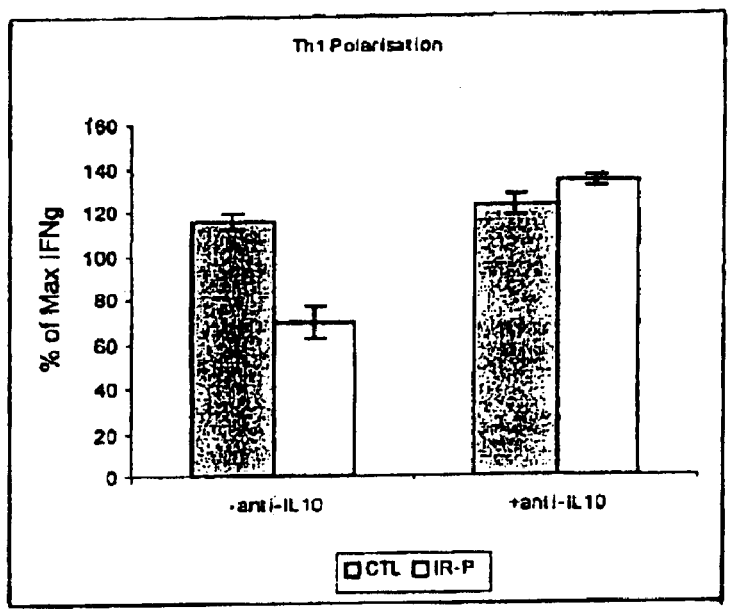
Figure 39:
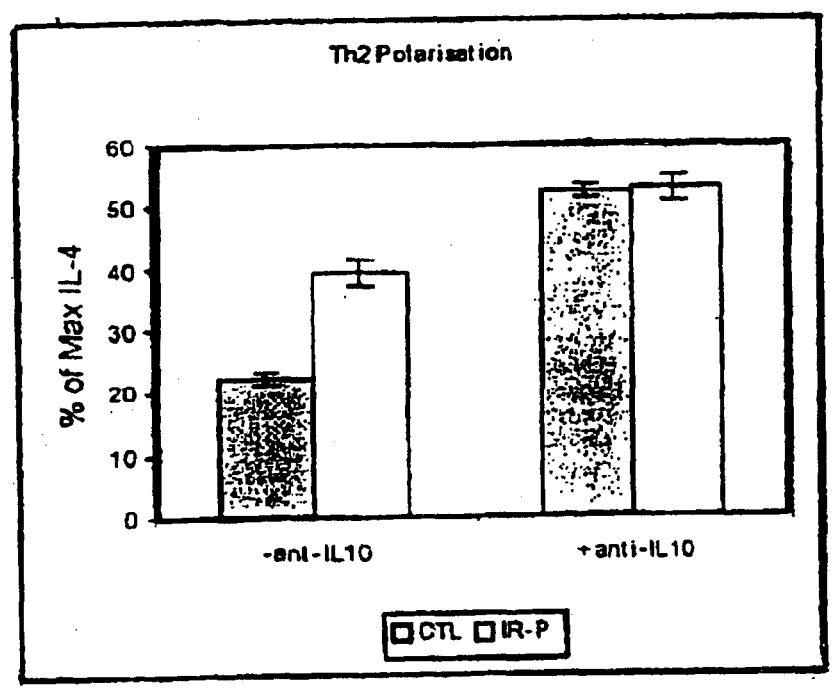

FIGS. 38–41. In order to determine whether a shift of CD4+ T cells towards the Th2 phenotype is IL-10 or TGF-beta dependent, we also added anti-IL10 and anti-TGF-beta in the polarization assays of CD4+ T cells from IR-P treated mice. FIG. 38 shows an increase in IFN-gamma production under Th1 polarization conditions in IR-P group, which suggests that the promoting effect of IR-P on Th2 subset is at least partly IL-10 dependent (for details see text). FIG. 39. shows increase in IL-4 production in Th2 polarization conditions seen with anti-IL10 invitro treatment in control (CTL) group and in IR-P group. This suggests involvement of IL-10 in Th1/Th2 polarisation (for detail see text), while no big differences were seen in of IL-4 and IFN-gamma production in Th2 and Th1 polarization conditions with anti-TGF-beta in vitro treatment (FIGS. 40 and 41) between control and IR-P treated group.

Figure 44:
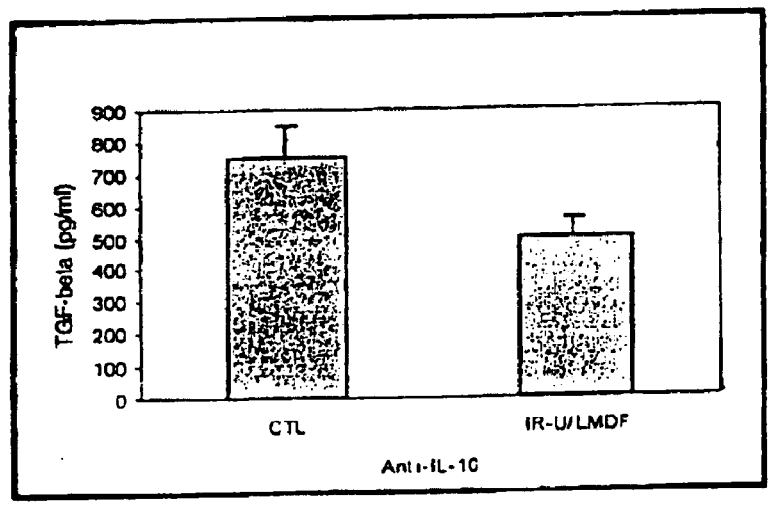
Figure 44:
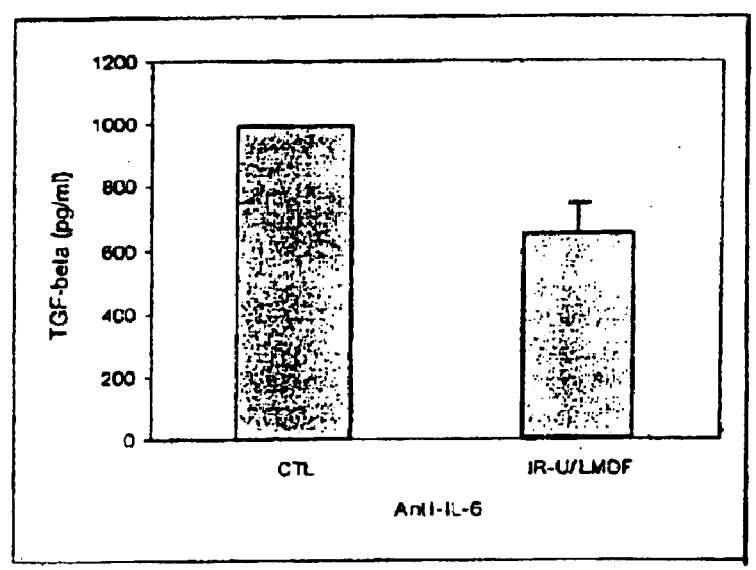

FIGS. 43, 44a,b and 45 show that purified CD4+ cell from IR-U/LMDF produce more TFG-beta then the cells from control mice. When anti-IL-10 or anti-IL-6 was added in both cultures, CD4+ cell from control group mice produce more TGF-beta then IR-U/LMDF treated group. This suggest an involvement of IL-6 and IL-10 in TGF-beta production. This is consistent with our data which shows that LPS stimulated spleens cells from IR treated mice produce high level of IL-6 (FIG. 45) as compared to control mice group.

FIGS. 46 and 47. Shows reduction in LPS and anti-CD3 induced proliferation was observed after culture of splenocytes from UVB treated BALB/c mice (FIGS. 46 and 47), while IR or combined IR and UVB-irradiated treatment increased the LPS and anti-CD3 stimulated proliferation (FIGS. 46 and 47).

Figure 48:
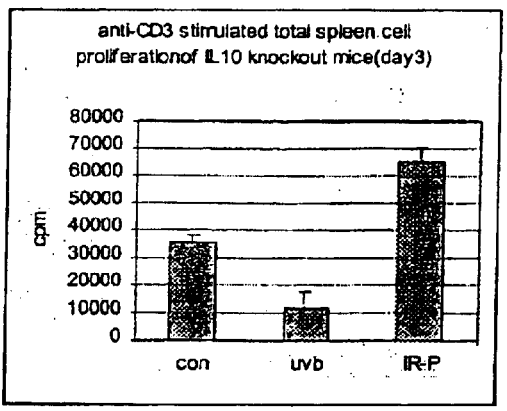

FIGS. 48 and 49. In order to determine whether this change in LPS and anti-CD3 stimulated proliferation is IL-10 dependent, we treated IL-10 knockout mice with IR-P or UVB. No change in proliferation pattern was seen in anti-CD3 stimulated spleen cells when UVB-irradiated and IR-P treated BALB/c mice were compared (FIG. 47), while the inverse pattern in proliferation was observed in anti-CD3 stimulated lymph node cells as compare to UVB-irradiated BALB/c of both groups (FIG. 49). This shows that the decrease in anti-CD3 stimulated proliferation after UVB treatment or increase in proliferation after IR-P treatment of spleen cells is not completely IL-10 dependent, while this is true for anti-CD3 stimulated lymph node cells.

Figure 51:
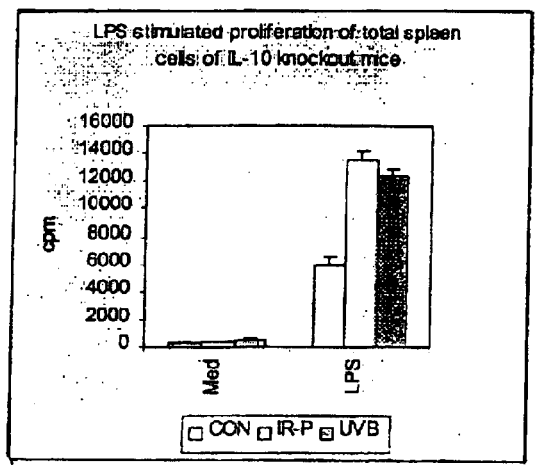

FIGS. 50 and 51. Shows the LPS stimulated proliferation of spleen cells at 48 hours, we observed an increase of proliferation in the UVB and IR-P treated groups as compared to the control group (FIG. 51), while a decrease in proliferation was observed in both groups at 72 hours of proliferation (FIG. 50).

Figure 52:
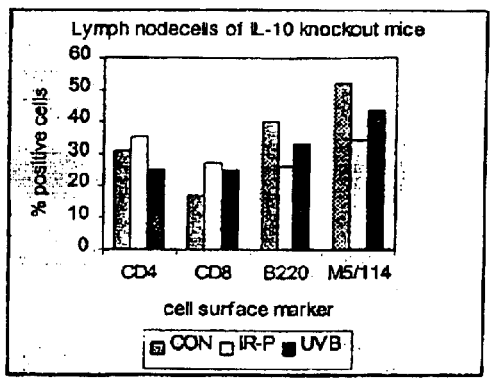
Figure 53:
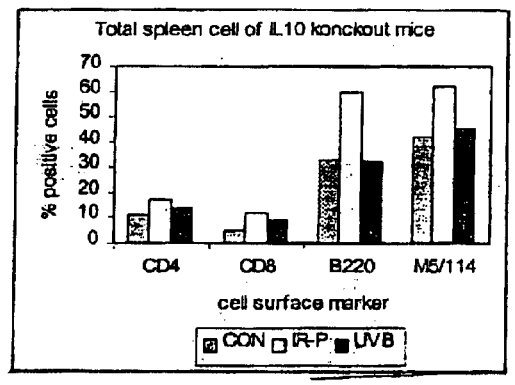

FIGS. 52 and 53. Shows that reduction in B220 and M5/114 positive cells, and an increase in CD4 and CD8 positive cells was observed in the lymph nodes of IR-P- treated IL-10 knockout mice (FIG. 52), while an increase in CD4, CD8, B220 and M5/114 positive cells was observed in the spleen (FIG. 53). In the UVB treated group, an increase in CD8 positive cells and a decrease in CD4, B220, and M5/114 positive cells was seen in lymph nodes (FIG. 52), while no change in cell markers was observed among spleen cells, except for a moderate increase in CD8 positive cells (FIG. 53).

FIGS. 54 and 55. Shows that when DC from BALB/c mice are co-cultured in the presence of GM-CSF and IR (IR-P, IR-U, IR-U3-5, IR-U/LMDF) for 7 days, we observed that all DC treated with IR were less mature than control DC treated with GM-CSF only. This was concluded from the decrease in cell surface markers CD1d, CD40, CD80, CD86, ER-MP58, F4/80, E-cad and MHC II (FIG. 54). Moreover, moderate increase in CD95 was observed (FIG. 54). In contrast, when DC were cultured with GM-CSF for 6 days and on day 7 the culture were supplemented with 300 IU/ml IR-P or 100 mg/ml IR-U (IR-U, IR-U3-5, or IR-U/LMDF) for additional 24 hrs, they became more mature and could function better as APC. This was concluded from the increase in CD1d, CD14, CD40, CD80, CD86, CD95, ER-MP5B, F4/80, RB6 8C5, E-cad and MHC II cell surface markers (FIG. 55).

FIG. 56. shows an allo-MLR. Proliferation data shows that IR treated DC in all DC versus T cells ratios are able to suppress proliferation (FIG. 56).

Figure 57:
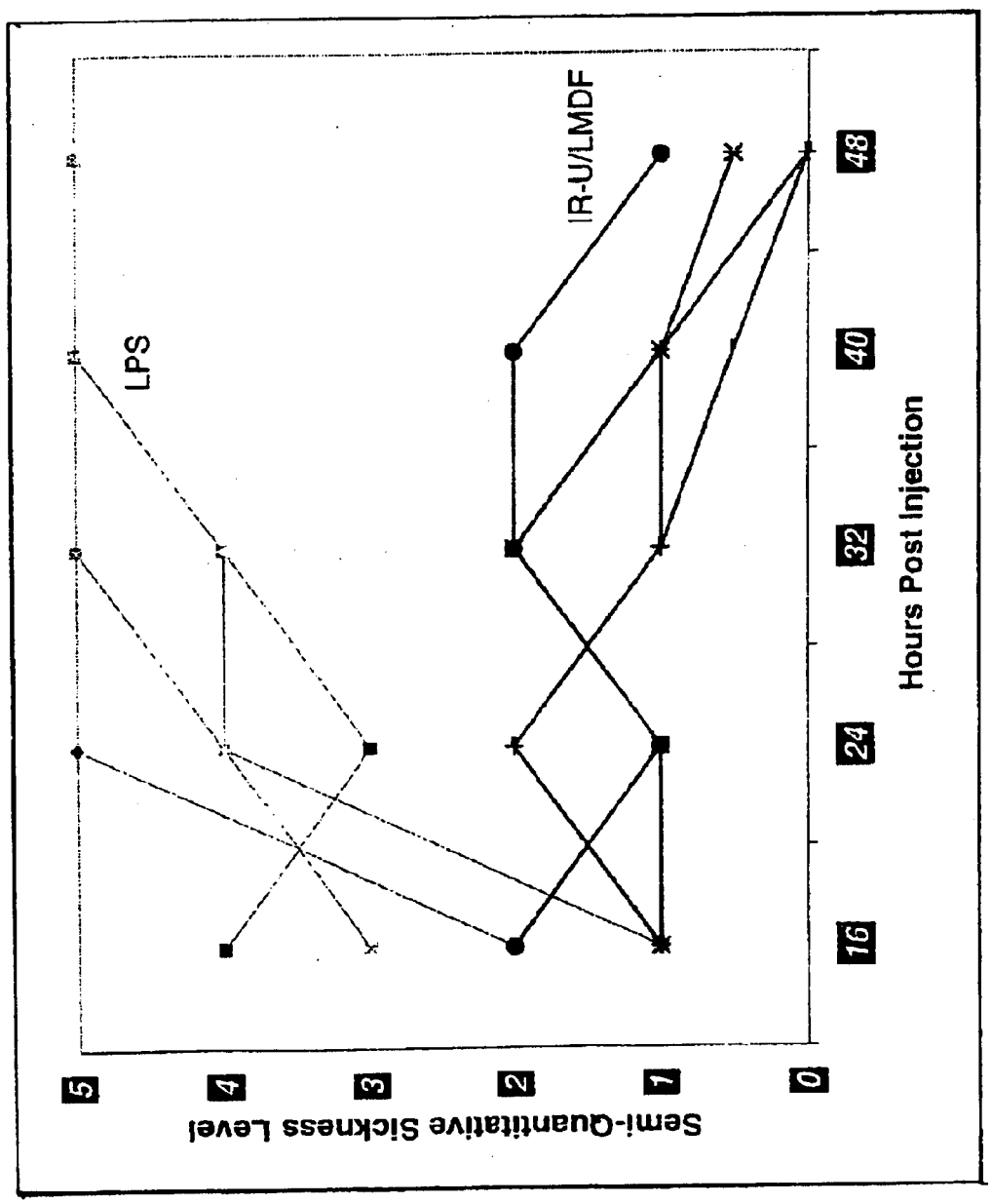

FIG. 57. shows anti-shock activity of IR-U/LMDF fraction. Method for test activity is mentioned elsewhere in this document.

FIG. 58. To determine the effect of high-dose LPS treatment in IR treated mice, BALB/c mice (n=30) were injected intraperitoneally with LPS (150 mg/kg) and survival was assessed daily 5 during days. PBS-treated BALB/c mice succumbed to shock between days 1 and 2 after high-dose LPS injection, with only 10% of mice alive on day 5 (FIG. 58). In constrast, 100% of IR-P, or its fractions IR-P1 or IR-P3, treated mice were alive on day 5 (P<0.001) (FIG. 58), while groups of IR-P2, IR-A and Dexamethasone treated mice demonstrated around 70% of survivers FIG. 59. shows that IR-A, IR-P and its fraction IR-P1, IR-P3 have all platelets counts within normal range ($100-300 \times 10^9$/ml), while control, IR-P2 and Dexamethasone treated mice have platelets counts below normal range.

FIGS. 60–62. shows that mice treated with IR-A, IR-P and its fraction IR-P1, IR-P2 or IR-P3 bad relatively lower level of ALAT, LDH1, ASAT enzymes in the plasma as compared to control and dexamethasone treated mice. These enzymes were present in higher concentration in blood during shock due to organ damage, so these results are consistent with our surviving results (FIG. 58).

FIG. 63. shows that mice treated with IR-A, IR-P and its fractions have moderate to normal level of WBC at t=48 hours than control and dexamethasone treated mice, suggesting weaker inflammatory responses in IR treated mice.

FIG. 64. shows inhibition of IFN-gamma production in Th1 polarisation assay of CD4+ cells isolated from NOD mice treated with IR-P or rhCG in combination with IR-P3, while moderate inhibition was found in Th1 polarisation by rhCG and IR-P3 alone. This shows that in treatment with rhCG in combination with IR-P3 give massive inhibition of Th1 outgrowth in NOD mice. This suggests that IR-P3 fraction needs rhCG for it maximal inhibition of the Th1 subset.

FIG. 65. shows inhibition of IFN-gamma production in anti-CD3 stimulated spleen cells obtained from NOD mice treated with I—P, IR-P1, IR-P2 or with rhCG in combination with IR-P3 as compared to PBS treated mice. rhCG and IR-P3 alone did not have the same effect as in combination. This suggests again that IR-P3 fraction need rhCG for its IFN-gamma inhibition.

FIG. 66. shows anti-CD3 stimulated proliferation at different time points (t=12, 24, 48 h) of spleen cells obtained from NOD mice treated with IR-P, its fractions, rhCG or IR-P3 in combination with rhCG. Again the results are consistent with the previous IFN-gamma inhibition (FIG. 65). Here, IR-P3 fraction also needed rhCG for its inhibitory effect on anti-CD3 induced proliferation of spleen cells from in vivo treated NOD mice.

FIG. 67. shows that IR-P and its fractions promote IL-10 production of anti-CD3 stimulated spleen cells from treated NOD mice as compared to PBS treated mice.

FIG. 68. shows that IgG2a production is not inhibited by in vivo treatment of NOD mice with IR-P2 and rhCG in vivo treatment, while IR-P, IR-P1, IR-P3 and IR-P3 in combination with rhCG did inhibit the IgG2a production.

FIGS. 69 and 70. show that IR-P treatment is able to mechanism behind this delay is probably of different nature.

FIGS. 71–74). Results of BEAS 2B cell line: show that Dexamethasone is able to inhbit TNF-alpha induced IL-6 and RANTES production in BEAS 2B cell line. IR-P is also able to inhibit the production of TNF-alpha induced inflammatory cytokines. Moreover, dexamethasone was able to restore TNF-alpha induced down-regulation of anti-inflammatory TGF-beta cytokine, while IR-P not only restore TGF-beta production but also promote this anti-inflammatory cytokine further (FIG. 73). In addition, Dexamethasone and IR-P were both able to inhibit IFN-gamma induced production of RANTES (FIG. 74).

FIGS. 75 and 76. Flow cytometry analyses of BEAS 2B cell line; results show that Dexamthasone and IR-P both were able to down-regulate the TNF-alpha induced expression of HLA-DR and ICAM-1

Figure 80:
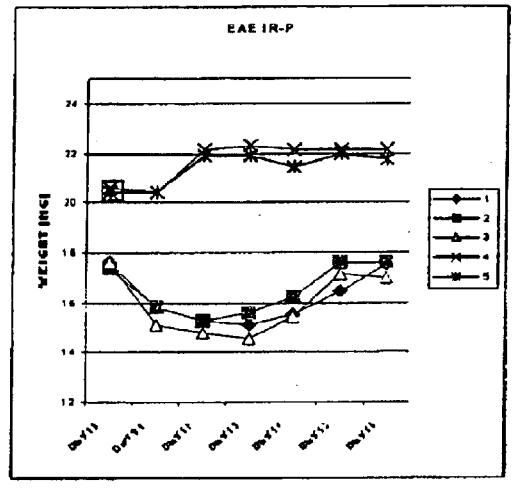

FIGS. 77–80. Result of EAE model; Mice treated with PBS only lost weight during the first three weeks (FIG. 77). These mice had all clinical signs of EAE of at least 2 and longer duration of the disease, except for one mice which remained resistance to disease during the whole experiment (FIG. 78). In IR treated mice group there was less weight lost observed during the experiment (FIG. 79) and two mice were free of disease during the experiment. Sick mice in this group had maximum clinical scores of 2 and had short duration of the disease, and recovered faster from EAE symptoms then PBS treated group (FIG. 80).

FIGS. 81, 82a, b. FIG. 81 shows that before IR treatment the patient was immuno-compromised due to the high dosis of steriods. After IR treatment the levels of T-lymphocytes (CD4, CD8) were increased and within normal range, except for B cells. We also measured cytokines in LPS and PMA/Ca stimulated PBMC obtained from patient during the IR treatment. We observed that LPS stimulated PBMC produced more TNF-alpha, IL-10 and IL-12 during treatment (FIG. 82a), while PMA/Ca stimulated PBMC produced less IFN-gamma (FIG. 82b).

FIGS. 83–86. FIG. 83 shows that due to the IR-P treatment the number of lymphocytes, T cells (CD4, CD8) and B cells were decreased which indicates the down-regulation of the hyperactive immune system due to the treatment. This is also consistant with our cytokine data (FIG. 86) which shows inhibition of LPS stimulated IL-12 and TNF-alpha by PBMC. Moreover, there was an increase in IL-10 production during the treatment, which is an anti-inflammatory cytokine (FIG. 86). In addition, the elevated CPK and liver enzymes (ASAT, ALAT) were also decreased (FIGS. 84 and 85). This all reflects a decrease in the disease activity.

FIGS. 87 and 88. Show that during IR-P treatment of diabets patient the insulin need to maintain euglycaemia decreased as shown in FIG. 87. After withdrawal of pregnyl his insulin need raised again (FIG. 87). In this patient with newly onset of diabetes mellitus the insulin need dropped significantly during treatment with IR-P and also improvement of the glucose control was found, supported by a decrease in glycosylated HbAlc level during IR-P treatment (FIG. 87) and decrease in inflammatory cytokines (IL12, TNF-alpha, INF-gamma) produced by LPS stimulated PBMC (FIG. 88). Furthermore, increase in IL-1 (antiinflammatory cytokine) was also observed during the treatment (FIG. 88). This all suggests an improvement of the island cell function and eventually also better glucose regulation.

Figure 89:
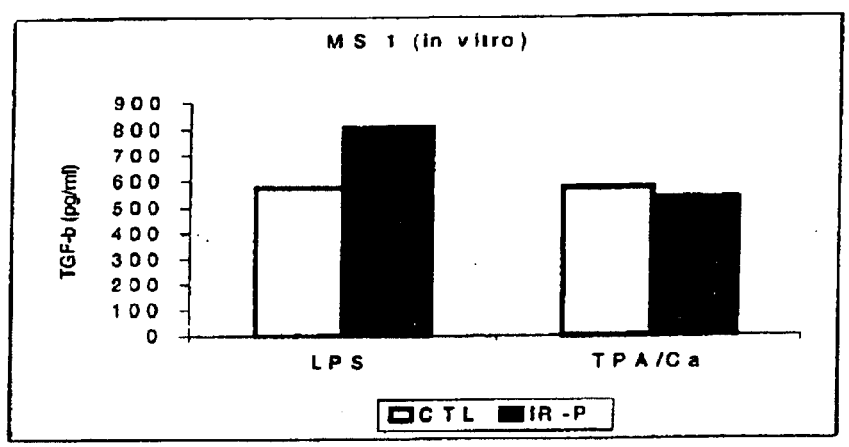
Figure 90:
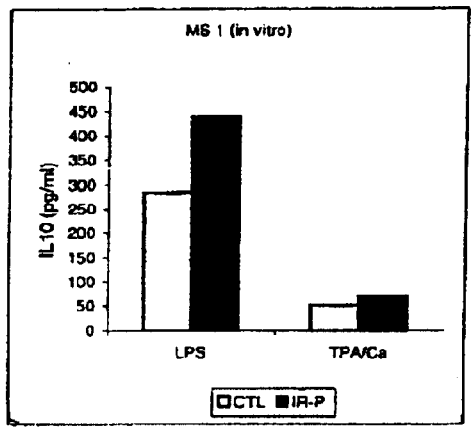
Figure 91:
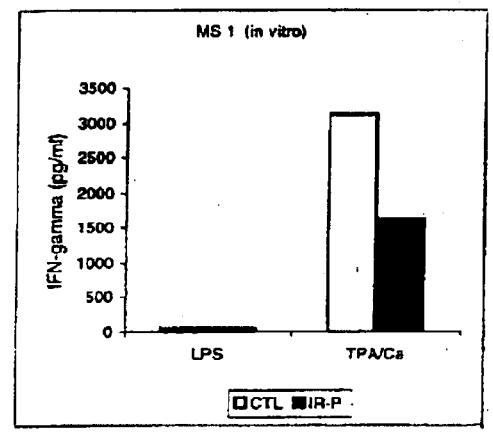

FIGS. 89–91. MS patient 1 (in vitro): there was an increase in production of TGF-beta and IL-10 in LPS stimulated PBMC treated with IR-P (FIGS. H and I). No differences were observed in TGF-beta and IL-10 production in cultures stimulated with PMA/Ca and treated with IR-P (FIGS. 89 and 90), while IR-P inhibited the production of IFN-gamma in PMA/Ca stimulated PBMC (FIG. 91).

FIGS. 92–94. MS patient 2 (in vitro): PBMC obtained from patient 2 showed a decreased production of TGF-beta and IFN-gamma in cultures treated with IR-P as compared to TPA/Ca stimulation alone, while IR-P treatment increased LPS stimulated TGF-beta production (FIGS. 92 and 93). IL-10 production was inhibited with IR-P in both LPS and TPA/Ca stimulated cultures (FIG. 94).

FIGS. 95 and 96. Treatment of BALB/c recipients with IR-P prolonged C57BL/6 skin graft survival as compared to the untreated control group. The control recipients rejected skin graft within 12 days (FIG. 95) while IR-P treated recipients were able to prolonged the graft till 22 days after transplantation (FIG. 96). FIGS. 95 and 96 show one such prolonged graft (picture taken on day 19) due to the IR-P treatment and a rejected graft from the control mice.

FIG. 97. show IR-U/LMDF Bio-Gel P-2 chromatogram.
FIG. 98. show IR-p3 Bio-Gel P-2 chromatogram.
FIG. 99. show IR-A3 Bio-Gel P-2 chromatogram.
FIG. 100. shows macrosphere GPC 60 Å chromatogram of a IR-P sample.

Three selected areas were fractionated, IR-P1 which elutes apparently with molecular weight of >10 kDa, IR-P2 which elutes aparently with molecular weight between the 10 kDa–1 kDa, and IR-P3 which elutes aparently with molecular weight <1 kDa. All these activities were tested for at least anti-shock activity (for details see text).

FIG. 101. shows macrosphere GPC 60 Å chromatrogram of IR-P and IR-A sample (500 IU of each sample was injected with a some injection volume). The results revealed that IR-A contains large amount of IR-A3 fraction as compare to IR-P3 fraction in the IR-P sample. We have tested same amount of IR-A and IR-P for their anti-shock activity. The results revealed that IR-A had low to moderate anti-shock activity compared to IR-P (result not shown).

Figure 102:
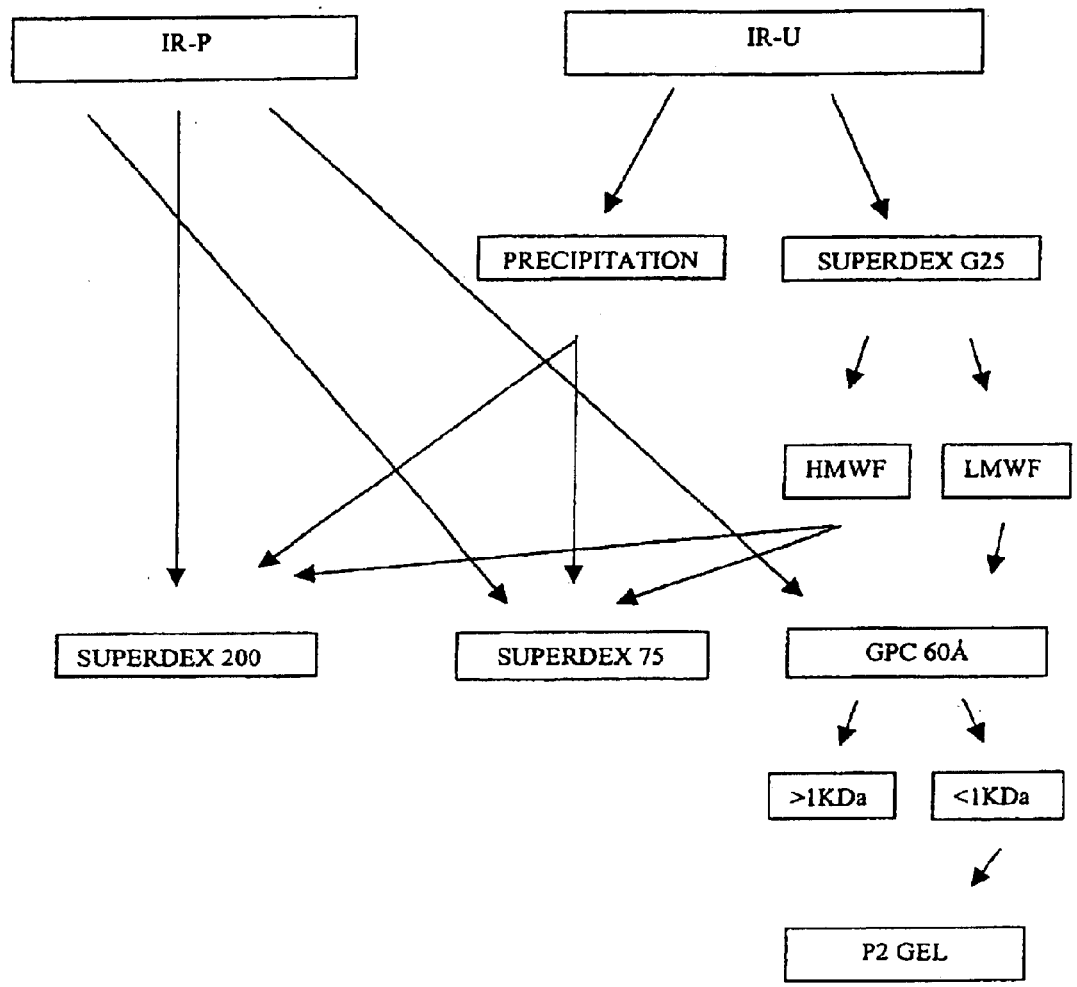

FIG. 102. shows flow diagram of purification methods 1, 2, 3 and 4 (for more detail., see text.

REFERENCES

Abbas, A. K., K. M. Murphy, and A. Sher. 1996. Functional diversity of helper T lymphocytes. Nature (Lond.). 383;787-793.

Argiles J. M., Lopez-Soriano J., Lopez-Soriano F. J. 1994. Cytokines and diabetes: the final step? Involvement of TNF-alpha in both type I and II diabetes mellitus. Horm. Metab.Res. 26:447–449.

Atkinson, M. A., and N. K. Maclaren. 1994. The Pathogenesis of insulin-dependent diabetes mellitus. N. Engl. J. Med. 331:1428–1436.

Bach, J. F. 1991. Insulin-dependent diabetes mellitus. Curr. Opin. Immunol. 3:902–905.

Buyon J. P. 1998. The effcts of pregnancy on auto-immune diseases. J. Leukoc. Biol. 63:281–287.

Elias D. 1994. The NOD mouse: a model for auto-immune insulin-dependent diabetes. (book) Auto-immune Models: A guidebook. 147-161.

Gill, P. S., Lunardi-Iskandar, Y. Gallo R. C. 1996. The effects of preparations of human chorionic gonadotropin on AIDS-related kaosi's Sarcoma. New Eng. J. Med. 335:1261–1269.

Grossman J. M., Brahn E. 1997. Rheumatoid arthritis: current clinical and research directions. J. Womens Health. 6:627–638.

Harada, M., and S. Makino. 1986. Suppression of overt diabetes in NOD mice by anti-thmocyte serum or anti-Thy 1, 2 antibody. Jikken. Dobutsu. 35:501–504.

Hintzen R. Q. 1997. Th-cell modulation in multiple sclerosis. Immunology today. 19:507–508.

Hotamisligil G. S., Spiegelman B. M. 1994. Tumour necrosis factor alpha: a key component of the obesity-diabetes link. Diabetes 43:1271–1278.

Katz, J. D., C. Benoist and D. Mathis. 1995. T helper cell subsets in insulin-dependent diabetes. Science (Wash. DC). 268:1185–1188.

Liblau, R. S., S. M. Singer, and H. O. McDevitt. 1995. Th1 and Th2 CD4+ T cells in the pathogenesis of organ-specific auto-immune diseases. Immunol. Today. 16:34–38.

Lunardi-Iskandar, . . . Gallo R. C. 1995. Tumourigenesis and metastasis of neoplastic kaposi'S sarcoma cell line in immunodeficient mice blocked by a human pregnancy hormone. Nature (Lond.). 375:64–68.

Lunardi-Iskandar, Y., Bryant, J. L. Blattnuer W. A., Hung C. L, Flamand L, Gill P., Hermans P., Birken S., and Gallo R. C. 1998. Effects of a urinary factor from women in early pregnancy on HIV-1, SIV and mediated disease. Nature Med. 4:428–434.

Makino, S., M. Harada, Y. Kishimoto, and Y. Hayashi. 1986. Absence of insulitis and overt diabetes in athymic nude mice with NOD genetic background. Jikken. Dobutsu. 35:495–498.

Miles P. D., Romeo O. M., Higo K., Cohen A., Rafaat K., Olefaky J. M. 1997. TNF-alpha-induced insulin resistance in vivo and its prevention by troglitazone. Diabetes 46:1678–1683.

Miyazaki, A., T. Hanafusa, K. Yamada, J. Miyagawa, H. Fujino-Kutihara, H. Nakajima, K. Nonake, and S. Tarui. 1985. Predominance of T lymphocytes in pancreatic islets and spleen of pre-diabetic non-obese diabetic (NOD) mice: a longitudinal study. Clin. Exp. Immunol. 60:622–630.

Ofei F., Hurel S., Newkirk J., Sopwith M., Taylor R. 1996. Effects of an engineered human anti-TNF-alpha antibody (CDP571) on insulin sensitivity and glycemic control in patients with NIDDM. Diabetes 4:881–885.

O'Garra, A., Steinman, L, and Gijbels, K. 1997. CD4+ T-cell subsets in auto-immunity. Curr. Opin. Immunol. 9(6): 872–883.

O'Reilly, L. A., P. R. Hutchings, P. R. Crocker, E. Simpson, T. Lund, D, Kiossis, F. Takei, J. Baird, and A. Cooke. 1991. Characterization of pancreatic islet cell infiltrates in NOD mice: effect of cell transfer and transgene expression. Eur. J. Immunol. 21:1171–1180.

Pakala, S. V., Kurrer, M. O. and Katz, J. D. 1997. T helper 2 (Th2) T cells induce acute pancreatitis and diabetes in immune-compromised nonobese diabetic (NOD) mice. J. Exp. Med. 186:299–306.

Pfeiffer A., Janott J., Mohlig M., Ristow M., Rochlitz H., Busch K., Schatz H., Schifferdecker E. 1997. Circulating tumour necrosis factor alpha is elevated in male but not in female patients with type II diabetes mellitus. Horm. Metab Res. 29:111–114.

Raghupathy R. 1997. Th1-type immunity is incompatible with successful pregnancy. Immunology today. 18:478–482.

Rosenberg, Y. J., Anderson, A. O., and Pabst, R. 1998. HIV-induced decline in blood CD4/CD8 ratios: viral killing or altered lymphocyte trafficking?. Immunology Today 19:10–16.

Russell A. S., Johnston C., Chew C., Maksymowych W. P. 1997. Evidence for reduced Th1 function in normal pregnancy:a hypothesis for the remission of rheumatoid arthritis. J. Rheumatol. 24:1045–1050.

Sempe. P., P. Bedossa, M. F. Richard, M. C. Villa, J. F. Bach, and C. Boitard. 1991. Anti-alpha/beta T cell receptor monoclonal antibody provides an efficient therapy for auto-immune diabetes in nonobese diabetic (NOD) mice. Eur. J. Immunol. 21:1163–1169.

Solomon S. S., Mishra S. K., Cwik C., Rajanna B., Postlethwaite A. E. 1997. Pioglitazone and metformin reverse insulin resistance induced by tumour necrosis factor-alpha in liver cells. Horm. Metab. Res. 29:379–382.

Zhu X. P, Satoh J., Muto G., Muto Y., Sagara M., Takahashi Seino H., Hirai S., Masuda T., Tanaka S., Ishida H., Seino Y., Toyota T. 1996. Improvement of glucose tolerance with immunomodulators on type 2 diabetic animals. Biotherapy 9:189–197.

Bennett, J C and Plum, F. Cecil textbook of medicine. 20th edition, page 496-501.

Freudenberg, M A, Keppler, D, and Galanos, C. (1986) Infect. Immun. 51, 891–895.

Perkins, David et al. (1994). Cellular immunology. 156, 310–321.

Huber, Pamer et al. (1993). Superantigens: a pathogens view of the immune system: Current communications in cell and molecular biology, vol. 7, coldspring harbor laboratory.

Miekthke, Thomas et al. (1992) J. Exp. Med. 175, 91–98.

Gutierrez-Ramos, JC and Bluethmann, H. (1997) Immunology today. 18, 329–334.

What is claimed is:

1. A method of treating an immune-related disorder caused by a hyperimmune or autoimmune response in a subject believed to be in need thereof, said method comprising:
   administering to the subject an amount of an immunoregulator, or functional fragment thereof, obtainable from a mammalian chorionic gonadotropin preparation,
   wherein said immunoregulator modulates Th1, Th2 or both Th1 and Th2 cell activity and is administered in an amount sufficient to modulate the immune-related disorder and wherein the immunoregulator is not mammalian chorionic gonadotropin, and comprises a non-carbohydrate containing active component having a molecular weight of less than 58 kilodaltons as determined by gel-permeation chromatography.

2. The method according to claim 1 wherein said immune-mediated disorder is selected from the group consisting of chronic inflammation, diabetes, multiple sclerosis, and chronic transplant rejection.

3. The method according to claim 1 wherein said immune mediated disorder is selected from the group consisting of acute inflammation, septic shock, anaphylactic shock, and acute or hyper acute transplant rejection.

4. The method according to claim 1 wherein said immune-mediated disorder is selected from the group consisting of auto immune disease, systemic lupus erythematosus, and rheumatoid arthritis.

5. The method according to claim 1 wherein said immune-mediated disorder is selected from the group consisting of allergy, asthma and parasitic disease.

6. The method according to claim 1 wherein said immune-mediated disorder is selected from the group consisting of an overly strong immune response directed against an infectious agent, a virus and bacterium.

7. The method according to claim 1 wherein said treatment comprises regulating relative ratios, cytokine activity or both relative ratios and cytokine activity of lymphocyte subset populations in a treated individual.

8. The method according to claim 7 wherein said subset populations comprise Th1 or Th2 cells.

9. A method for treating an immune mediated disorder caused by a hyperimmune or autoimmune response in a subject comprising:
   administering to the subject at least one immunoregulator, or functional fragment thereof, obtainable from a mammalian chorionic gonadotropin preparation, and having Th1 and Th2 cell regulating activity, said immunoregulator being administered in an amount sufficient to modulate dendritic cell differentiation and wherein the immunoregulator is not mammalian chorionic gonadotropin, but comprises a non-carbohydrate containing active component having a molecular weight of less than 58 kilodaltons as determined by gel-permeation chromatography.

10. The method according to claim 9 wherein said immune-mediated disorder includes diabetes.

11. The method according to claim 10 wherein said immune-mediated disorder includes sepsis.

12. The method according to claim 11 further comprising regulating relative ratios, cytokine activity or both relative ratios and cytokine activity of lymphocyte subset-populations in said subject.

13. The method according to claim 12 wherein said subset-populations comprise Th1 or Th2 cells.

14. The method according to claim 1 wherein the immunoregulator regulates Th 1, Th2 or both Th 1 and Th2 cell activity.

15. The method according to claim 1 wherein the immunoregulator modulates dendritic cell differentiation.

16. The method according to claim 1 wherein the immunoregulator comprises an active component, or a functional fragment thereof, obtainable from a mammalian chorionic gonadotropin preparation, wherein said active component stimulates splenocytes obtained from a non obese diabetes (NOD) mouse.

17. The method according to claim 1 wherein the immunoregulator, wherein said non-carbohydrate containing active component protects a mouse against a lipopolysaccharide induced septic shock.

18. The method according to claim 1 wherein the active component is a peptide.

19. The method according to claim 17 wherein said active component is present in a fraction which elutes with an approximate molecular weight of 1 to 15 kilodaltons as determined in gel-permeation chromatography.

20. The method according to claim 17 wherein said active component is present in a fraction which elutes with an approximate molecular weight of less than one kilodalton as determined in gel-permeation chromatography.

21. The method according to claim 16 wherein said stimulated splenocytes delay the onset of diabetes in a NOD severe combined immunodeficient mouse reconstituted with said splenocytes.

22. The method according to claim 21 wherein said active component inhibits gamma interferon production of splenocytes obtained from a non obese diabetes (NOD) mouse.

23. The method according to claim 22 wherein said active component stimulates interleukin-4 production of splenocytes obtained from a non-obese diabetes (NOD) mouse.

24. The method according to claim 23 wherein said active component reduces ASAT plasma levels after or during organ failure.

25. The method according to claim 2 wherein said treatment comprises regulating relative ratios, cytokine activity or both relative ratios and cytokine activity of lymphocyte subset populations in a treated individual.

26. The method according to claim 3 wherein said treatment comprises regulating relative ratios, cytokine activity or both relative ratios and cytokine activity of lymphocyte subset populations in a treated individual.

27. The method according to claim 4 wherein said treatment comprises regulating relative ratios, cytokine activity or both relative ratios and cytokine activity of lymphocyte subset populations in a treated individual.

28. The method according to claim 5 wherein said treatment comprises regulating relative ratios, cytokine activity or both relative ratios and cytokine activity of lymphocyte subset populations in a treated individual.

29. The method according to claim 6 wherein said treatment comprises regulating relative ratios, cytokine activity or both relative ratios and cytokine activity of lymphocyte subset populations in a treated individual.

30. The method according to claim 9 further comprising regulating relative ratios, cytokine activity or both relative ratios and cytokine activity of lymphocyte subset-populations in said subject.

31. The method according to claim 30 wherein said subset-populations comprise Th1 or Th2 cells.

32. The method according to claim 10 further comprising regulating relative ratios, cytokine activity or both relative ratios and cytokine activity of lymphocyte subset-populations in said subject.

33. The method according to claim 32 wherein said subset-populations comprise Th1 or Th2 cells.

34. A method of treating a disorder caused by a hyper-immune or autoimmune response in a subject, said method comprising: administering to the subject an active component, or functional fragment thereof, obtainable from a mammalian chorionic gonadotropin preparation, but which is not mammalian chorionic gonadotropin, so as to treat the disorder wherein the active component is a non-carbohydrate having a molecular weight of less than 58 kilodaltons as determined by gel-permeation chromatography.

* * * * *